United States Patent
Lee et al.

(10) Patent No.: US 11,752,091 B2
(45) Date of Patent: Sep. 12, 2023

(54) COMPOSITION FOR STRENGTHENING SKIN BARRIER, MOISTURIZING SKIN OR ANTI-AGING

(71) Applicant: COSMAX, INC., Hwaseong-si (KR)

(72) Inventors: Dong Geol Lee, Hwaseong-si (KR); Seung Hyun Kang, Seoul (KR); Mi Sun Kim, Suwon-si (KR); Min Ji Kim, Suwon-si (KR); Myeong Sam Park, Seoul (KR)

(73) Assignee: COSMAX, INC., Hwaseong-si (KR)

( * ) Notice: Subject to any disclaimer, the term of this patent is extended or adjusted under 35 U.S.C. 154(b) by 296 days.

(21) Appl. No.: 17/113,744

(22) Filed: Dec. 7, 2020

(65) Prior Publication Data

US 2021/0353527 A1    Nov. 18, 2021

(30) Foreign Application Priority Data

May 14, 2020   (KR) .................. 10-2020-0057823

(51) Int. Cl.
| | |
|---|---|
| A61K 35/744 | (2015.01) |
| A61K 8/99 | (2017.01) |
| A23L 33/135 | (2016.01) |
| A23L 33/00 | (2016.01) |
| A61K 8/41 | (2006.01) |
| A61Q 17/00 | (2006.01) |
| A61Q 19/00 | (2006.01) |
| A61Q 19/08 | (2006.01) |
| C12N 1/20 | (2006.01) |

(52) U.S. Cl.
CPC ............ *A61K 8/99* (2013.01); *A23L 33/135* (2016.08); *A23L 33/40* (2016.08); *A61K 8/41* (2013.01); *A61Q 17/00* (2013.01); *A61Q 19/007* (2013.01); *A61Q 19/08* (2013.01); *C12N 1/20* (2013.01); *A23V 2002/00* (2013.01)

(58) Field of Classification Search
CPC ..................................................... A61K 35/744
See application file for complete search history.

(56) References Cited

U.S. PATENT DOCUMENTS

| | | |
|---|---|---|
| 9,089,504 B2 | 7/2015 | Kang et al. |
| 10,449,222 B2 | 10/2019 | Desroche et al. |
| 2020/0215130 A1 | 7/2020 | Berkes et al. |

FOREIGN PATENT DOCUMENTS

| | | |
|---|---|---|
| EP | 2 740 482 A1 | 6/2014 |
| JP | 2016508712 A | 3/2016 |
| KR | 20180023012 A | 3/2018 |
| KR | 20180121269 A | 11/2018 |

(Continued)

OTHER PUBLICATIONS

English machine translation of Guongzhou Jinyi Bacteriophage Biotechnology Co. Ltd., He et al., CN 107794232 A, 2018.*

(Continued)

*Primary Examiner* — Rosanne Kosson
(74) *Attorney, Agent, or Firm* — Panitch Schwarze Belisario & Nadel LLP

(57) ABSTRACT

Provided is a composition comprising a novel strain, a lysate thereof or a culture product thereof, which can demonstrate excellent effects in strengthening skin barrier, moisturizing skin, enhancing skin elasticity or anti-aging, and can be used for a cosmetic composition or health functional food.

11 Claims, 60 Drawing Sheets

Specification includes a Sequence Listing.

(56) References Cited

FOREIGN PATENT DOCUMENTS

| KR | 101914157 B1 | 12/2018 |
|---|---|---|
| WO | 2010/056198 A1 | 5/2010 |
| WO | 2019111189 A1 | 6/2019 |

OTHER PUBLICATIONS

Alignment of instant Seq ID No. 1 and Sequence 27F of CN 107794323 A, performed on the NCBI Blast2 website, https://blast.ncbi.nlm.nih.gov/Blast.cgi?BLAST_SPEC=blast2seq&LINK_LOC=align2seq&PAGE_TYPE=BlastSearch, Jan. 31, 2023.*

"*Streptococcus mitis* strain NS51 16S ribosomal RNA, partial sequence", Source: https://www.ncbi.nlm.nih.gov/nucleotide/NR_028664.1?report=genbank&log$=nucla, 2 pages.

Korean Office Action dated Jul. 23, 2020, issued by the Korean Patent Office in corresponding Taiwan Patent Application No. 10-2020-0057823.

Korean Office Action dated Oct. 4, 2020, issued by the Korean Patent Office in corresponding Taiwan Patent Application No. 10-2020-0057823.

Eck et al., "Interpretation of Microbiota-Based Diagnostics by Explaining Individual Classifier Decisions," BMC Bioinformatices, (Oct. 4, 2017), vol. 18, No. 1, pp. 1-13.

Kim et al., "Spermidine-Induced Recovery of Human Dermal Structure and Barrier Function by Skin Microbiome," Communications Biology, (Jan. 1, 2021), vol. 4, No. 231, pp. 1-11. Retrieved from the Internet: URL:https://www.nature.com/articles/s42003-020-01619-4.pdf.

Park et al., "*Streptococcus gwangjuense* sp. nov., Isolated from Human Pericoronitis," Current Microbiology, (Apr. 26, 2019), vol. 76, No. 7, pp. 799-803.

Potter et al., "Spermidine Biosynthesis and Transport Modulate Pneumococcal Autolysis," Journal of Bacteriology, (Oct. 15, 2014), vol. 196, No. 20, pp. 3556-3561.

The extended European Search Report dated May 3, 2021, by the European Patent Office in corresponding European Patent Application No. 20212089.5-1111. (9 pages).

* cited by examiner

FIG. 3B

| Annotated COGs | | | Genes |
|---|---|---|---|
| S. infantis | 640 | | 107 |
| S. pneumoniae | 640 | 1. Grouping by genomic distance | 133 |
| S. mitis | 640 | 2. Matching COGs to genes | 96 |
| S. thermophilus | 640 | | 73 |

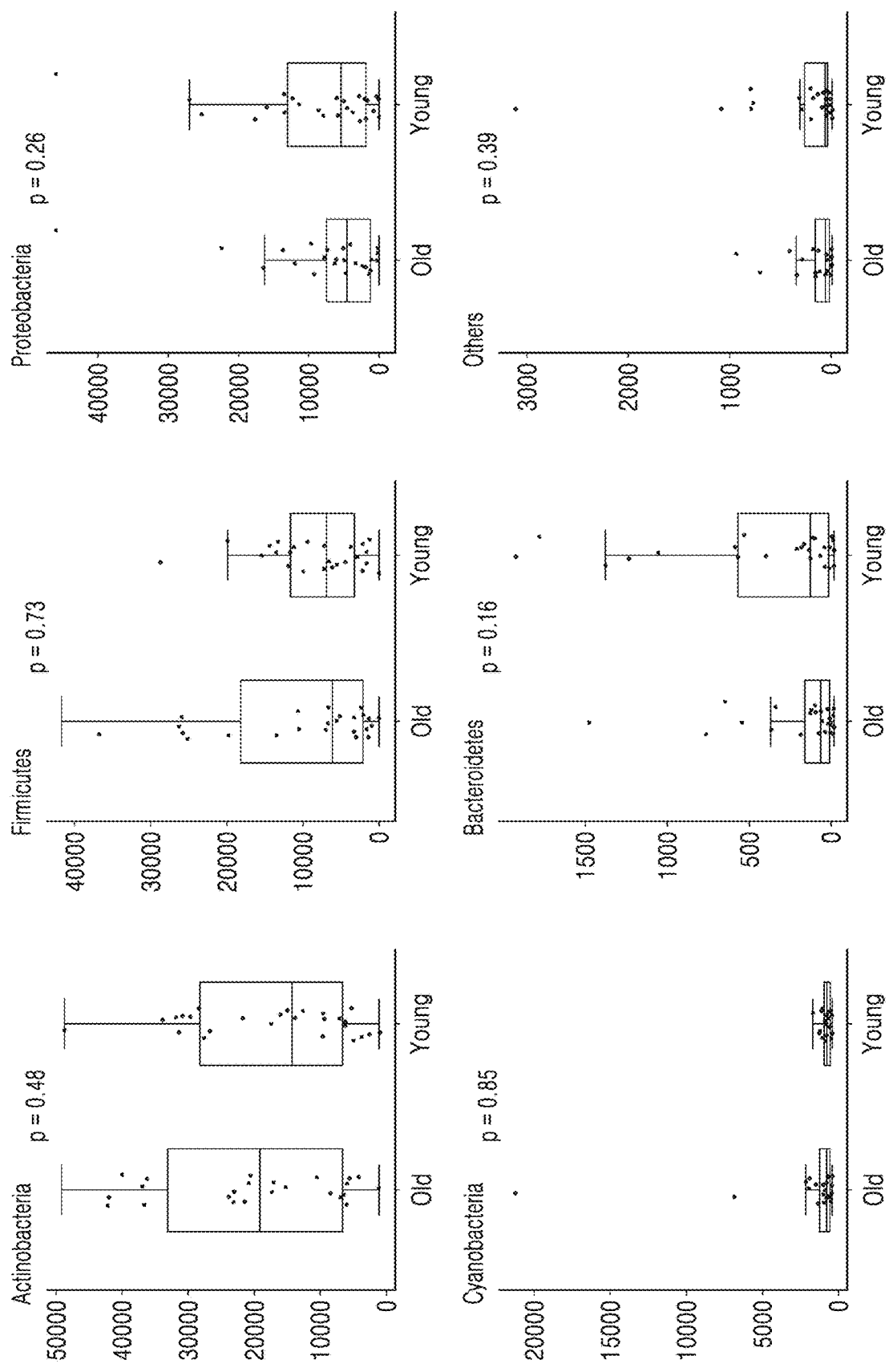

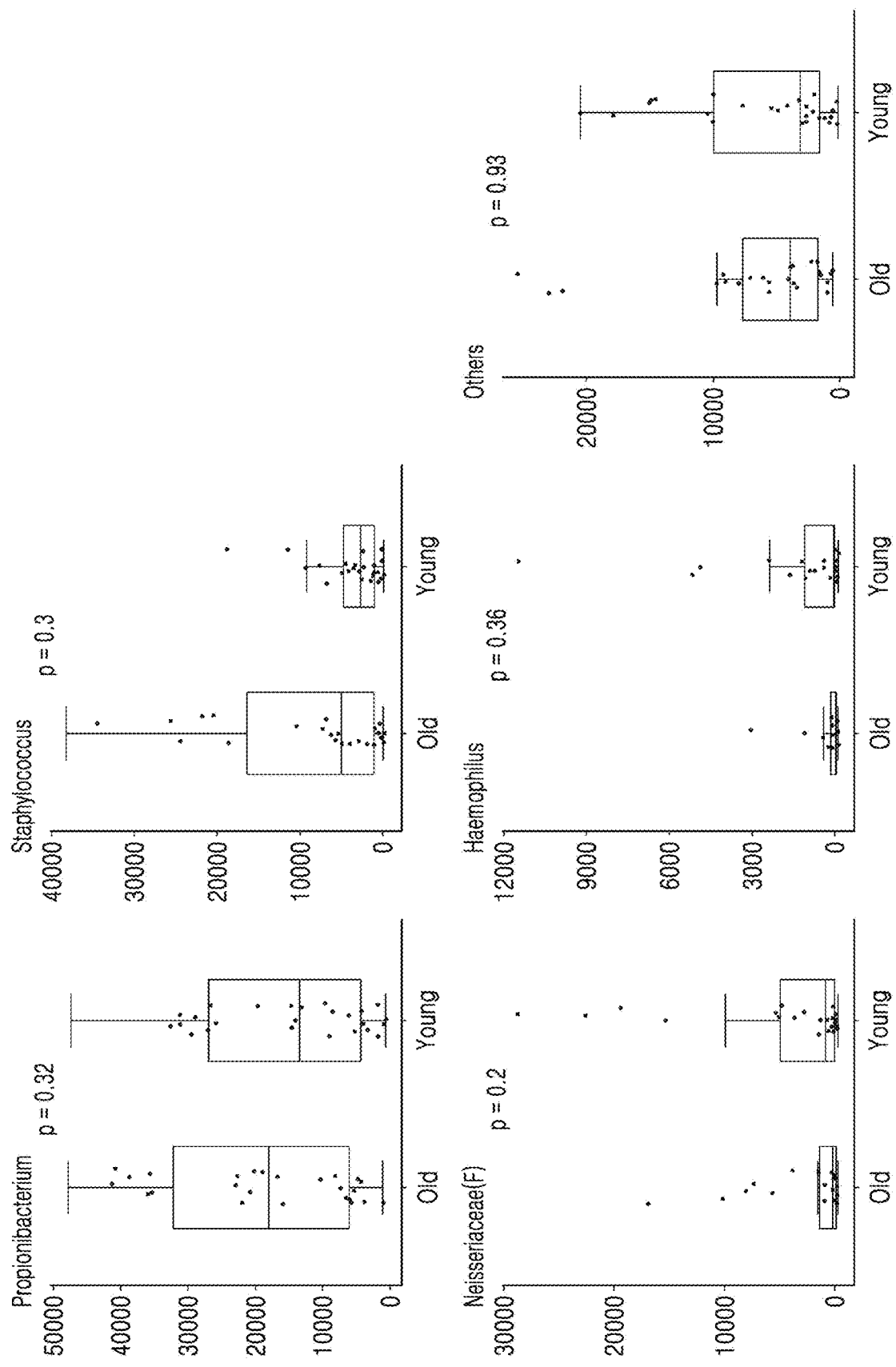

SEQUENCE LISTING

<160> NUMBER OF SEQ ID NOS: 1

<210> SEQ ID NO 1
<211> LENGTH: 1520
<212> TYPE: DNA
<213> ORGANISM: Streptococcus mitis
<220> FEATURE:
<223> OTHER INFORMATION: 16S rRNA

<400> SEQUENCE: 1

| | | | | | |
|---|---|---|---|---|---|
| ttttgagttt | gatcctggct | caggacgaac | gctggcggcg | tgcctaatac | atgcaagtag | 60 |
| aacgctgaag | gaggagcttg | cttctccgga | tgagttgcga | acgggtgagt | aacgcgtagg | 120 |
| taacctgcct | ggtagcgggg | gataactatt | ggaaacgata | gctaataccg | cataagagta | 180 |
| gatgttgcat | gacatttgct | taaaaggtgc | aattgcatca | ctaccagatg | gacctgcgtt | 240 |
| gtattagcta | gttggtgggg | taacggctca | ccaaggcgac | gatacatagc | cgacctgaga | 300 |
| gggtgatcgg | ccacactggg | actgagacac | ggcccagact | cctacgggag | gcagcagtag | 360 |
| ggaatcttcg | gcaatggacg | gaagtctgac | cgagcaacgc | cgcgtgagtg | aagaaggttt | 420 |
| tcggatcgta | aagctctgtt | gtaagagaag | aacgagtgtg | agagtggaaa | gttcacactg | 480 |
| tgacggtatc | ttaccagaaa | gggacggcta | actacgtgcc | agcagccgcg | gtaatacgta | 540 |
| ggtcccgagc | gttgtccgga | tttattgggc | gtaaagcgag | cgcaggcggt | tagataagtc | 600 |
| tgaagttaaa | ggctgtggct | taaccatagt | acgctttgga | aactgtttaa | cttgagtgca | 660 |
| agaggggaga | gtggaattcc | atgtgtagcg | gtgaaatgcg | tagatatatg | gaggaacacc | 720 |
| ggtggcgaaa | gcggctctct | ggcttgtaac | tgacgctgag | gctcgaaagc | gtggggagca | 780 |
| aacaggatta | gataccctgg | tagtccacgc | cgtaaacgat | gagtgctagg | tgttagaccc | 840 |
| tttccggggt | ttagtgccgc | agctaacgca | ttaagcactc | cgcctgggga | gtacgaccgc | 900 |
| aaggttgaaa | ctcaaaggaa | ttgacggggg | cccgcacaag | cggtggagca | tgtggtttaa | 960 |
| ttcgaagcaa | cgcgaagaac | cttaccaggt | cttgacatcc | ctctgaccgc | tctagagata | 1020 |
| gagttttcct | tcgggacaga | ggtgacaggt | ggtgcatggt | tgtcgtcagc | tcgtgtcgtg | 1080 |
| agatgttggg | ttaagtcccg | caacgagcgc | aacccctatt | gttagttgcc | atcatttagt | 1140 |
| tgggcactct | agcgagactg | ccggtaataa | accggaggaa | ggtggggatg | acgtcaaatc | 1200 |
| atcatgcccc | ttatgacctg | ggctacacac | gtgctacaat | ggctggtaca | acgagtcgca | 1260 |
| agccggtgac | ggcaagctaa | tctcttaaag | ccagtctcag | ttcggattgt | aggctgcaac | 1320 |
| tcgcctacat | gaagtcggaa | tcgctagtaa | tcgcggatca | gcacgccgcg | gtgaatacgt | 1380 |
| tcccgggcct | tgtacacacc | gcccgtcaca | ccacgagagt | ttgtaacacc | cgaagtcggt | 1440 |
| gaggtaacct | tttaggagcc | agccgcctaa | ggtgggatag | atgattgggg | tgaagtcgta | 1500 |
| acaagtcagc | cgtttgggaa | | | | | 1520 |

COMPOSITION FOR STRENGTHENING SKIN BARRIER, MOISTURIZING SKIN OR ANTI-AGING

CROSS-REFERENCE TO RELATED APPLICATION

This application is based on and claims priority under 35 U.S.C. § 119 to Korean Patent Application No. 10-2020-0057823, filed on May 14, 2020, in the Korean Intellectual Property Office, the disclosure of which is incorporated by reference herein in its entirety.

INCORPORATION BY REFERENCE OF SEQUENCE LISTING

Applicant incorporates by reference the sequence listing material in the ASCII text file. The ASCII text file is named "U.S. 17113744 Sequence," with a date of creation of Feb. 15, 2021, and with a size of 2,355 bytes.

BACKGROUND

1. Field

The present disclosure relates to a composition for strengthening skin barrier, moisturizing skin or anti-aging.

2. Description of Related Art

The skin ecosystem provides a variety of habitats for microorganisms and a wide range of microorganisms occupy the skin ecosystem. It is known that these microorganisms establish a symbiotic relationship with their human hosts and exert many positive effects on the human hosts. The skin forms diverse types of habitats, such as invaginations, specified niches, etc., which help a wide range of microorganisms grow. Basically, the skin forms a physical barrier layer and offers protection against a potential threat from the external environment and toxic substances. The skin functions as an interface with the external environment and is colonized by a diverse collection of microorganisms (fungi, bacteria, viruses and small larvae). The microorganisms, which are adapted to the specified niches, prepare their habitats according to selection of physical or chemical functions. In general, the skin is cool and acidic and is maintained in a dry state. Structurally, the epidermis plays important roles in forming a skin barrier, resisting penetration by microorganisms and toxins, and retaining moisture. The outermost layer of the epidermis is composed of the stratum corneum. The epidermis forms a so-called "bric and mortar" structure, the skin tissue undergoes a continuous self-renewal process, and squames are constantly shed from the skin surface at the final stage of differentiation.

Probiotics, collectively referring to microorganisms which have beneficial effects on the human body, are microorganisms offering benefits to the human body. Most probiotics known to date are lactic acid bacteria. It has been reported that probiotics show efficacy through various beneficial effects on the human body, but there are few studies on a correlation between skin pathogens and skin.

The skin barrier consists of dead ketatinocytes and intercellular lipids and plays a key role in maintaining skin health as a skin protection layer that protects the skin against external stimuli and prevents evaporation of water through the skin. That is, the skin barrier prevents excessive loss of water from the body and entry of harmful substances such as chemicals or microorganisms. Keratinocyte envelopes constituting the surface of dead keratinocytes play an important role in the stability of intercellular lipids. Keratinocytes undergo differentiation to form a skin barrier through a cornification process. Functions of the skin barrier may be destroyed with aging or by external factors, and damages of the skin barrier may cause water loss of the skin and wrinkles.

Accordingly, the present inventors isolated and identified a novel strain of the genus *Streptococcus* from the skin of an adult, and confirmed the skin improving effect thereof, thereby completing the invention.

PRIOR ART DOCUMENTS

Patent Documents (Patent document 1) Korean patent registration No. 1914157

SUMMARY

Provided is a composition for strengthening skin barrier, moisturizing skin, enhancing skin elasticity or anti-aging, the composition comprising a novel strain, a lysate thereof or a culture product thereof.

Additional aspects will be set forth in part in the description which follows and, in part, will be apparent from the description, or may be learned by practice of the presented embodiments of the disclosure.

An aspect provides a *Streptococcus mitis* strain under accession No. KCCM12656P.

The strain may be a strain having a 16S rRNA sequence having at least about 98%, at least about 99%, at least about 99.5%, or at least about 99.9% sequence identity to SEQ ID NO. 1. The strain may be a strain having a 16S rRNA sequence of SEQ ID NO. 1.

The term "sequence identity" as used herein means the extent that amino acid residues or bases between two sequences are identical after aligning the two sequences so as to maximally coincide with each other over a given region of comparison. The sequence identity is a value measured by optimally aligning two sequences in a specific comparison region, and some sequences in the comparison region may be added or deleted, as compared to the reference sequence. A percentage of sequence identity may be calculated by comparing, for example, two optimally sequences over the entire comparison region, obtaining the number of positions at which identical amino acids or nucleic acids occur in both sequences to yield the number of matched positions, dividing the number of matched positions by the total number of positions in the comparison range (i.e., the range size), and multiplying the result by 100 to yield the percentage of sequence identity. The percentage of sequence identity may be determined by a known sequence comparison program, and examples thereof may include BLASTN (NCBI), CLC Main Workbench (CLC Bio), MegAlign™ (DNASTAR Inc), and so on.

The strain may have effects of improving skin conditions, improving skin cosmetic benefits, or preventing, alleviating or treating skin diseases. For example, the stain may have an effect of strengthening skin barriers, moisturizing skin, enhancing skin elasticity, anti-aging, or preventing, alleviating or treating skin diseases, or combinations of two or more thereof.

The strain may be a strain capable of producing Spermidine.

The strain may be an isolated strain. As used herein, the term "isolated" means being artificially isolated to be utilized, rather than being naturally present. The strain is artificially isolated to be deposited under the above accession number. The strain may be isolated from the skin of a human. The strain may be isolated from the facial skin of a human.

An aspect provides a lysate, a culture product, or an extract of a culture solution of a *Streptococcus mitis* strain under accession No. KCCM12656P.

The strain is the same as described above.

As used herein, the term "culture solution" may be interchangeably used with "culture product", "culture supernatant", "conditioned culture broth" or "conditioned medium" and may refer to all media including the strain obtained by culturing the *Streptococcus mitis* strain in a medium capable of supplying nutrients to the strain to grow or survive in a test tube for a predetermined period, a metabolite thereof, extra nutrients, and so on. In addition, the culture broth may mean a culture obtained by removing bacterial cells removed from a bacterial culture obtained by culturing the strain. Meanwhile, the culture liquid from which bacterial cells are removed may also be referred to as a "supernatant" and may be obtained by letting the culture undisturbed for a predetermined time and then taking only the upper layer liquid, except for portions deposited on the bottom layer, removing the bacterial cells through filtration, or removing the lower sediment by centrifuging the culture and taking only the upper liquid. The "bacterial cell" means a strain itself of the present disclosure, and includes a strain itself isolated from skin samples, etc. and sorted or a strain obtained by culturing the strain and isolated from the culture solution. The bacterial cell may be obtained by taking the portion deposited on the bottom layer by centrifuging the culture solution. Alternatively, since the culture solution is deposited on the lower layer due to gravity, the bacterial cell may be obtained by removing the upper liquid after letting the culture solution undisturbed for a predetermined time.

The culture solution may include a culture solution itself acquired by culturing the strain, a concentrate thereof, or a freeze-dried product thereof, or a culture supernatant acquired by removing the strain from the culture solution, a concentrate thereof, or a freeze-dried product thereof.

The culture product is not particularly limited so long as it is obtained by culturing the strain using the *Streptococcus mitis* culturing method widely known to those skilled in the art, and may be, for example, a culture product acquired by culturing in MRS media as tryptic soy media treated with tryptone.

The culturing may be performed at a temperature of 20 to 60° C., 20 to 55° C., 20 to 50° C., 20 to 45° C., 20 to 44° C., 20 to 43° C., 20 to 42° C., 20 to 41° C., or 20 to 40° C., more preferably at 20 to 42° C., but embodiments of the present disclosure are not limited thereto.

The culturing may be performed for 30 to 60 hours, 35 to 60 hours, 30 to 55 hours, 40 to 55 hours, 40 to 60 hours, 40 to 50 hours, 45 to 60 hours, 45 to 55 hours, or 45 to 50 hours, more preferably for 45 to 50 hours, but not limited thereto.

In a specific embodiment, the culture supernatant of the strain may be acquired by removing the strain by centrifuging or filtering the strain culture solution.

In another specific embodiment, the concentrate may be obtained by concentrating the culture itself or a supernatant which is obtained by centrifuging the culture or filtering the culture by using a filter.

A medium and culture conditions for culturing the *Streptococcus mitis* strain may be appropriately selected or modified by those skilled in the art.

The culture product may include materials of a variety of components capable of demonstrating skin barrier strengthening capability, and may specifically include Spermidine. Accordingly, the culture product may increase the expression of collagen and may be a primary cause of increasing the expression of genes related with strengthening of skin barriers.

As used herein, the term "lysate" may be interchangeably used with "crushed fluid" or "crushed product", and may mean a product obtained by crushing the cell wall of a strain itself using a chemical or physical force.

As used herein, the term "extract of culture solution" means a product extracted from the culture solution or a concentrate solution thereof, and may include an extract solution, a diluted solution or a concentrate solution of the extract solution, a dried product obtained by drying the extract solution, or a crude purified product or a purified product thereof, and a fraction thereof.

An aspect provides use of *Streptococcus mitis* strain under accession No. KCCM12656P, a lysate thereof, a culture product thereof, or an extract of the culture solution. Specifically, provided is a composition comprising the strain, a lysate thereof, a culture product thereof, or an extract of the culture solution.

The use of the strain may include improvement of skin conditions, improvement of skin cosmetic benefits, or prevention, alleviation or treatment of skin diseases. The use of the strain may include skin barrier strengthening, skin moisturization, skin elasticity enhancement, or anti-aging, or combinations of two of more thereof.

As used herein, the term "skin barrier strengthening" may mean all of the activities for enhancing functions of skin barriers, which are positioned on the outermost side of the skin to then prevent losses of water and nutrients.

As used herein, the term "skin moisturization" may mean all of the activities for retaining moisture in the skin or preventing loss of moisture. The skin moisturization may be an effect exerted by increasing the amount of moisture retained in the skin while suppressing the loss of moisture by strengthening the skin barrier function of the composition, but embodiments are not limited thereto.

As used herein, the term "skin elasticity enhancement" may mean all of the activities for increasing skin elasticity reduced due to aging or preventing skin elasticity from being lowered.

As used herein, the term "skin aging" refers to both tangible and intangible changes that appear on the skin with aging, and for example, decreased epidermal thickness, reduction in the number of dermal cells or blood vessels, reduced ability to repair DNA, decreased cell turnover, delayed wound healing, reduced skin barrier functions, reduced water retention in the epidermis, decreased sweat and sebum secretion, decreased vitamin D production, decreased physical damage defense, decreased chemical removal ability, decreased immune responsiveness, decreased sensory function, decreased temperature control, etc.

The strain or the culture thereof may be used for skin aging alleviation or anti-aging caused by exogenous or endogenous factors. The exogenous factors refer to many external factors, for example, ultraviolet rays (light), and the endogenous factors, also called chronological factors, refer to factors mainly occurring over time. That is, the skin aging specifically includes not only early aging caused by external stimuli such as UV, air pollution, cigarette smoke, chemicals, etc., but also natural aging occurring due to a reduction in skin cell proliferation with aging. The skin aging is a concept including all of wrinkles, loss of elasticity, saggy skin, dryness, etc. In addition, wrinkles include wrinkles caused by changes in the components constituting the skin tissue by stimulation of internal/external factors.

The aging may be photoaging. The term "photoaging" refers to a phenomenon induced by external environmental factors and one of the most typical factors include ultraviolet radiation. Ultraviolet radiation may bring about damages of biological components, such as protease activation, substrate protein strands breaks, or abnormal cross-linking, and repetition of such mechanism results in apparently prominent skin aging.

The anti-aging may be an effect externed by recovering skin barriers reduced with the progress of aging owing to the skin barrier strengthening effect of the composition, and thus increasing again the expression of factors for retaining skin barriers, which is reduced due to aging. The anti-aging may be an effect that may be obtained by the skin elasticity enhancing effect of the composition.

The "skin disease" may be a disease due to a damaged skin barrier function, or skin aging. The term "prevention" may include suppression of outbreak of a disease. The term "treatment" may include suppression, alleviation or removal of the progress of a disease.

The skin barrier function damage may mean all the changes appearing on the skin due to degradation or damage of the skin barrier function. For example, the skin barrier function damage may include increased skin wrinkles, dry skin, dermatitis, atopic dermatitis, allergic dermatitis, and acne.

The extract of the strain, a lysate thereof, a culture product thereof, or the extract of a culture solution may be included in an amount of 0.001 to 90% by weight, 0.01 to 90% by weight, 0.1 to 90% by weight, 0.1 to 85% by weight, 0.1 to 80% by weight, 0.2 to 90% by weight, 0.2 to 85% by weight, 0.2 to 80% by weight, 0.3 to 90% by weight, 0.3 to 85% by weight, 0.3 to 80% by weight, 0.4 to 90% by weight, 0.4 to 85% by weight, 0.4 to 80% by weight, 0.5 to 90% by weight, 0.5 to 85% by weight, 0.5 to 80% by weight, 0.6 to 90% by weight, 0.6 to 85% by weight, or 0.6 to 80% by weight, more preferably 0.5 to 80% by weight, based on the total weight of the composition, but embodiments are not limited thereto.

The expression, "comprising as an active ingredient" means that the strain of the present disclosure, a lysate thereof or a culture product thereof, or an extract of the culture may be added enough to exhibit the aforementioned effects, and encompass being formulated in a variety of forms by adding various ingredients for drug delivery and stabilization.

The composition may be in a liquid state or a dry state. In a specific embodiment, the composition may be in a dry powder state.

As the drying method for preparing the composition in a dry state, any method that is commonly used in the art may be used without any particular limitation. Non-limiting examples of the drying method may include an air-drying method, a natural drying method, a spray-drying method, and a freeze-drying method. These methods may be used alone or in combination with at least two methods.

The composition may comprise an additive in an effective amount enough to reduce deterioration of the strain, a lysate thereof or a culture product thereof. The additive may include, for example, a binder, but is not limited thereto.

The composition may further comprise a cosmetically or pharmaceutically acceptable carrier. The composition may be formulated with the carrier to be provided as a cosmetic, a medicine or a food additive. Therefore, the composition may be a cosmetic composition, a pharmaceutical composition, or a health functional food composition.

According to an aspect, the composition may be a cosmetic composition.

The cosmetic composition may include components commonly used in cosmetic compositions, for example, common additives, such as an antioxidant, a stabilizer, a solubilizer, vitamins, a pigment, or a fragrance, and carriers.

Examples of products to which the composition may be added may include cosmetics, such as astringent, softener, nutrient lotion, various kinds of creams, essence, face mask, or makeup foundation, cleansers, facial cleanser, soap, hair-care treatment, or cosmetic solution, but are not limited thereto.

Specific examples of the formulations of the cosmetic composition may include skin lotion, skin softener, skin toner, astringent, lotion, milk lotion, moisturizing lotion, nutrient lotion, massage cream, nutrient cream, moisture cream, hand cream, essence, nutrient essence, face mask, soap, shampoo, foaming cleanser, lotion type cleanser, cream type cleanser, body lotion, body cleanser, emulsion, lipstick, makeup base, makeup foundation, press powder, loose powder, and eye shadow.

In an aspect, the composition may be a pharmaceutical composition.

The pharmaceutical composition may be formulated as a formulation for oral or parenteral administration, and the formulation for oral administration may be a powder, granules, a tablet, a capsule, a suspension, an emulsion, a syrup, or an aerosol, a formulation for external use, a suppository, and a sterile injection solution, but is not limited thereto.

Examples of the carrier, excipient and diluent which can be contained in the pharmaceutical composition may include lactose, dextrose, sucrose, dextrin, maltodextrin, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil, but are not limited thereto. When the composition is formulated, the formulation may be formulated using a commonly used diluent or excipient, such as a filter, a thickener, a binder, a swelling agent, a disintegrating agent, or a surfactant, but is not limited thereto.

Examples of a solid formulation for oral administration may include a tablet, pills, a powder, granules, and a capsule, but are not limited thereto. However, the solid formulation may be formulated by mixing at least one excipient, such as starch, calcium carbonate, sucrose or lactose, or gelatin, with the compound. Also, in addition to the simple excipient, lubricants, such as magnesium stearate or talc, may also be used.

A liquid formulation for oral administration may be a suspension, an oral liquid, an emulsion, or a syrup, and may include various excipients in addition to a commonly used diluent, such as water or liquid paraffin, including, for example a wetting agent, a sweetener, a fragrance, or a preservative. A formulation for parenteral administration may include a sterilized aqueous solution, a nonaqueous solution, a suspension, an emulsion, a freeze-dried formulation and a suppository. For the nonaqueous solution or the suspension, propylene glycol, polyethylene glycol, a vegetable oil such as olive oil, an injectable ester such as ethyl oleate, etc. may be used. As a base of the suppository, witepsol, macrogol, tween 61, cocoa butter, laurin butter, glycerogelatin, etc. may be used.

In an aspect, the composition may be a health functional food composition.

The term "health functional food" used herein refers to a food prepared and processed using raw materials or ingredients having useful functions in the human body in accordance with Law No. 6727 on Korea Health Functional Foods, and means that the structure and function of the human body is ingested for the purpose of obtaining nutritional control or physiological effects and other useful effects for health use.

The health functional food may include common food additives, and, unless stipulated otherwise, the suitability thereof may be determined by the regulations and standards on relevant food items approved by the Ministry of Food and Drug Safety in accordance with the general rules and general testing methods of the Food Additive Code.

Examples of the food items included in Korean Food Additives Codex may include chemical compositions such as ketones, glycine, calcium citrate, nicotinic acid, or cinnamic acid; natural additives such as a persimmon pigment, a licorice extract, crystalline cellulose, a kaoliang pigment, or guar gum; and mixed formulations such as L-sodium glutamic acid formulations, alkali additives for noodles, preservative formulations, or tar pigment formulations, but are not limited thereto.

For example, the tablet-type health functional food may be prepared by granulating a mixture including the composition mixed with an excipient, a binder, a disintegrating agent and other additives using a common method, and adding a lubricant, etc. to then be compressed, or directly compressing the mixture. In addition, the tablet-type health functional food may contain a flavoring agent as needed.

Among capsule-type health functional foods, a hard-capsule formulation may be prepared by filling a common hard capsule with a mixture including the composition mixed with an additive, such as an excipient, and a soft-capsule formulation may be prepared by filling a capsule base, such as gelatin, with a mixture including the composition mixed with an additive such as an excipient. The soft-capsule formulation may contain a plasticizer such as glycerin or sorbitol, a coloring agent, or a preservative, as needed.

The pill-type health functional food may be prepared by forming a mixture including the composition mixed with an excipient, a binder, or a disintegrating agent using a method known in the art, and may be coated with white sugar or other coating agents, as needed, or may be surface-coated with a material such as starch or talc.

The granule-type health functional food may be prepared by forming a mixture including the composition mixed with an excipient, a binder, or a disintegrating agent into granules using a method known in the art, and may include a coloring agent or a flavoring agent, as needed.

The health functional food may include beverages, meats, chocolates, foods, and confectionaries. The health functional food may include pizzas, ramens, other noodles, gums, ice creams, alcoholic beverages, multi-vitamins, and supplementary health foods.

In an aspect, the composition may be a composition for skin external use.

In the present disclosure, the composition for external use may be a cream, a gel, an ointment, a skin emulsifier, a skin suspension, a transdermal patch, a drug-containing bandage, a lotion, or a combination thereof. The composition for skin external use may be appropriately blended with components used in compositions for skin external use, such as common cosmetics or medicines, for example, an aqueous component, an oily component, a powder component, alcohols, a moisturizer, a thickener, a UV absorber, a whitening agent, a preservative, an antioxidant, a surfactant, a fragrance, a pigment, a variety of skin nutrients, or a combination thereof as needed. The composition for skin external use may be appropriately blended with a metal sequestering agent such as disodium edetate, trisodium edetate, sodium citrate, sodium polyphosphate, sodium metaphosphate, gluconic acid, etc., caffeine, tannin, verapamil, a licorice extract, glabridin, a hot water extract of fruits of Calin, various herbal medicines, tocopheryl acetate, glycyrrhizic acid, tranexamic acid and a derivative or salt thereof, vitamin C, magnesium ascorbyl phosphate, ascorbic acid glucoside, arbutin, Kojic acid, or sugars such as glucose, fructose, or treharose.

In an aspect, provided is a method for improving skin conditions of a subject, the method including administering an effective amount of a composition comprising a *Streptococcus mitis* strain under accession No. KCCM12656P, a lysate thereof or a culture product thereof to a subject in need thereof.

The composition may be a composition for a cosmetic composition, a pharmaceutical composition, a health functional food composition, or a skin external use.

The improvement of skin conditions may include skin barrier strengthening, skin moisturization, skin elasticity enhancement, or anti-aging, or combinations of two of more thereof.

The terms "administering", "introducing", and "transplanting" may be interchangeably used, and may mean placement of a composition according to a specific embodiment into a subject using a method or a pathway for causing at least partial localization on a desired portion.

The administration may be performed using a method known in the art. The administration may include directly administering the composition to a subject by an arbitrary means through a route, such as intravenous administration, subcutaneous administration, oral administration, transdermal administration, transmucosal administration, intranasal administration, intratracheal administration, or subcutaneous administration. The administration may include applying the composition to the skin. The administration may be systemic administration or topical administration.

The subject may be mammals, for example, humans, cattle, horses, pigs, dogs, sheep, goats, or cats. The subject may be a subject in need of improving skin conditions, for example, skin barrier strengthening, skin moisturization, skin elasticity enhancement, or anti-aging.

The administration may be administering 0.1 mg to 1,000 mg of the composition according to a specific embodiment, for example, 0.1 mg to 500 mg, 0.1 mg to 100 mg, 0.1 mg to 50 mg, 0.1 mg to 25 mg, 1 mg to 1,000 mg, 1 mg to 500 mg, 1 mg to 100 mg, 1 mg to 50 mg, 1 mg to 25 mg, 5 mg to 1,000 mg, 5 mg to 500 mg, 5 mg to 100 mg, 5 mg to 50 mg, 5 mg to 25 mg, 10 mg to 1,000 mg, 10 mg to 500 mg, 10 mg to 100 mg, 10 mg to 50 mg, or 10 mg to 25 mg, to each subject per day. The administration dose may be differently prescribed depending on various factors, such as the formulating method, the manner of administration, the age, body weight, sex, or morbidity of a patient, the diet, the time and route of administration, the excretion rate, and response sensitivity, and may be appropriately controlled by those skilled in the art in consideration of these factors. The number of times of administration may be once a day or twice or more within the range of clinically tolerable side effects, the site of administration may be one site or two or more sites, and a total number of administration days may be one day or may be extended up to 30 days at 2- to 5-day intervals. When necessary, the same treatment may be repeated after a proper period. The same doses/kg body weight may be administered to animals other than humans, or the converted dose by, for example, a volume ratio (e.g., a mean value) of animal and human organs (heart, etc.), may be administered.

In an aspect, provided is use of a *Streptococcus mitis* strain under accession No. KCCM12656P, a lysate thereof or a culture product thereof, for preparing a composition for improving skin conditions.

The improving of skin conditions may include skin barrier strengthening, skin moisturization, skin elasticity enhancement, or anti-aging, or combinations of two of more thereof.

The composition may be a cosmetic composition, a pharmaceutical composition, or a composition for skin external use.

Details of the strain, the lysate and the culture product are the same as described above.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 1A shows relative abundance at genus level in facial skin microbiomes, in which top 5 geni are presented (where F denotes family).

FIG. 1B shows box plots representing numbers of reads of the genus *Streptococcus* in old and young individuals.

FIG. 1C shows taxonomic plots of LDA scores obtained from LEfSe, showing microbiota significantly differently sequenced between old and young individuals (|LDA scores|>3.5; g denotes genus, and s denotes species).

FIG. 1D shows box plots representing elasticity indices according to each individual's age.

FIG. 1E shows *Streptococcus* leads relative to the elasticity ratio in old and young individuals, in which Pearson's correlation test was used in calculating statistical significances.

FIG. 2A shows relative mRNA expression levels of collagen-related genes in HDF, which are essential to elasticity.

FIG. 2B shows relative mRNA expression levels of elastic fiber-related genes in HDF.

FIG. 2C shows relative mRNA expression levels of tight junction-related genes in HDF, which are essential to skin barrier function and moisture.

FIG. 2D shows relative mRNA expression levels of lipid barrier-related genes in HDF. The values herein are related to β-actin and indicate (mean±standard deviation) values. Statistical significances were calculated using student's two-tailed t-test (*$p<0.01$, **$p<0.001$).

FIG. 2E shows Nile Red lipid staining results of HEK treated with different *Streptococcus* culture media. The microscopic images were photographed at magnification of 100×.

FIG. 3A, FIG. 3B, FIG. 3C, FIG. 3D, FIG. 3E, and FIG. 3F show genomic characteristic and analysis results of gene ontology (GO) terms and pathways of the genus *Streptococcus*.

FIG. 3A shows the average nucleotide identity (ANI) among four *Streptococcus* candidates.

FIG. 3B shows the procedure of selecting genes which are not included in *Streptococcus thermophilus* but are included in *Streptococcus pneumoniae*, *Streptococcus infantis* and *Streptococcus mitis*.

FIGS. 3C to 3E show GO terms for biological pathways of the significant genes from close ANI score-candidates (FIG. 3C: *Streptococcus infantis*; FIG. 3D: *Streptococcus pneumoniae*; and FIG. 3E: *Streptococcus mitis*).

FIG. 3F shows biosynthesis processes of *Streptococcus pneumoniae*, *Streptococcus infantis* and *Streptococcus mitis*.

FIG. 4B: 1000-fold diluted *Streptococcus infantis* St solution; FIG. 4C: 1000-fold diluted *Streptococcus pneumoniae* St solution; FIG. 4D: 1000-fold diluted *Streptococcus mitis* St solution; and FIG. 4E: 1000-fold diluted *Streptococcus thermophilus* St solution).

FIGS. 5A to 5G are box plots showing skin parameters of old and young individuals for control group and St emulsion treated groups, in which FIG. 5A shows box plots for elasticity, FIG. 5B shows box plots for TEWL, FIG. 5C shows box plots for moisture, FIG. 5D shows box plots for gloss, and FIG. 5E shows box plots for desquamation.

FIG. 5F shows results of direct observation for cheek surface desquamation in candidates S01 and S05 at day 0 and day 28 (4 weeks) after treatment of St emulsion.

FIG. 5G shows increases in candidate *Streptococcus* and *Streptococcus infantis* 28 days (4 weeks) after treatment of St emulsion. Statistical calculation for paired comparison was performed by Wilcoxon signed-rank test, and inter-comparison was performed by Wilcoxon-Mann-Whitney test (A.U: arbitrary unit; DSC: diffuse scattering correction; D.I: desquamation index). The white area indicates keratinocytes, and the area was measured using ImageJ. The microscopic images were photographed at magnification of 20×.

FIG. 6A and FIG. 6B show microbe compositions of skin samples in old and young individuals at phylum level.

FIG. 6A shows phylum constituents of young and old individuals, indicating relative abundance (%) for each individual.

FIG. 6B shows distributions of top 5 abundant phyla in all individuals, in which the y axis indicates the number of reads for each phylum. Mann-Whitney U test was used in calculating statistical significances.

FIG. 7A, FIG. 7B, and FIG. 7C show microbial distances and compositions of skin microbiota in old and young individuals at genus level.

FIG. 7A shows beta diversity of skin microbiota in old and young candidates, in which the left view indicates Bray-Curtis distance, and the right view indicates weighted UniFrac distance. Statistical calculation was performed by PERMANOVA having 999 permutations.

FIG. 7B shows correlations between age and *Streptococcus* in old and young individuals, in which Pearson's correlation test was used in calculating statistical significances.

FIG. 7C shows distributions of top 5 geni in old and young individuals, in which F means family, and the y axis means the number of reads for each genus. Mann-Whitney U test was used in in calculating statistical significances.

FIG. 8A shows phylum composition in individuals with low and high elasticity.

FIG. 8B shows beta diversity of skin microbiota according to elasticity, in which the upper view indicates Bray-Curtis distance, and the lower view indicates weighted UniFrac distance. Statistical calculation was performed by PERMANOVA having 999 sequences.

FIGS. 8C and 8D show numbers of reads of *Streptococcus* and *Streptococcus infantis*, respectively, in which for comparison of abundance values, statistical significances were calculated using Mann-Whitney U test.

FIG. 9A shows beta diversity of skin microbiota according to different skin surface conditions, in which bad (5), normal (27), rough (3), and smooth (17) conditions are shown. The left view indicates Bray-Curtis distance, and the right view indicates weighted UniFrac distance.

FIG. 9B shows distributions of *Streptococcus* (left) and *Streptococcus infantis* (right) related to various face conditions.

FIG. 9C shows beta diversity of skin microbiota according to different skin moisture conditions, in which dry (25), extremely dry (4), and normal (23) conditions are shown. The left view indicates Bray-Curtis distance, and the right view indicates weighted UniFrac distance.

FIG. 9D shows box plots for explaining distributions of *Streptococcus* (left) and *Streptococcus infantis* (right) according to various facial water conditions, in which statistical calculation of the beta diversity was performed by PERMANOVA having 999 permutations (NS: non-significant; p<0.01; *p<0.001). For abundance comparison, statistical significances were calculated using Mann-Whitney U test.

FIG. 10A shows the result of toxicity test using *Streptococcus* (St) solutions of HDF (left) and HEK (right), in which the volume of the St solution for each treatment was 10% of a total volume of media. The values herein indicate (mean±standard deviation) values.

FIG. 10B shows the result of screening test for selecting the St solution having the optimal concentration for treating HDF, in which mRNA levels of COL1A1, COL3A1, ELN and FBN1 were used as read values. The values herein are related to β-actin and indicate (mean±standard deviation) values. Student's two-tailed t-test was used in calculating statistical significances (*p<0.01, **p<0.001).

FIG. 10C shows medium treatment effects on mRNA levels of COL1A1, COL3A1, ELN and FBN1.

FIG. 10D shows effects of *Streptococcus thermophilus* culture supernatant treatment on mRNA levels of DSC2, FLG, GBA and ABCA12, in which the values indicate (mean±standard deviation) values (**p<0.01).

FIG. 11A shows epidermis thicknesses of a non-treated group, FIG. 11B shows epidermis thicknesses of a group treated with 1 ppm Poly I:C, FIG. 11C shows epidermis thicknesses of a group treated with 1 ppm Poly I:C and *Streptococcus infantis* supernatant, FIG. 11D shows epidermis thicknesses of a group treated with 1 ppm Poly I:C and *Streptococcus pneumoniae* supernatant, and FIG. 11E shows epidermis thicknesses of a group treated with 1 ppm Poly I:C and *Streptococcus mitis* supernatant. The microscopic images were photographed at magnification of 100×.

FIG. 12A and FIG. 12B show GO term analysis of the *Streptococcus thermophilus*, in which FIG. 12A shows COGs of the respective *Streptococcus* candidates based on the entire genome analysis, and FIG. 12B summarizes GO terms of biological pathways for the *Streptococcus thermophilus*.

FIGS. 14A to 14E shows elasticity, TEWL, moisture, gloss and skin desquamation on day 0 and day 28 after applying control emulsions.

FIG. 14F shows skin brightness. Left, control emulsion; center, St emulsion; right, boxplot of control emulsion versus St emulsion.

FIG. 14G shows skin transparency. Left, control emulsion; center, St emulsion; right, boxplot of control emulsion versus St emulsion. Statistical calculation for paired comparison was performed by Wilcoxon signed-rank test, and inter-comparison was performed by Wilcoxon-Mann-Whitney test (A.U: arbitrary unit; DSC; diffuse scattering correction; and D.I: desquamation index)

DETAILED DESCRIPTION

Figure 1A:
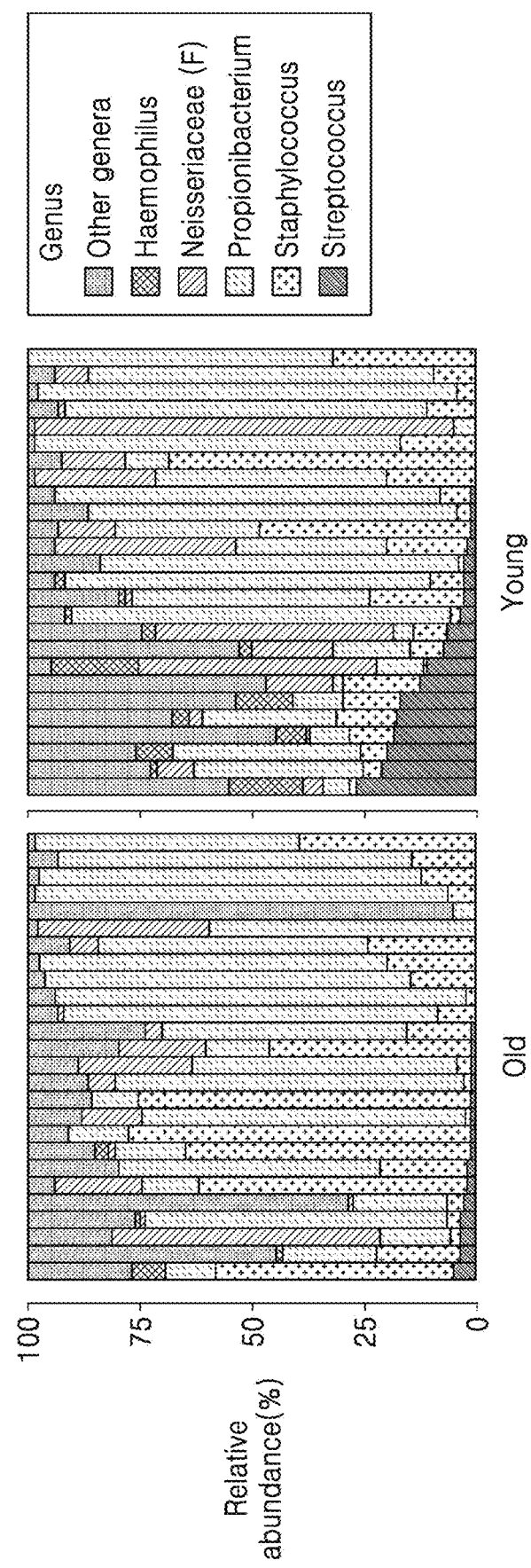
FIG. 1A, FIG. 1B, FIG. 1C, FIG. 1D, and FIG. 1E show a comparison of skin microbiota of old and young individuals.

Reference will now be made in detail to embodiments, examples of which are illustrated in the accompanying drawings, wherein like reference numerals refer to like elements throughout.

In this regard, the present embodiments may have different forms and should not be construed as being limited to the descriptions set forth herein.

Accordingly, the embodiments are merely described below, by referring to the figures, to explain aspects of the present description.

As used herein, the term "and/or" includes any and all combinations of one or more of the associated listed items.

Expressions such as "at least one of," when preceding a list of elements, modify the entire list of elements and do not modify the individual elements of the list.

Hereinafter, the present disclosure will be described in further detail with reference to the following examples.

Experimental Methods

1. Collection and Preparation of Microorganism Samples for Microbiome Analysis

Microbiota samples were collected from 26 old volunteers and 26 young volunteers who participated in researches using a sterilized tape (Elizabeth Pack; Cell Lab, Korea). Subsequently, the tape was immersed in liquid tryptic soy broth (TBS) media (Benton Dickinson, Franklin Lakes, N.J., USA) according to manufacturer's recommendations. After bacteria were grown at 37° C. for 48 hours, the media were centrifuged at 6000 rpm for 10 minutes. The collected pellets were subjected to a Quick-DNA™ fungi/bacteria miniprep kit (Zymo Research, Orange, Calif., USA) according to manufacturer's recommendations, and microorganism DNAs were extracted. DNA purity and quantity were estimated using a spectrophotometer NanoDrop One (Thermo Scientific, Waltham, Mass., USA).

2. 16S rRNA PCR Amplification and Sequencing for Microbiome Analysis

V3-V4 regions of bacteria 16S rRNA genes were amplified using primers with adapter overhang sequence added thereto, as listed in Table 1, according to Illumina 16S Metagenomic Sequencing Library Preparation Guidelines (Illumina, San Diego, Calif., USA).

TABLE 1

| Primer | Sequence (5'→3') |
|---|---|
| Forward | TCGTCGGCAGCGTCAGATGTGTATAAGAGACAGCCTACGGG NGGCWGCAG |
| Reverse | GTCTCGTGGGCTCGGAGATGTGTATAAGAGACAGGACTACH VGGGTATCTAATCC |

PCR was performed with 25 µL reaction volume, including 2 µL genomic DNA (10 ng/µL), 0.5 µL each primer (10 µM), 12.5 µL 2×KAPA HiFi HotStart ReadyMix (Kapa Biosystems, MA, Wilmington, Mass.) and 9.5 µL distilled water. PCR conditions were as follows: initial denaturing at 95° C. for 3 minutes; 25 cycles including denaturing at 95° C. for 30 seconds, annealing at 55° C. for 30 seconds, and extension at 72° C. for 30 seconds; and final extension at 72° C. for 5 minutes. PCR products were purified using AMPure XP Beads (Beckman Coulter, Brea, Calif., USA) according to manufacturer's protocol. Attachment of dual-index sequences and Illumina adapters was performed using 5 µL PCR product, 5 µL Illumina Nextera XT index primer 1 (N7xx), 5 µL Nextera XT index primer 2 (S5xx), 25 µL 2×KAPA HiFi HotStart Ready Mix, and 10 µL nuclease-free water. Thermocycling is performed using the following protocol: 95° C. for 3 minutes; 8 cycles including 95° C. for 30 seconds, 55° C. for 30 seconds, and 72° C. for 30 seconds; and final extension at 72° C. for 5 minutes. PCR products were purified using AMPure XP beads, and quality control for the 16S bacteria genome library was performed using Agilent Technologies 2100 Bioanalyzer (Agilent, Santa Clara, Calif., USA). The library was normalized to 2×250 bp paired-end sequencing according to the standard Illumina sequencing protocol for sequencing in the MiSeq platform (Illumina), and then pooled.

3. Microbiome Analysis

The quality of raw sequence reads was analyzed using FastQC. Illumina adapter sequences of Paired-end reads were removed using cutadapt version 2.2. Then, trimmed sequences were processed using QIIME2 version 2019.4. In short, reads were assigned to the respective samples according to intrinsic indices, and read pairs of original DNA fragments were merged using an import tool in QIIME2. Quality control and trimming were performed on forward and reverse reads so as to have 230 bp and 220 bp sequences, respectively. In order to remove poor-quality bases from read terminals, DADA2 software package was used. To remove chimera from FASTAQ files, a consensus method implemented in DADA2 was used. The beta diversity was compared through principal coordinate analysis using Bray-Curtis weighted UniFrac metric. To evaluate inter-group similarity, permutational multivariate analysis of variance (PERMANOVA) having 999 permutations was used. Taxonomic annotation was performed by mapping the following primers to training reference sets and extracting V3-V4 regions using GreenGenes version 13.8.

TABLE 2

| Primer | Sequence (5'→3') |
|---|---|
| Forward | CCTACGGGNGGCWGCAG |
| Reverse | GACTACHVGGGTATCTAATCC |

Differential characteristics at inter-group species level were identified by performing linear discriminant effect size analysis (LEfSe) based on linear discriminant analysis (LDA) scores using Galaxy implementation. Statistical plotting and calculation were generated at R studio using ggplot2 package.

4. Isolation, Discrimination and Deposition of *Streptococcus* from Face

Experimental subject's face was washed using sterile water, and the sterile water was sprayed to solid TSA media. Single colonies were collected and subjected to stationary culture in a liquid TSB media at 37° C. for 72 hours. Next, the respective samples were centrifuged at 6000 rpm for 30 minutes, and pellets were collected. Then, microbe DNAs were extracted using a Quick-DNA™ fungi/bacteria miniprep kit according to manufacturer's recommendations. The purity and quantity of DNAs were estimated using a Nano-Drop One spectrophotometer. Bacteria 16S rRNA genes were amplified using the following primers.

TABLE 3

| Primer | Sequence (5'→3') |
|---|---|
| Forward | AGAGTTTGATCMTGGCTCAG |
| Reverse | TACGGYTACCTTGTTACGACTT |

PCR was performed using 25 µL reaction volume containing 2 µL genomic DNA (10 ng/µL), 0.5 L each primer (10 µM), 12.5 µL 2×KAPA HiFi HotStart ReadyMix (Kapa Biosystems, MA, Wilmington, Mass.) and 9.5 µL distilled water. PCR conditions were as follows: initial denaturing at 95° C. for 3 minutes; 30 cycles of denaturing at 95° C. for 1 minute, annealing at 55° C. for 1 minute, and extension at 75° C. for 90 seconds; and final extension at 72° C. for 8 minutes. PCR products were sequenced using ABI-3730XL DNA sequencer (Applied Biosystems, Foster City, Calif., USA), and sequence reads were identified using NCBI microbe nucleotide BLAST having mega-BLAST. Under the provisions of the Budapest Treaty on the International Recognition of the Deposit of Microorganisms for the Purpose of Patent Procedure, the strains of the genus *Streptococcus*, *Streptococcus pneumoniae*, was deposited on Korean Culture Center of Microorganisms (KCCM) on Apr. 3, 2017 as a Deposit No. KCCM12005P. *Streptococcus infantis* was deposited on KCCM, with an address of Yurim B/D, 45, Hongjenae-2ga-gil, Seodaemun-gu, Seoul, Korea, 03641, on Dec. 18, 2019 as a Deposit No. KCCM12642P, and *Streptococcus mitis* was deposited on KCCM on Jan. 15, 2020 as a Deposit No. KCCM12656P.

5. Cell Culturing and Processing

HDF and HEK were purchased from PromoCell (Heidelberg, Germany). HDF and HEK were cultured in a fibroblast growth medium 2 with a PromoCell supplement mix and a keratinocyte growth medium 2 with a supplement mix, respectively. For processing *Streptococcus* culture supernatant (St solution), cells were seeded in 6-well plates to 80% confluence and cultured at 37° C. under a 5% carbon dioxide environment. After 24 hours, the cells were washed once using PBS, 10% conditioned media were added to the cells with supplement-free media, and then cultured for 24 hours.

6. Analysis of Cell Viability

HDF and HEK were seeded in 48-well plates and then cultured in 1 mL complete media for 24 hours, 10% *Streptococcus* culture supernatant was added thereto, and then additionally cultured for 72 hours. The cells were washed once using PBS, 3-(4, 5-dimethylthiazol-2-yl)-2, 5-diphenyltetrazolium bromide (MTT) solution was added to each well, followed by culturing for 4 hours. Next, the media were discarded, and dimethyl sulfoxide was added for dissolving formazan crystals. Optical densities were measured at 570 nm using a microplate reader and then normalized for a non-treated control group.

7. RNA Isolation and Real-time PCR

Total RNA was isolated from the cells using TRIzol reagent (TaKaRa, Shiga, Japan) according to manufacturer's instructions. cDNA was synthesized from 1 μg of total RNA under the following reaction conditions using a Reverse Transcriptase premix (Elpis-biotech, Daejeon, Republic of Korea): reactions at 45° C. for 45 minutes and at 95° C. for 5 minutes. Gene expression was quantified using real-time PCR, and data were analyzed using StepOne Plus™ software (Applied Biosystems). Real-time PCR amplification was performed using SYBR Green PCR Master Mix with premixed ROX (Applied Biosystems). The following primer pairs (Bioneer, Daejeon, Korea) were used in reactions performed by an ABI 7300 cycler according to manufacturer's protocol.

TABLE 4

| Gene | Primer | Sequence (5'→3') |
|---|---|---|
| β-actin | Forward | GGCCATCTCTTGCTCGAAGT |
|  | Reverse | GACACCTTCAACACCCCAGC |
| COL1A1 | Forward | GAGGGCCAAGACGAAGACATC |
|  | Reverse | CAGATCACGTCATCGCACAAC |
| COL3A1 | Forward | TGGAGGATGGTTGCACGAAA |
|  | Reverse | ACAGCCTTGCGTGTTCGATA |
| ELN | Forward | CACCTTGCCCTTGTAGAATCCA |
|  | Reverse | CCATGACAGGTCAACCAGGTT |
| FBN1 | Forward | AATGTCAGACGAAGCCAGGG |
|  | Reverse | GATTTGGTGACGGGGTTCCT |
| DSC2 | Forward | AGTGTGAGTTTGTTCATCACAGGTC |
|  | Reverse | CCATGGCCTCACAGCCTTTA |
| GBA | Forward | GCTAGGCTCCTGGGATCGAG |
|  | Reverse | GTTCAGGGCAAGGTTCCAGTCA |
| FLG | Forward | AGTGCACTCAGGGGGCTCACA |
|  | Reverse | CCGGCTTGGCCGTAATGTGT |
| ABCA12 | Forward | ACAGGAATGGCCTTCATCAC |
|  | Reverse | AACATGGTGCCCTGAGAAAC |

(COL1A1, collagen type I alpha 1 chain; COL3A1, collagen type 3 alpha 1 chain; ELN, elastin; FBN, fibrillin; DSC2, desmocollin 2; FLG, filaggrin; GBA, glucosylceramidase beta; ABCA12, ATP binding cassette subfamily A member 12) Reaction conditions were as follows: starting at 50° C. for 2 minutes and at 95° C. for 10 minutes; and 40 cycles of 10 seconds at 95° C. and 1 minute at 60° C. β-actin was used as an internal control group.

8. Nile Red Staining for SC Neutral Lipids

For cellular lipid staining analysis, HEK cells were seeded in 6-well plates. After 24 hours, 10% *Streptococcus* culture solution was added to the cells, and the resultant cells were further cultured for 24 hours. After washing, neutral lipids in HEK were quantified using Nile Red staining. A Nile Red (1 mg/mL) stock solution in acetone was prepared and stored at −20° C. in dark room conditions. 1 μl stock solution was added to 1 mL PBS, and 500 μl of the mixture was dispensed to each well to thus prepare a new staining solution. 10 minutes after storing in dark, room temperature conditions, the cells were identified using a fluorescence microscope (Axio Observer Z1; Carl Jeniss, Jena, Germany). The neutral lipid was visualized as a red fluorescent structure.

9. Normal Human 3D Skin Models

Normal human 3D skin model at full thickness, including normal human keratinocytes and fibroblasts (Epiderm-FT; MatTek Co., Ashland, Mass., USA) were cultured. Tissues were transferred to a 6-well plate and then cultured overnight in DMEM (MatTek Co., MA, USA), including 5 μg/mL gentamicin B (MatTek Co., MA, USA), 0.25 μg/mL amphotericin B (MatTek Co., MA, USA), and other growth factors, under 37° C. 5% carbon dioxide conditions.

10. Aging Induction and Sample Processing

The normal human 3D skin models were stabilized in 6-well plates and cultured overnight at 37° C. under 5% carbon dioxide environment. The 3D skin models were treated with polyinosinic-polycytidylic acid (poly I:C) (1 ppm), and then tissues were treated with St solution.

11. Genome Analysis

DNA sequencing was performed using an Illumina HiSeq 4000 sequencer having a length of 151 bp paired-end reads. The library was manufactured using a TruSeq nano DNA kit (Illumina). The reads were trimmed by trimmomatic-0.38 and assembled using SPAdes v3.9.060. Assembled fragments shorter 100 nucleotides were filtered using a pearl script (removesmalls.pl). Gene prediction was performed on the assembled and filtered genomes using Prokka v1.1361. Common genes among *Streptococcus* species were detected using COGs. Annotation networks functionally grouped for selected genes were constructed using Cytoscape plug-in ClueGO v2.5.462. GO terms functionally related to biological pathways of *E. coli*. (version: Nov. 18, 2016) were grouped on the basis of the network specificity ranging from 4 to 10 and the kappa score exceeding 0.4. Statistical significances were calculated using a two-sided hypergeometric function test, and false discovery rate was corrected using Benjamini-Hochberg correction technique.

12. Quantitative Analysis of Spermidine in St Solution

Each $1 \times 10^8$ CFU/ml of TSB medium (control group) and St solution was collected and then centrifuged at 6000 rpm for 10 minutes. Next, supernatants were filtered (0.22 μm membrane filter, Woongki Science Co., Ltd., Seoul, Korea), and each 10 μl of the filtered solutions was injected into Ultimate 3000 (Thermo Fisher Scientific Inc., Sunnyvale, Calif., USA). The column used was Thermo Hypersil Gold column (50×2.1 mm, 1.9 μm, Thermo Fisher Scientific Inc.). A moving bed (solvent A: 0.1% heptafluorobutyric acid (HFBA) in water; and solvent B: HFBA in acetonitrile) was eluted at a flow rate of 0.4 mL/min with an elution gradient of the following solvent B: 10% (0.01 min)→10% (0.5 min)→100% (5 min)→100% (6.5 min). Next, MS/MS analysis was performed using an electrospray ionization (ESI) source with Triple TOF 5600+ (AB Sciex, Framingham, Mass., USA) operating in a positive ion mode. Spermidine was quantified using multiple reaction monitoring (MRM) with mass transition from 146 m/z (Q1) to 72 m/z (Q3). The operating parameters were determined as follows: high resolution MS; MRM mode; electrospray ionization (ESI); 50 psi of atomized gas; 50 psi of heated gas; 25 psi of curtain gas; 500° C. in desolvation temperature; 4.5 kV in ion spray floating voltage; and 3.5 m Torr of collision gas.

13. Clinical Assay

Clinical research was conducted after obtaining prior consent from 22 female healthy volunteers aged 20-59 years. At day 1, prior to application of a test emulsion, basal skin conditions of all individuals were measured by visiting the individual volunteers. The respective volunteers were given a control emulsion and an emulsion containing the St solution. The respective emulsions were applied to each individual's cheek every day for 4 weeks and then examined at day 1, day 14 and day 28 after the emulsion application. The emulsions were all applied and examined under the conditions of 20 to 24° C. in temperature and 45 to 55% in relative humidity. The keratinocyte area (white area) was measured using ImageJ.

The face brightness of the frontal area was measured using Mark-Vu equipment (PSIPLUS Co., Ltd, Suwon, Korea) and a continuous light source. Data analysis was performed using Imax plus software and analysis results were expressed by L values.

The cheek transparency was measured using translucence measuring instrument (TLS850; Dia-Stron, Andover, UK). The intensity of light scattered from skin layer was measured using an optical fiber plate.

The trans-epidermal water loss (TEWL) of the cheek was measured using TEwameter TM300 (Courage+Khazaka electronic GmbH, Koln, Germany) for 25 seconds. TEWL indicates the moisturizing capacity and barrier function of the skin.

The face gloss was measured five times using Glossymeter GL200 (Courage+Khazaka electronic GmbH), and the average of the measured values was automatically computed.

The water content of the face was measured three times using Corneometer CM825 (Courage+Khazaka electronic GmbH), and the average was automatically computed. A difference in the dielectric constant between water and a measurement region was used.

The elasticity of the face was measured three times using Cutometer Dual MPA580 (Courage+Khazaka electronic GmbH), and the average was automatically computed. After applying a negative pressure of 450 mbar, the length of the skin layer extended was measured. The unit R2 was defined as Ua/Uf, in which Ua means final elastic regression, and Uf means final elastic deformation.

Skin layer desquamation was evaluated by harvesting desquamated skin cells using a D-squame standard sampling disk (D100; Clinical & Derm, Texas, USA) 와 Visioscan VC98 (Courage+Khazaka electronic GmbH). D.I was calculated using the following equation:

$$D.I = 2A + \frac{\sum_{n=1}^{5} Tn(n-1)}{6}$$ [Equation 1]

(A is a keratinocyte area ratio (%), Tn is a keratinocyte ratio associated with thickness, and n is a thickness level (1-5)).

14. Statistical Analysis

Statistical significances in the difference between groups for non-parametric data were calculated using Wilcoxon-Mann-Whitney test. Wilcoxon signed-rank tests were used for paired comparison. Each test was discriminated in the corresponding drawing legend, Pearson's correlation was used in correlation analysis, and Student's two-tailed t test was used in in vitro cell analysis.

Experimental Results

1. Identification of Primary Microbiota Structures related to Facial Skin Aging

Figure 1B:
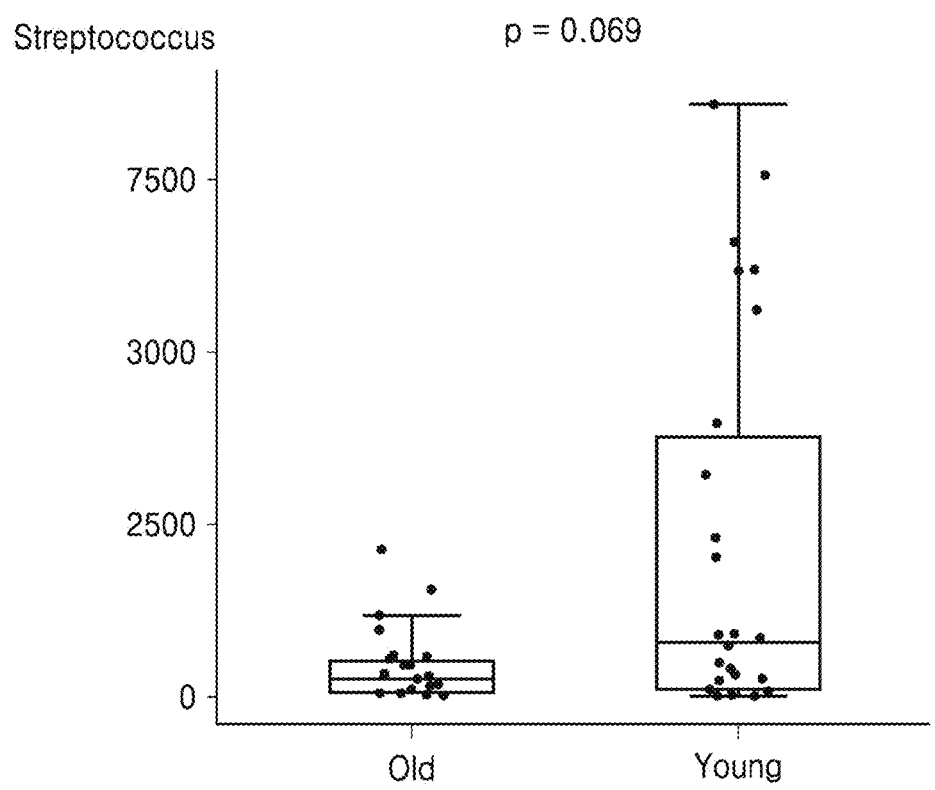
Figure 1C:
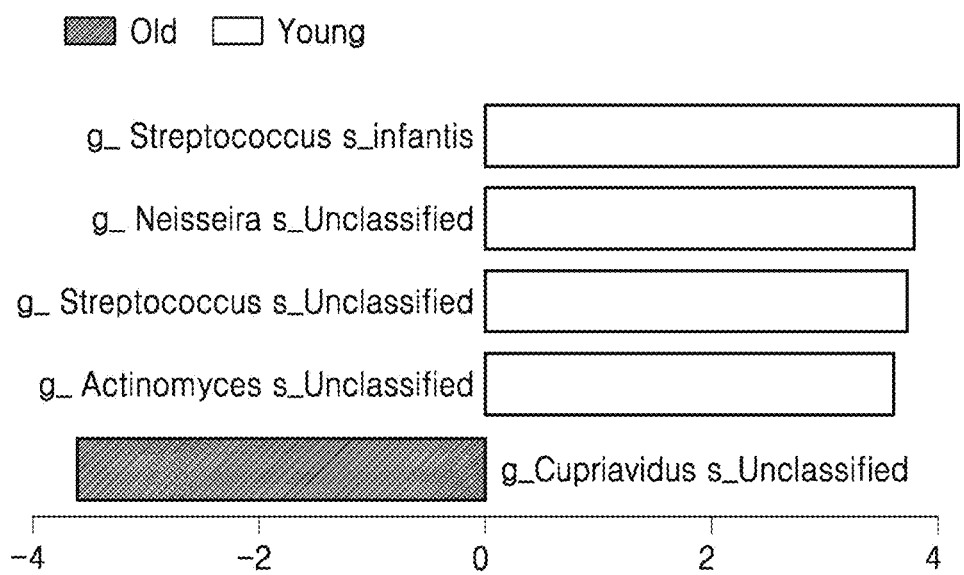
Figure 6A:
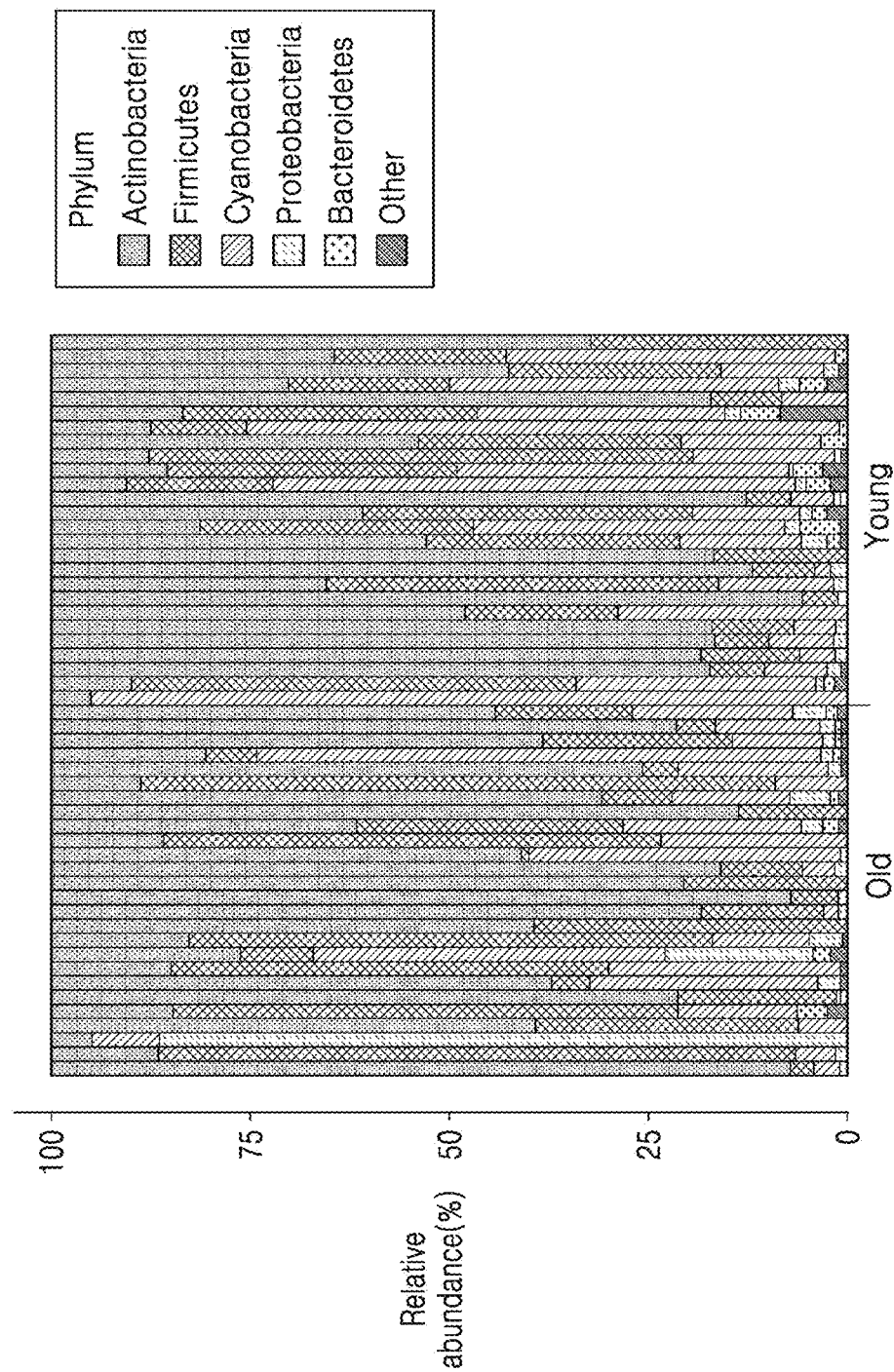
Figure 7A:
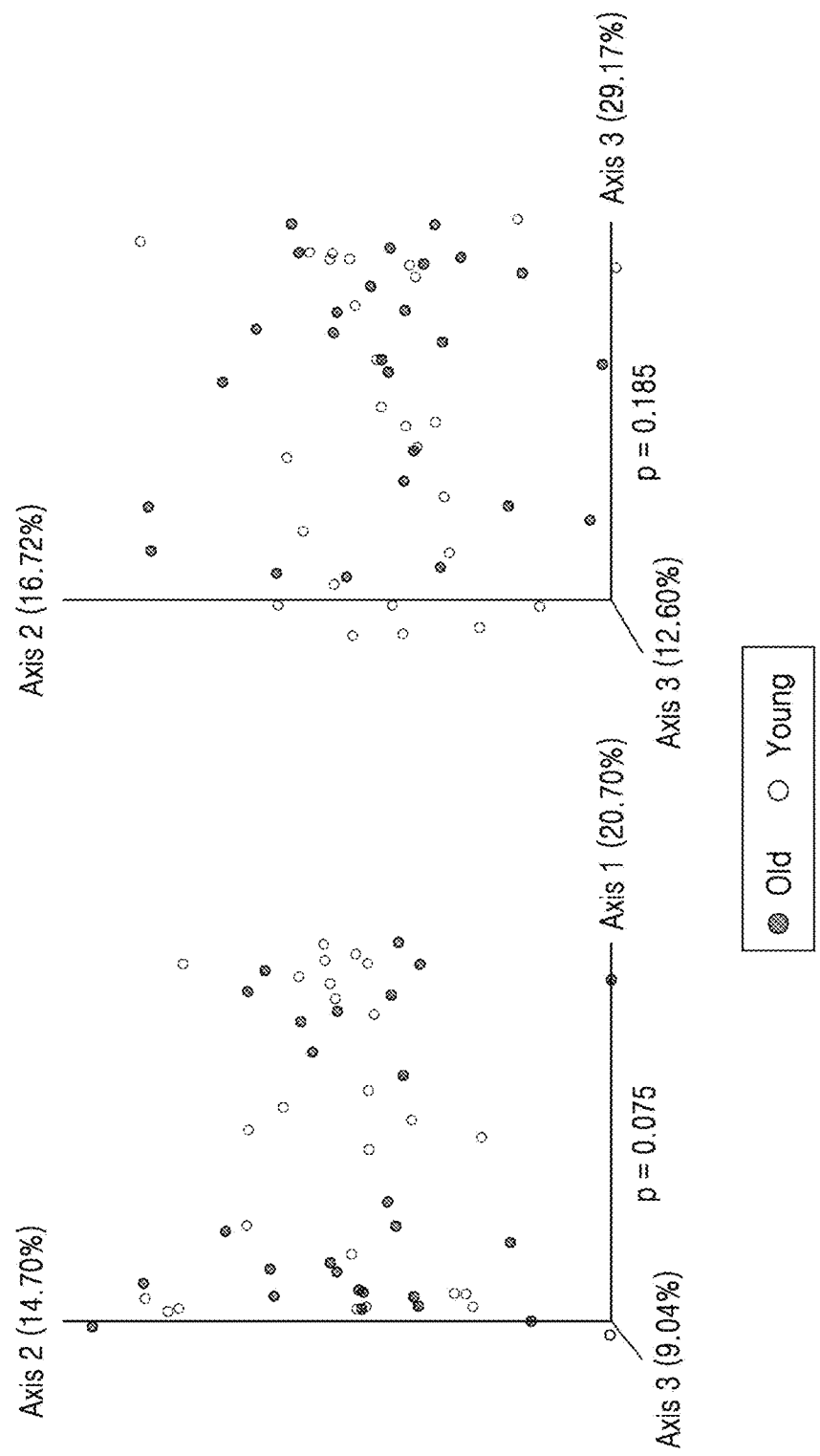
Figure 7B:
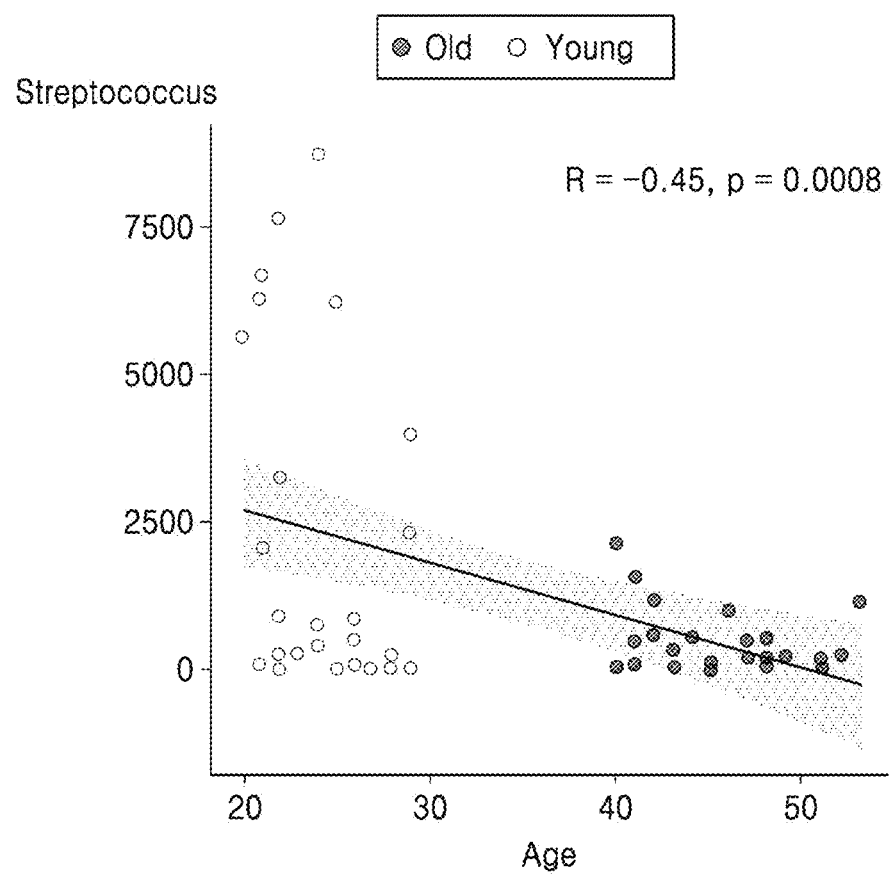

Experimental subjects were divided into two groups of old people (aged 40-53 years) and young people (aged 20-39 years). First, microbe compositions were weighed, and the entire face microbiota was assessed according to age. 16S rRNA Sequencing of facial skin samples was performed, the samples of 26 old people and 26 young people were compared, and the comparison results showed that equally top 5 abundant phyla were present in both groups (FIG. 6). Absence of age-linked stratification was confirmed by measuring microbial distances (FIG. 7A). At genus level, only *Streptococcus* tended to be more abundant in young people than in old people (FIGS. 1A, 1B and 7B), and no significant difference was observed in other geni (FIG. 7C). Specifically, *Streptococcus infantis* and several unclassified *Streptococcus* species were considerably abundant in young people (FIG. 1C). This means that *Streptococcus* species containing the *Streptococcus infantis* maybe closely related to aging of the facial skin.

2. Validation of Relationship between *Streptococcus* and Biophysical Characteristics of Face To select *Streptococcus* as a potential determinant of skin aging, biophysical characteristics of the skin were examined.

Figure 1D:
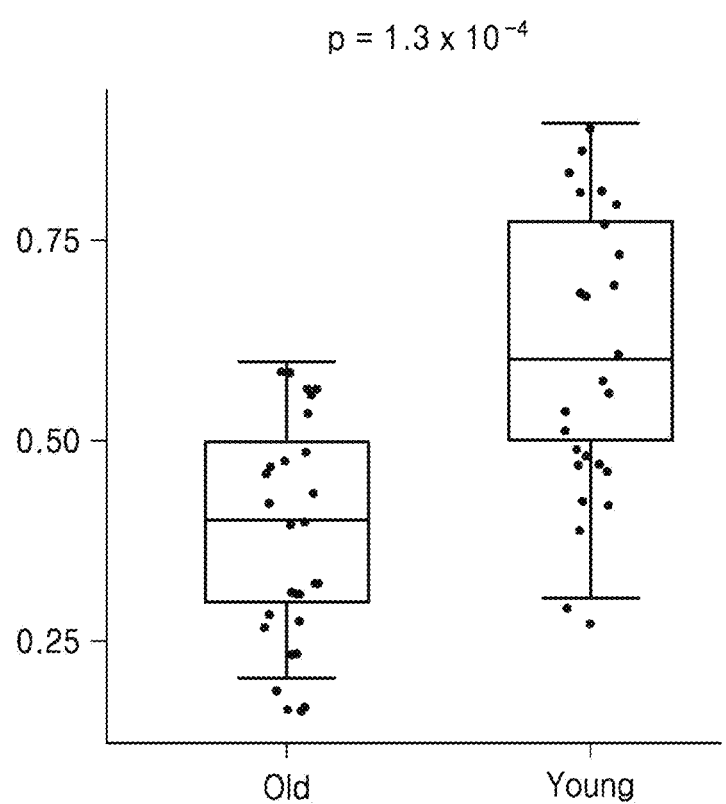
Figure 1E:
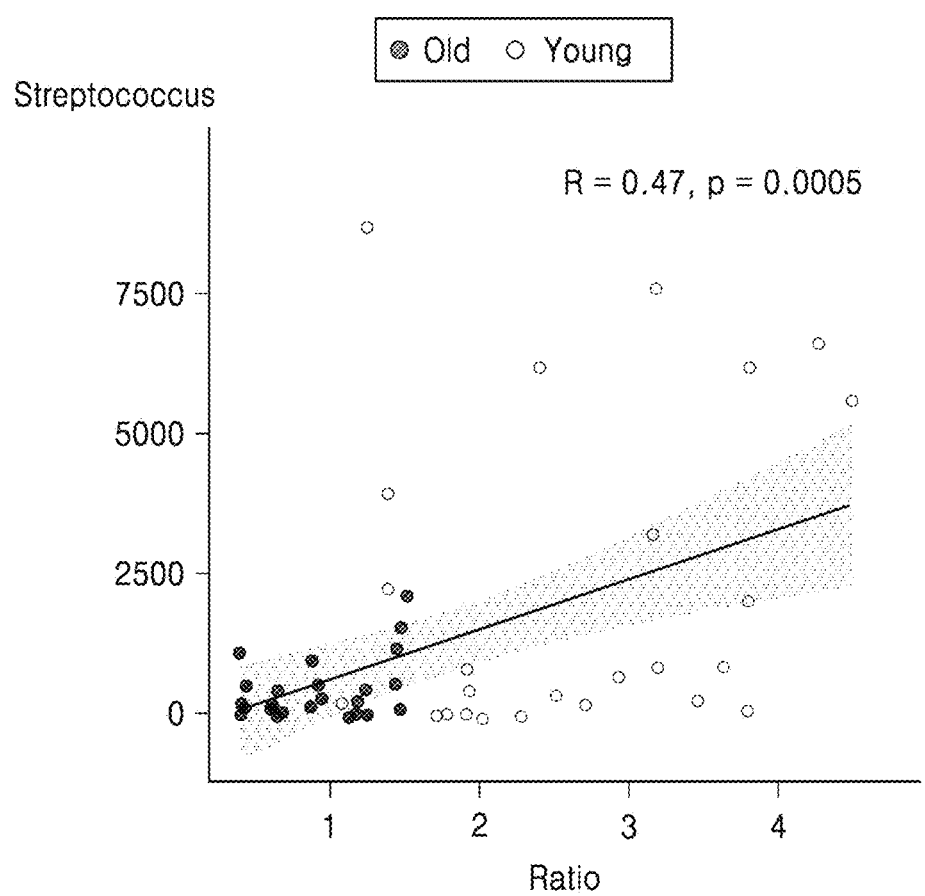
Figure 8A:
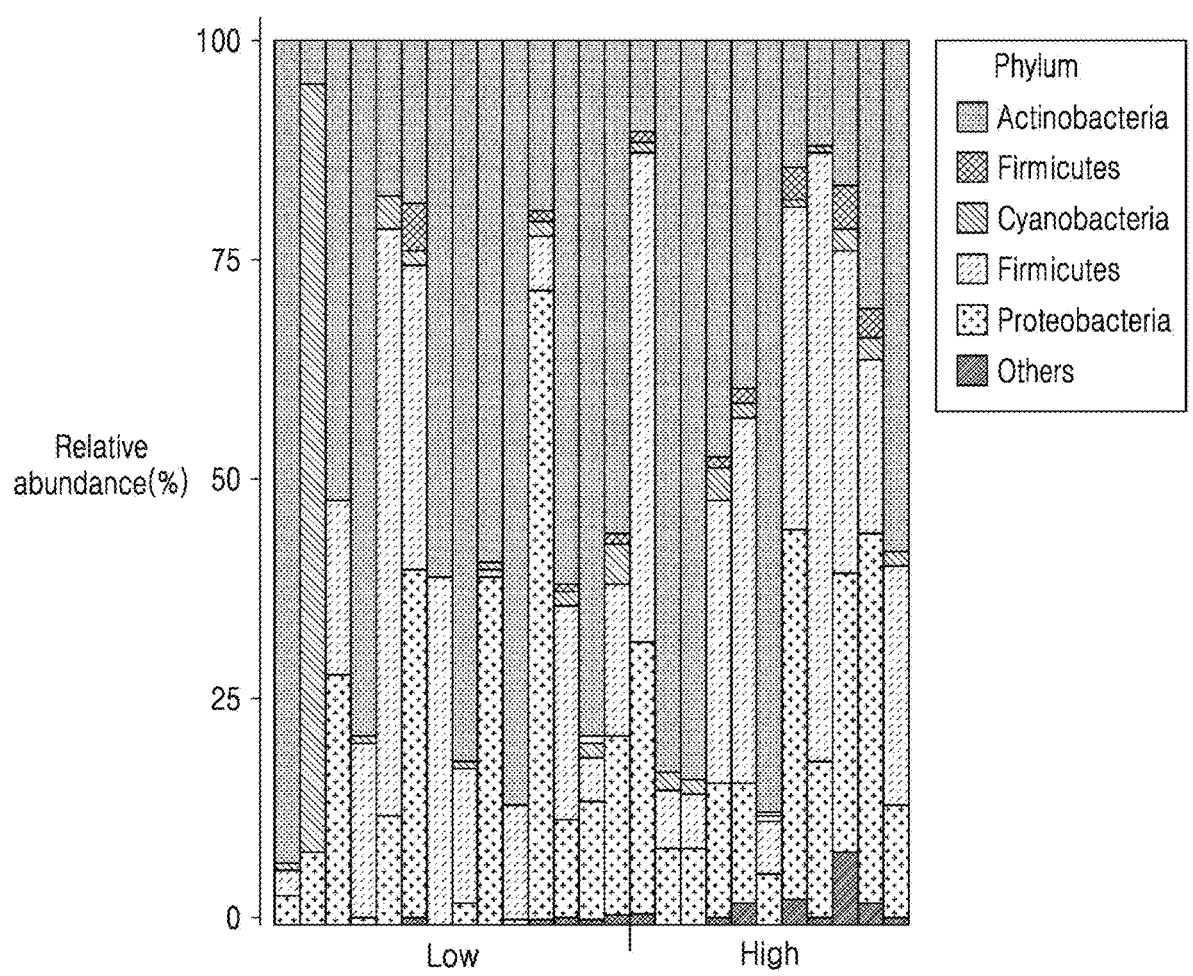
FIG. 8A, FIG. 8B, FIG. 8C, and FIG. 8D show microbe compositions of individual skin samples at phylum level.
Figure 8B:
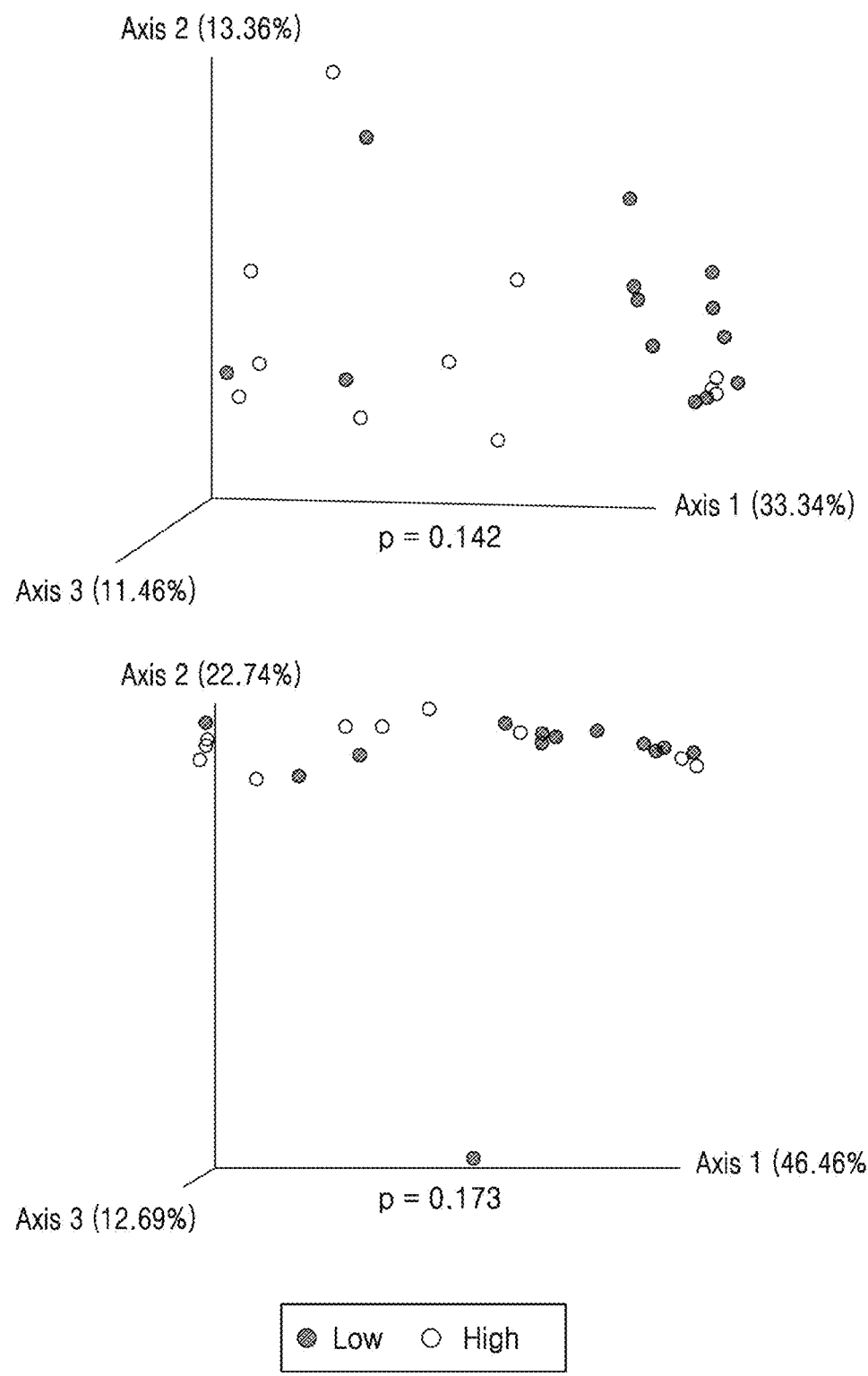
Figure 8C:
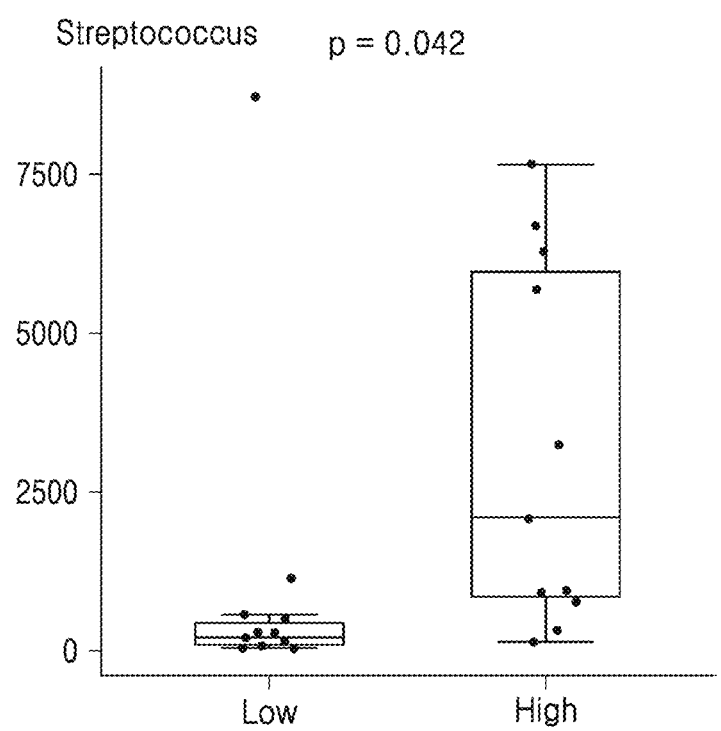
Figure 8D:
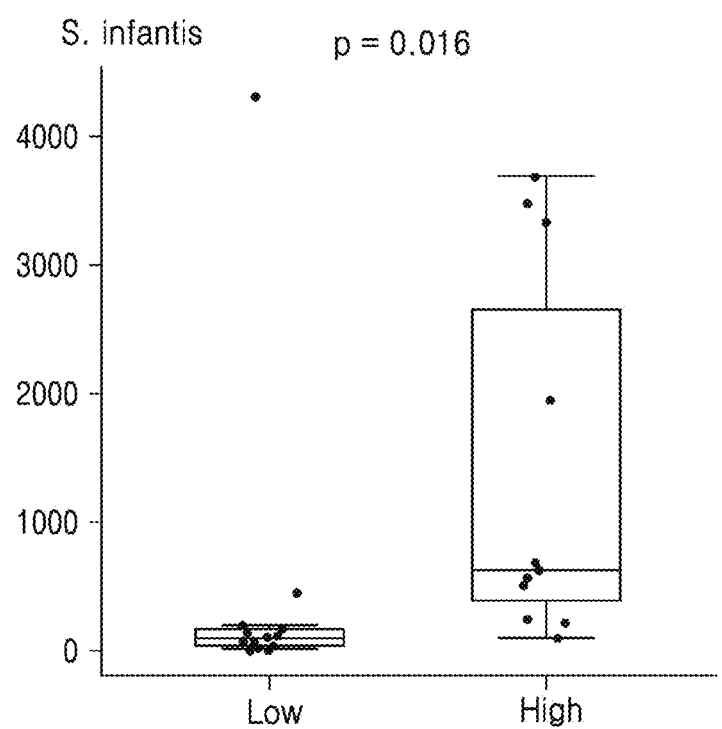

Elasticity is an important index for facial skin condition and is known to be related to age. Therefore, abundance levels of *Streptococcus* in individuals having different face elasticity levels were investigated. The elasticity was measured and scored from 0 to 1, and the elasticity scores were divided into three groups: low (0 to 0.3), average (0.4 to 0.6), and high (0.7 to 1). Individuals having high elasticity were determined to mostly belong to the young group (FIG. 1D). In order to validate the relationship between *Streptococcus* and facial skin elasticity, the relative abundance of *Streptococcus* was floated for the elasticity-to-age ratio of each of different individuals, and a positive correlation was obtained (FIG. 1E). Although the microbial compositions and distances of the individuals having different elasticity levels were not significantly different (FIG. 8), *Streptococcus* species, including *Streptococcus infantis*, were noticeably more abundant in the high-elasticity group than in the low-elasticity group (FIGS. 8C and 8D).

Figure 9A:
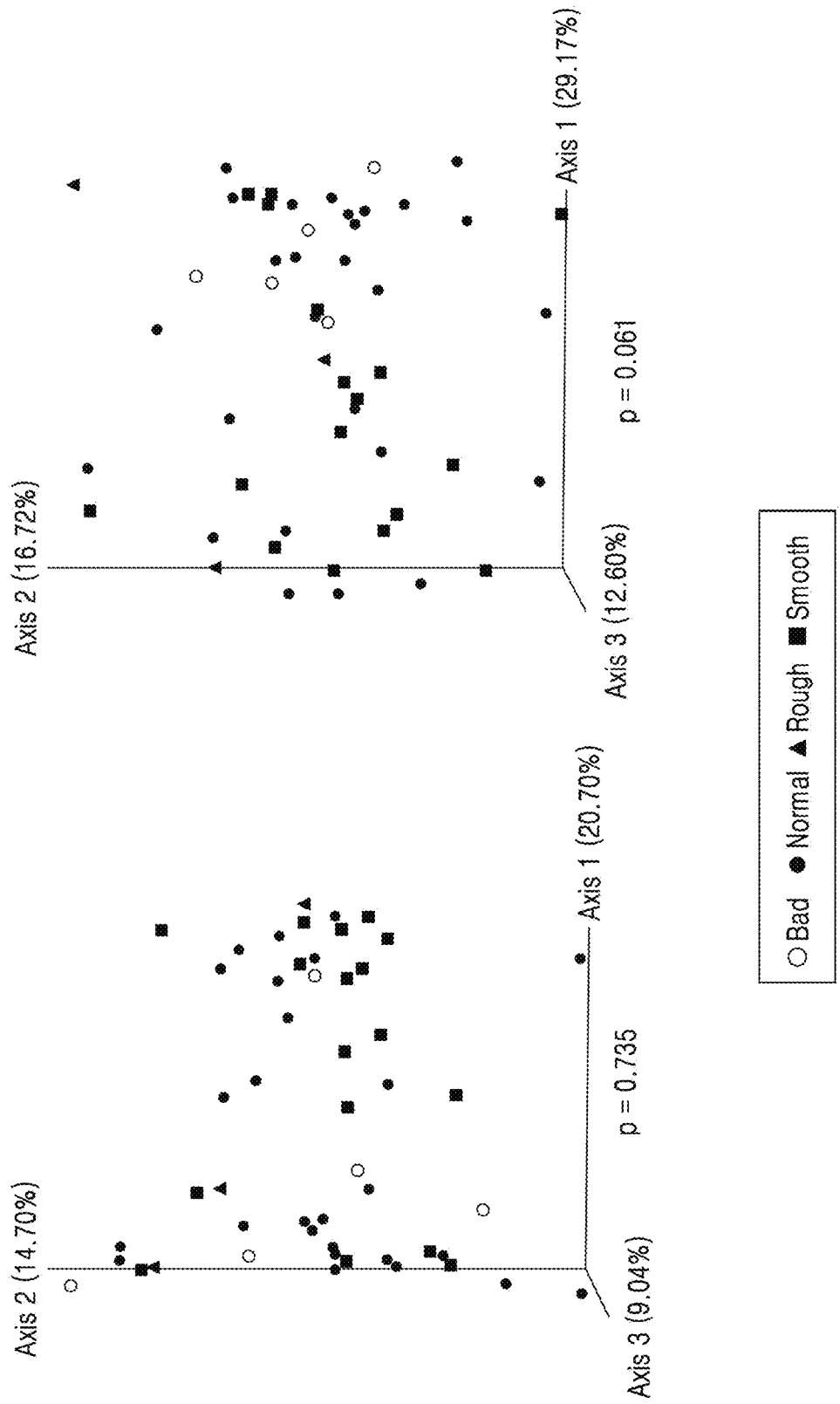
FIG. 9A, FIG. 9B, FIG. 9C, and FIG. 9D show the effect of face conditions on characteristics of skin microbes in individuals.
Figure 9B:
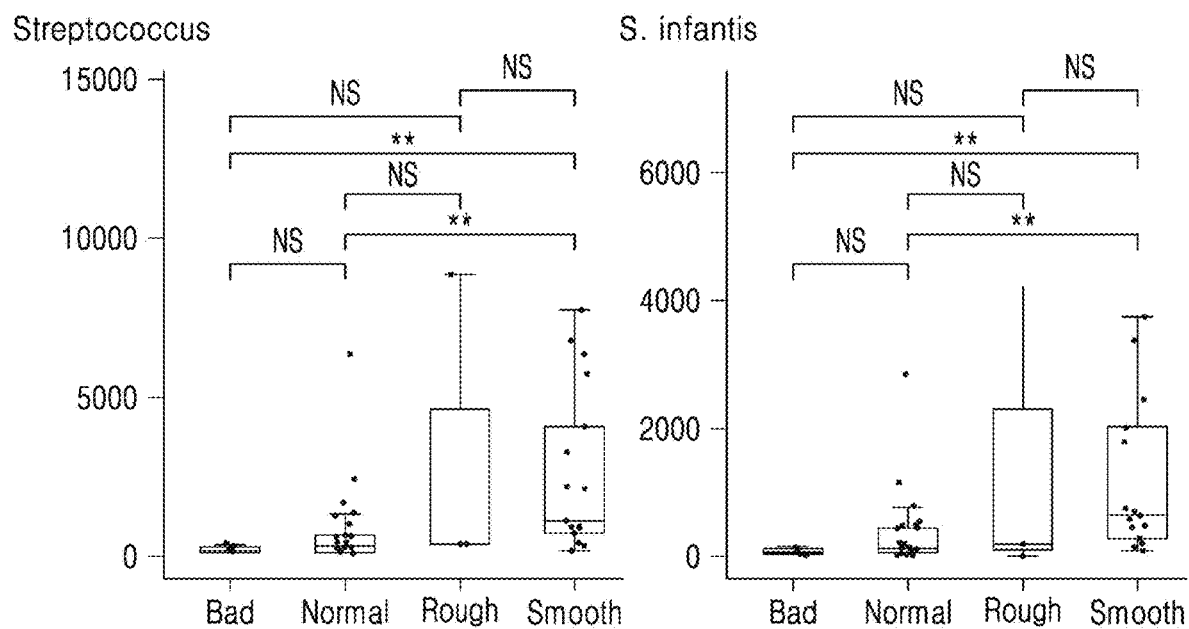
Figure 9C:
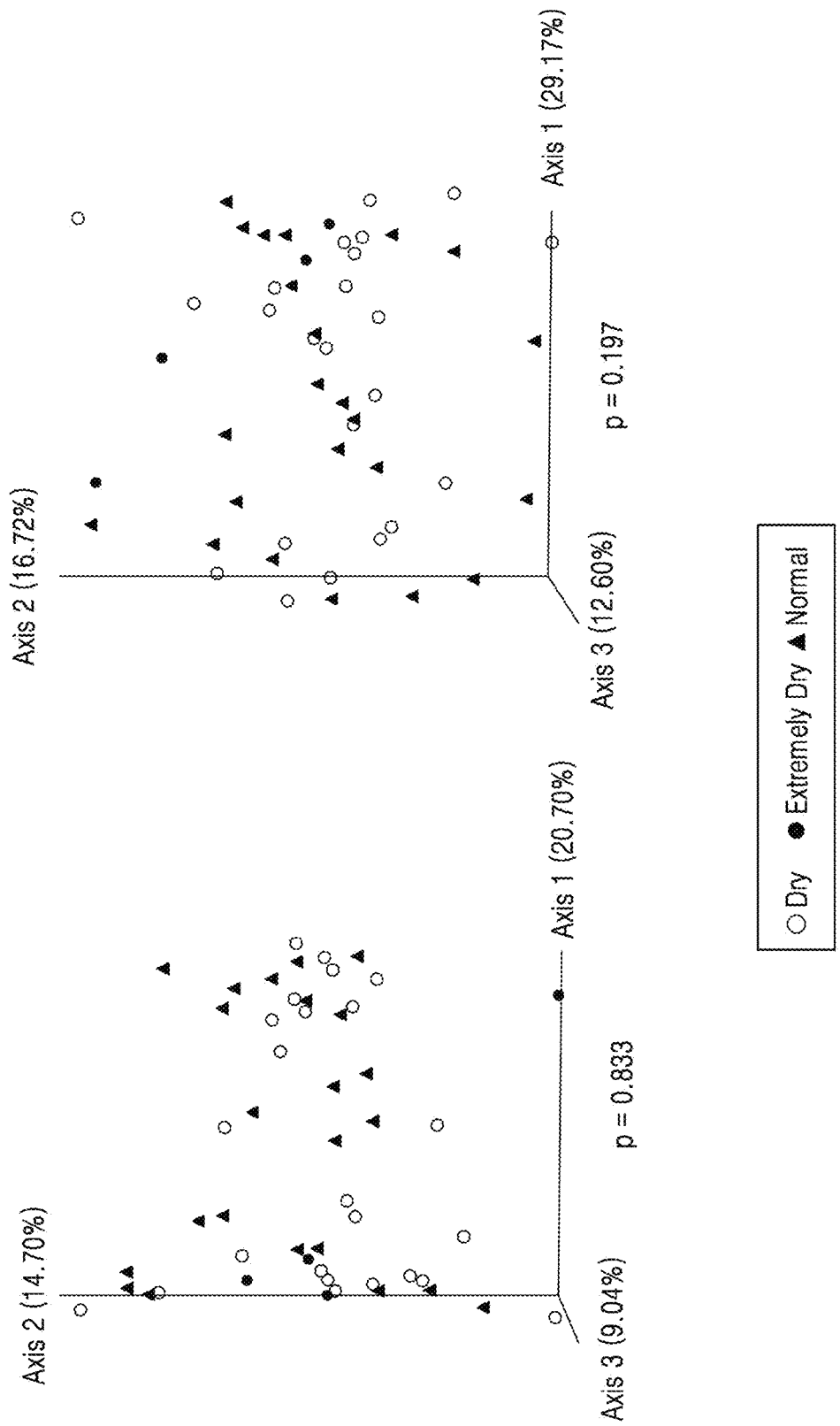
Figure 9D:
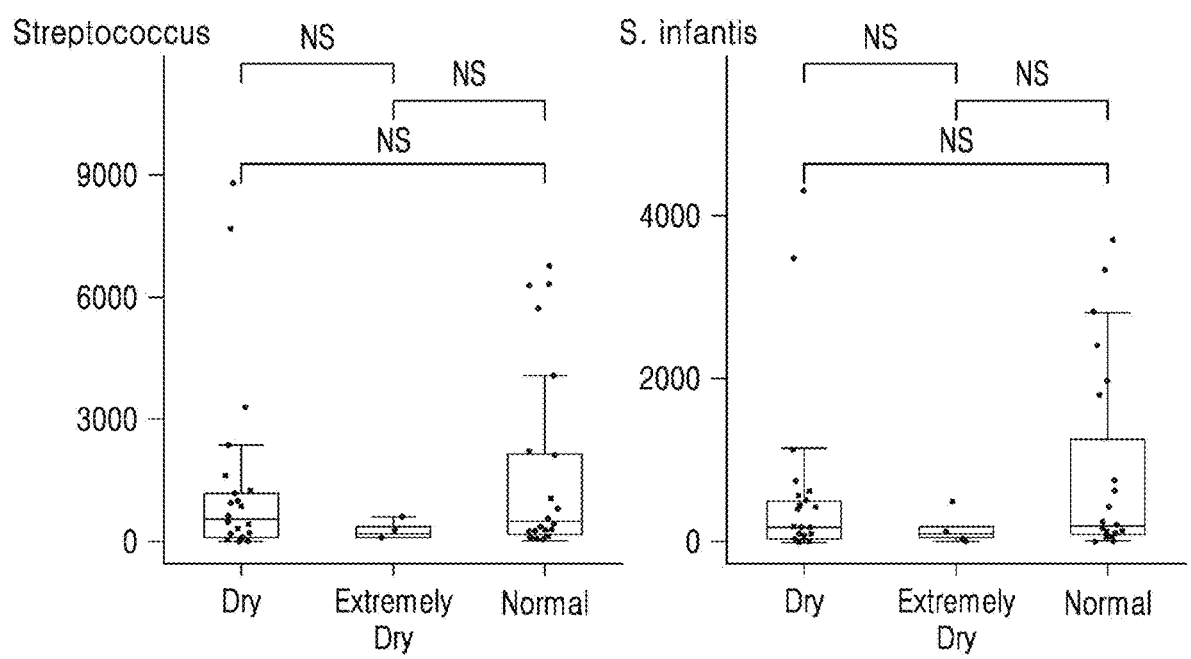

Comparison results of other variables, such as face water content or face conditions showed that there was no dependence of such variables on the microbial distance (FIGS. 9A and 9C). The *Streptococcus* species, including the *Streptococcus infantis*, were more abundant in individuals having smooth skin surfaces (FIG. 9B), whereas moisture did not seem to play a par (FIG. 9D).

This result suggests that the *Streptococcus* has a high probability of improving the facial skin condition.

3. Confirmation of Capability of *Streptococcus* Product in Controlling Skin Condition-related Factors To confirm whether the *Streptococcus* inhabiting on the skin of a young person, *Streptococcus pneumoniae*, *Strep-* tococcus infantis, Streptococcus mitis and Streptococcus thermophilus were isolated from the face skin of the young person. To validate whether Streptococcus candidates serve to perform functional roles on skin conditions, primary human dermal fibroblasts (HDFs) and human epidermal keratinocytes (HEKs) were treated with Streptococcus culture supernatant (St solution).

Figure 10A:
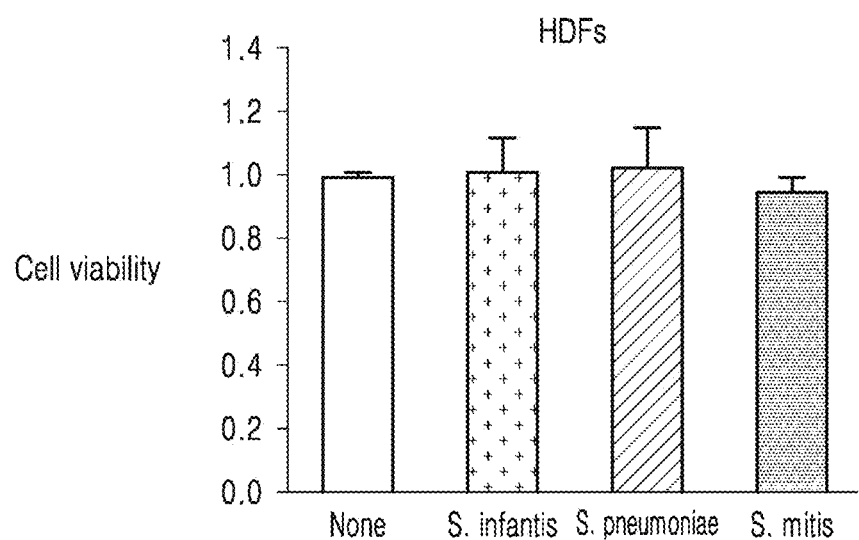
FIG. 10A, FIG. 10B, FIG. 10C, and FIG. 10D show toxicological screening test results of *Streptococcus* culture supernatants.
Figure 10A:
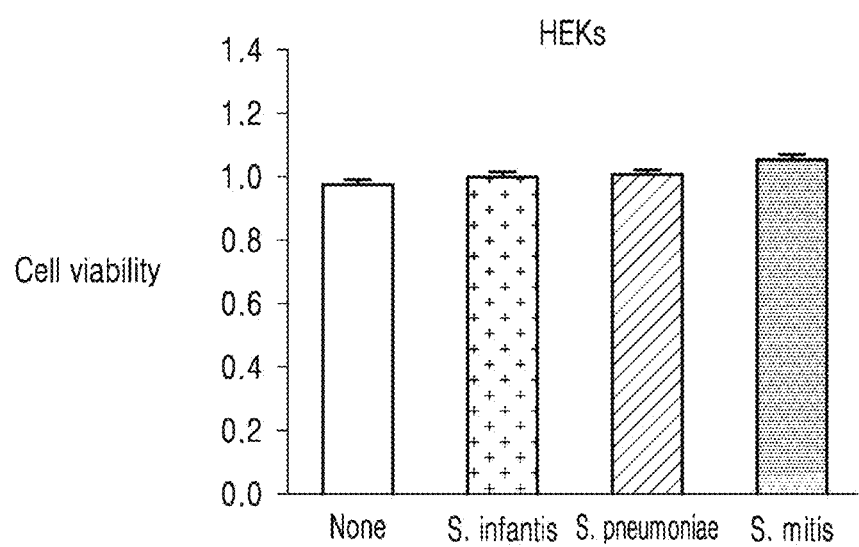
Figure 10B:
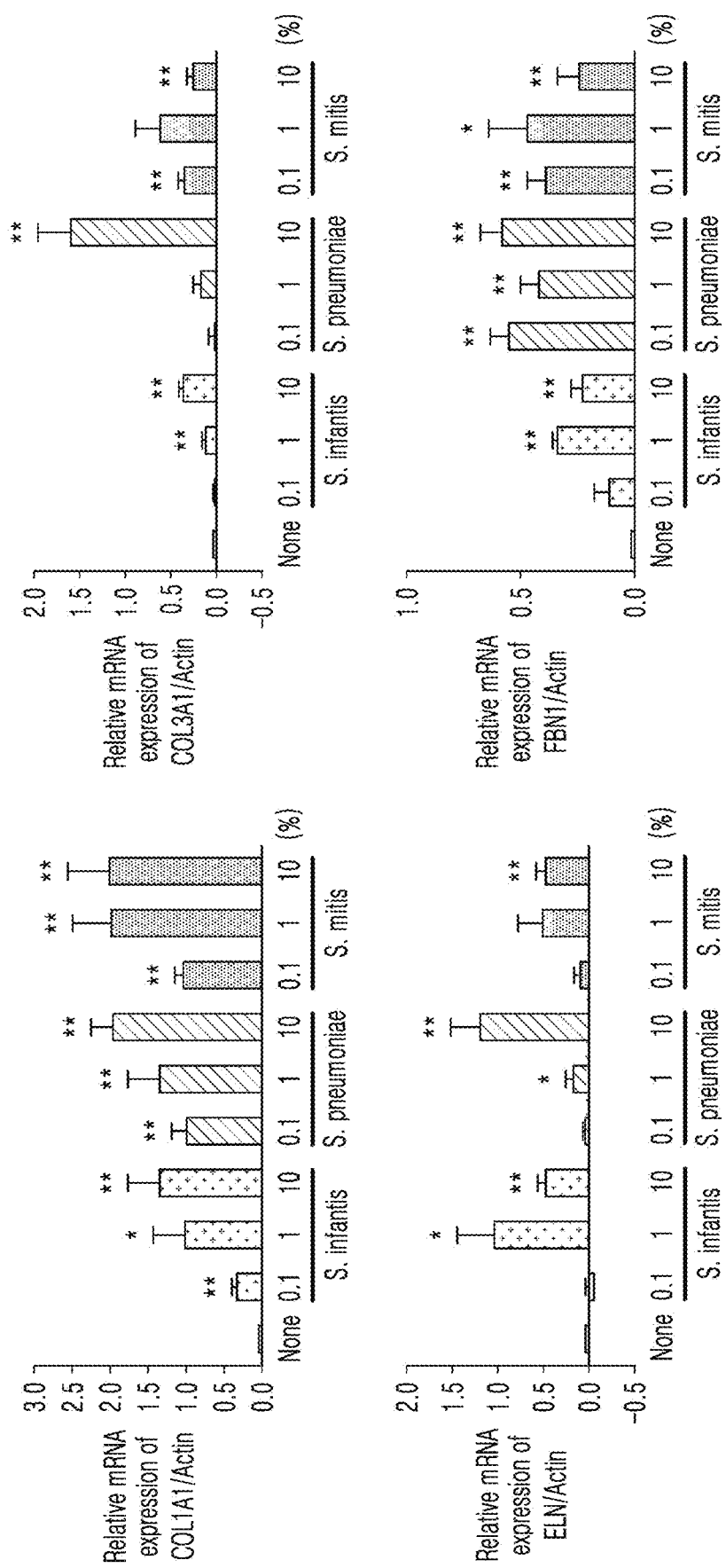

Prior to analysis, it was confirmed whether or not the St solution had toxicity with respect to the two cell types, and the optimal concentrations for the following experiments were determined by treatment with the St solution of up to 10% (FIGS. 10A and 10B).

Figure 2A:
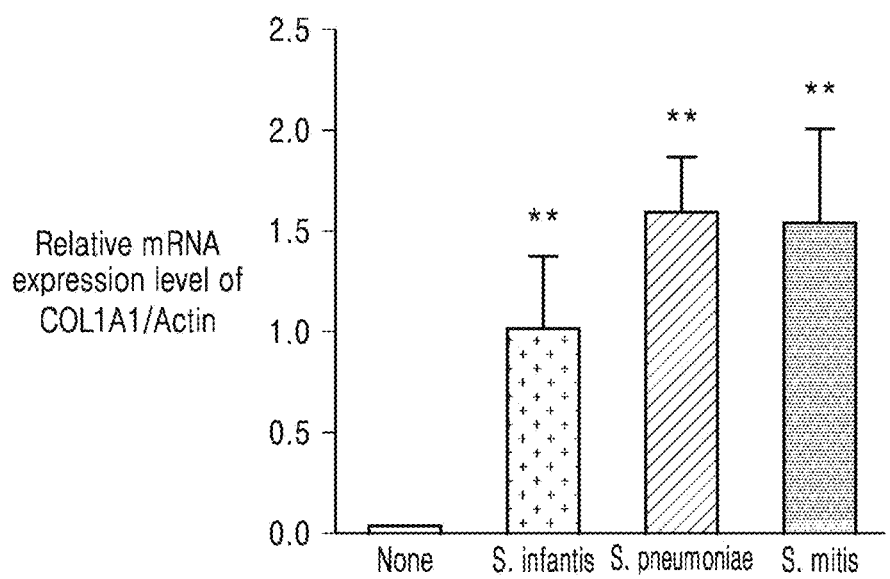
FIG. 2A, FIG. 2B, FIG. 2C, FIG. 2D, and FIG. 2E show increased expression of HDF and HEK genes after treatment of *Streptococcus* culture media.
Figure 2A:
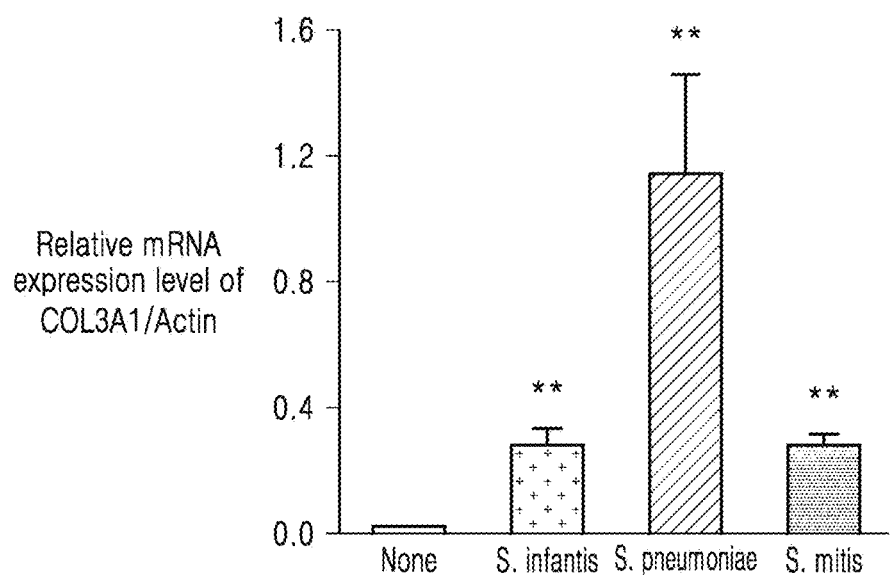

To evaluate the effect of the St solution on skin aging, the expression of genes involving the dermal structure was analyzed. Streptococcus infantis, Streptococcus pneumoniae and Streptococcus mitis solutions significantly increase the expression levels of COL1A1 and COL3A1, which are two primary components of the extracellular matrix (FIG. 2A).

Figure 2B:
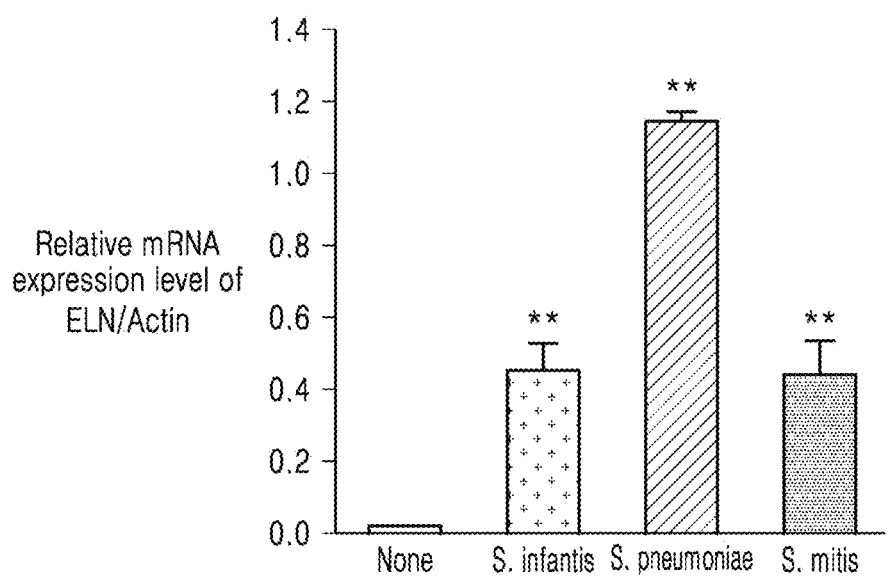
Figure 2B:
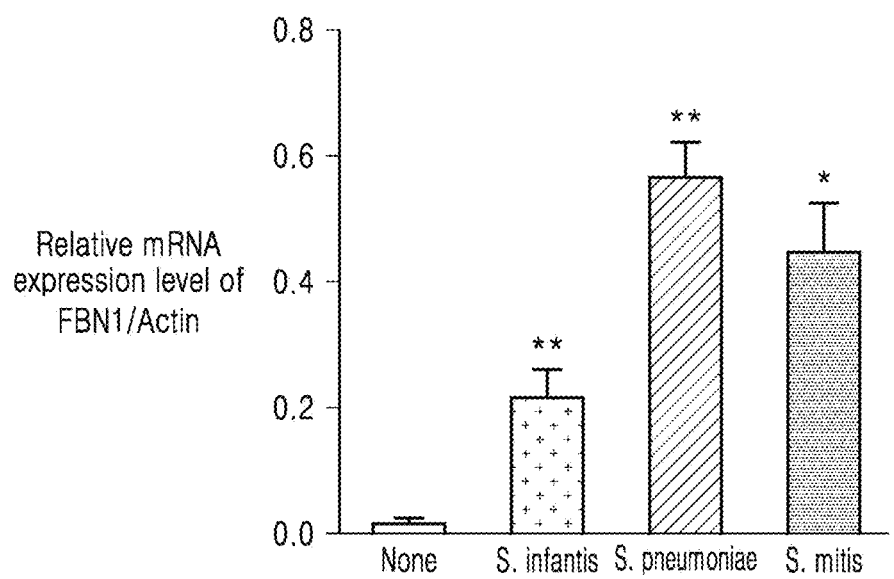

In addition, ELN and FBN1, which are important fiber genes associated with skin elasticity, were considerably induced from human fibroblasts by the St solution (FIG. 2B). Specifically, the Streptococcus pneumoniae culture medium demonstrated the most powerful effect.

In addition, when the aged skin model induced by polyinosinic:polycytidylic acid (poly I:C) was treated with the St solution, the multidimensional skin layer models demonstrated thicker epidermal layers (FIGS. 11A to 11E).

Figure 2C:
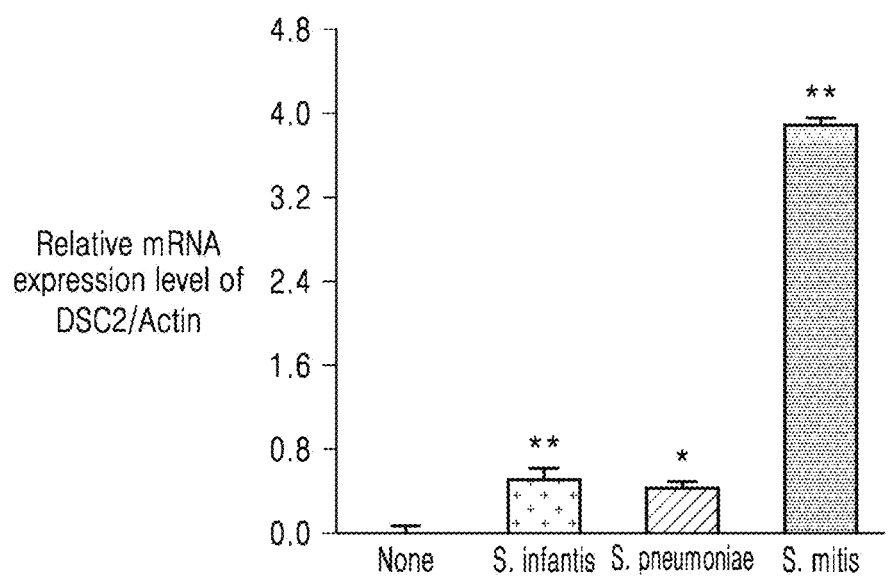
Figure 2C:
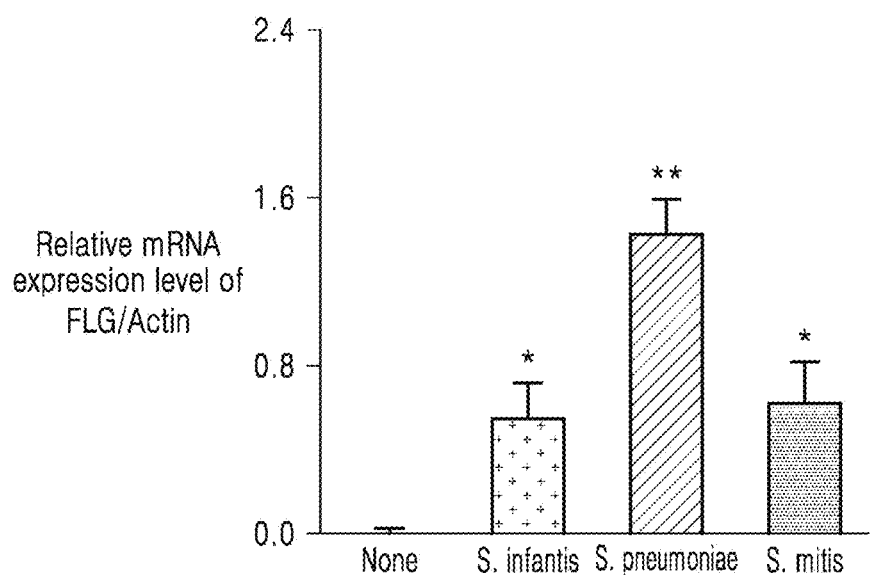
Figure 2D:
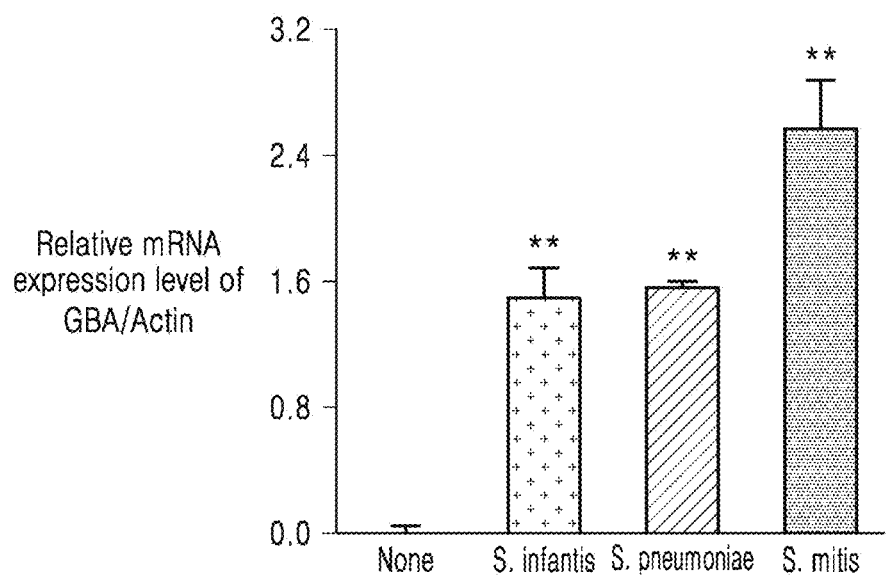
Figure 2D:
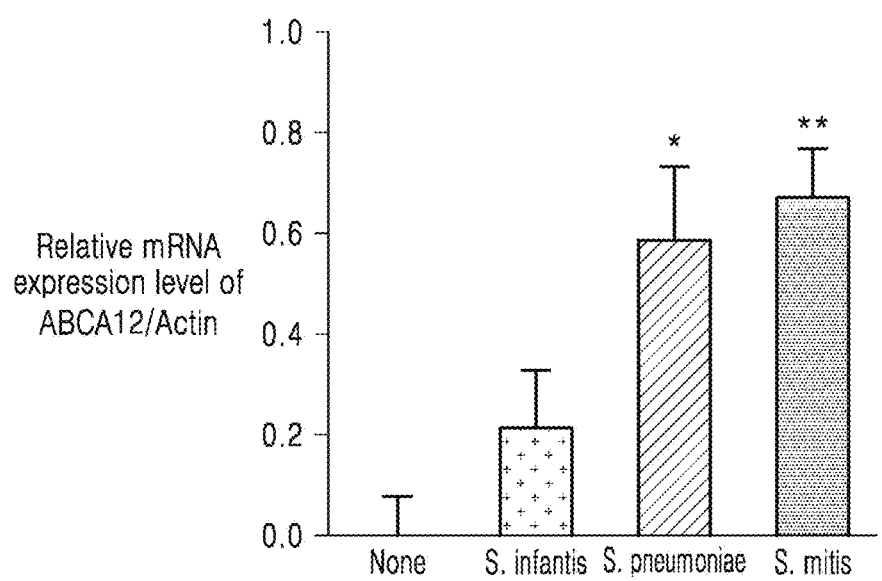

Further, after treatment of the St solution, mRNA expression levels of genes performing a skin barrier function, such as DSC2, FLG, etc., were increased (FIG. 2C). Similar tendencies were observed in GBA and ABCA12 genes enabling lamellar body and ceramide syntheses (FIG. 2D).

Figure 2E:
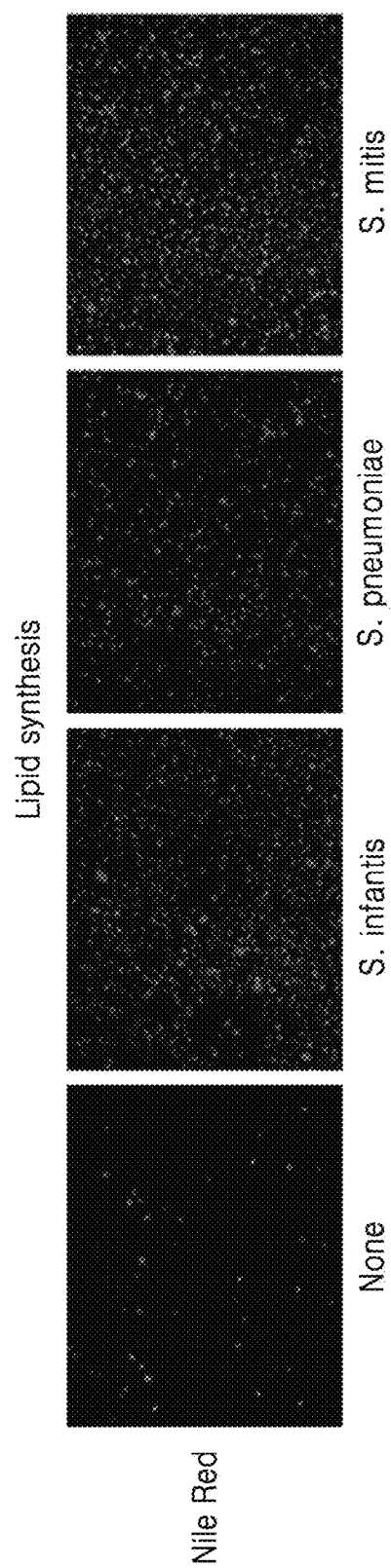
Figure 10C:
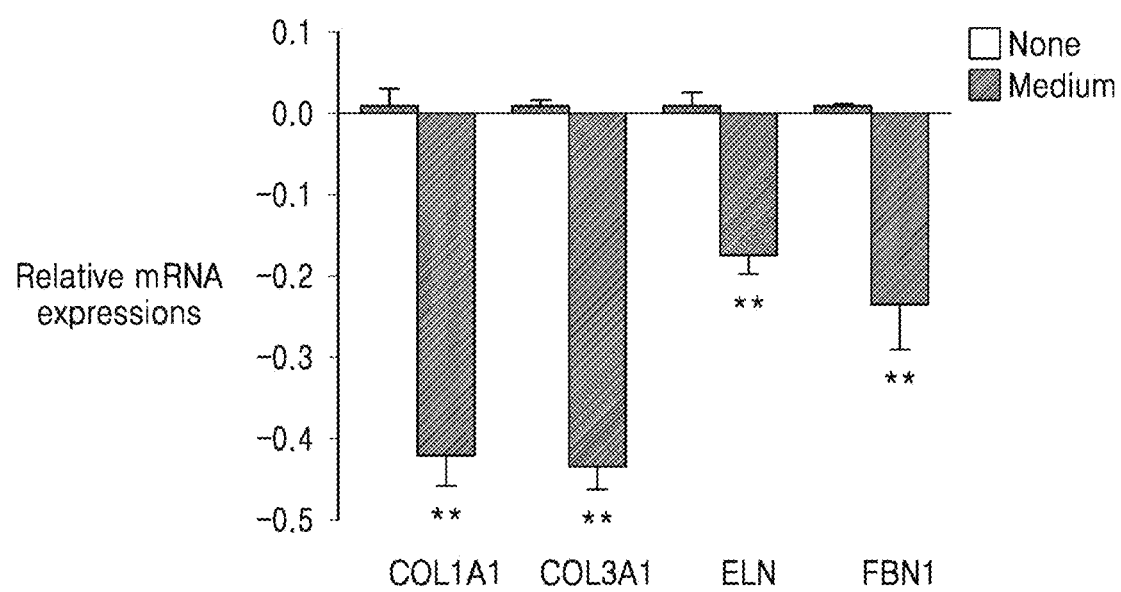
Figure 10D:
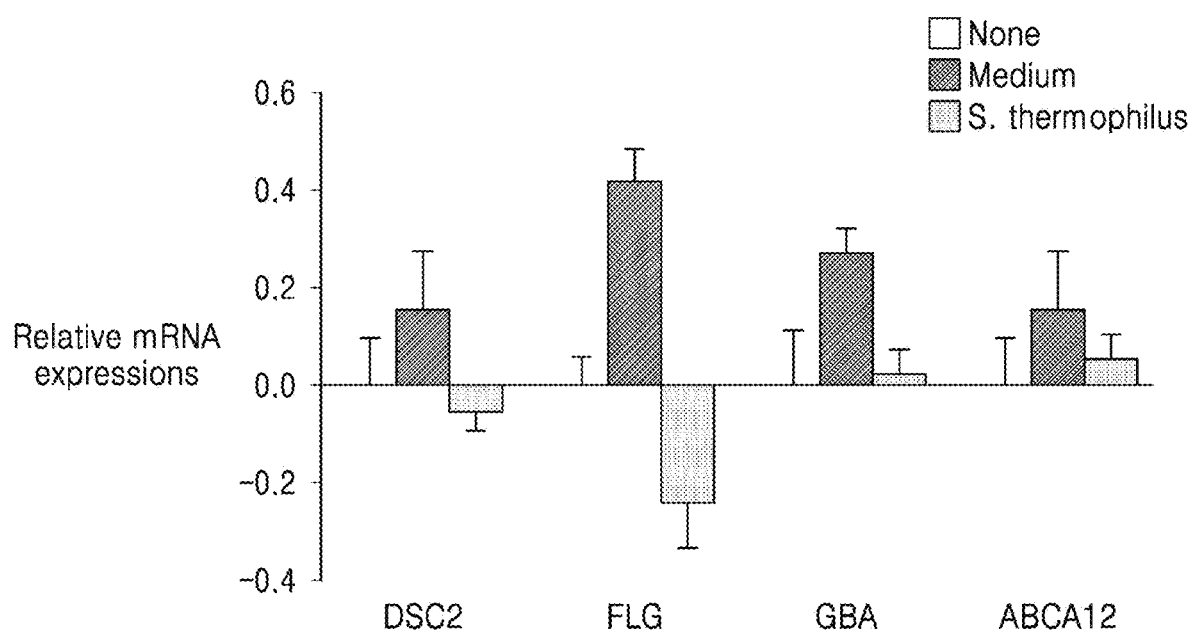
Figure 11A:
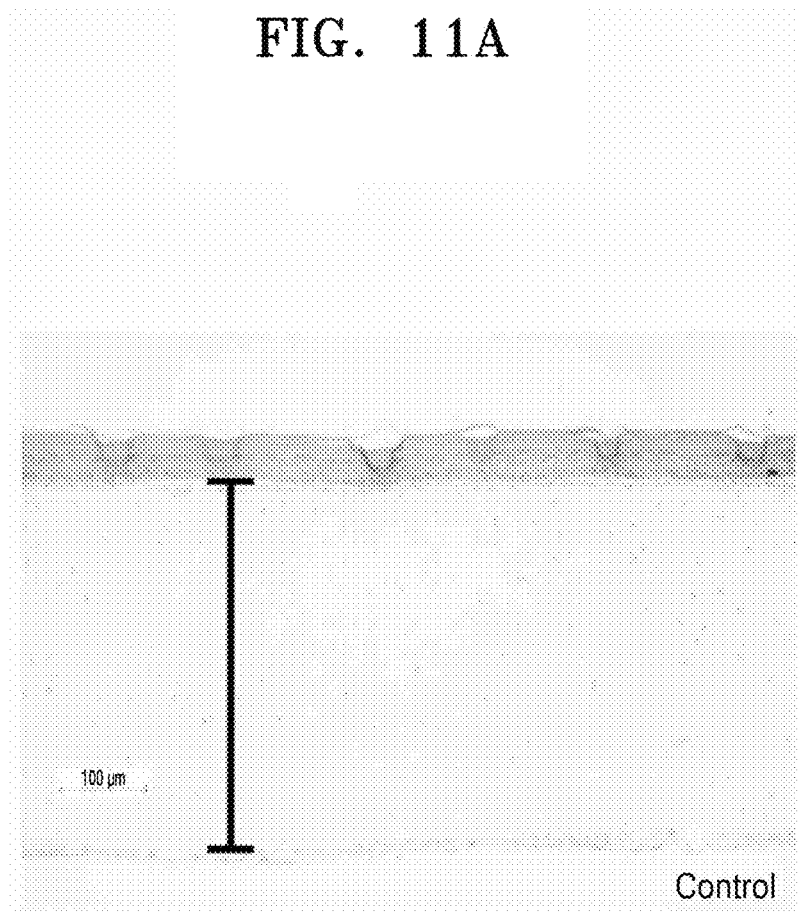
FIG. 11A, FIG. 11B, FIG. 11C, FIG. 11D, and FIG. 11E show multidimensional models of skin layers to which aging is induced after treatment of St solution.
Figure 11B:
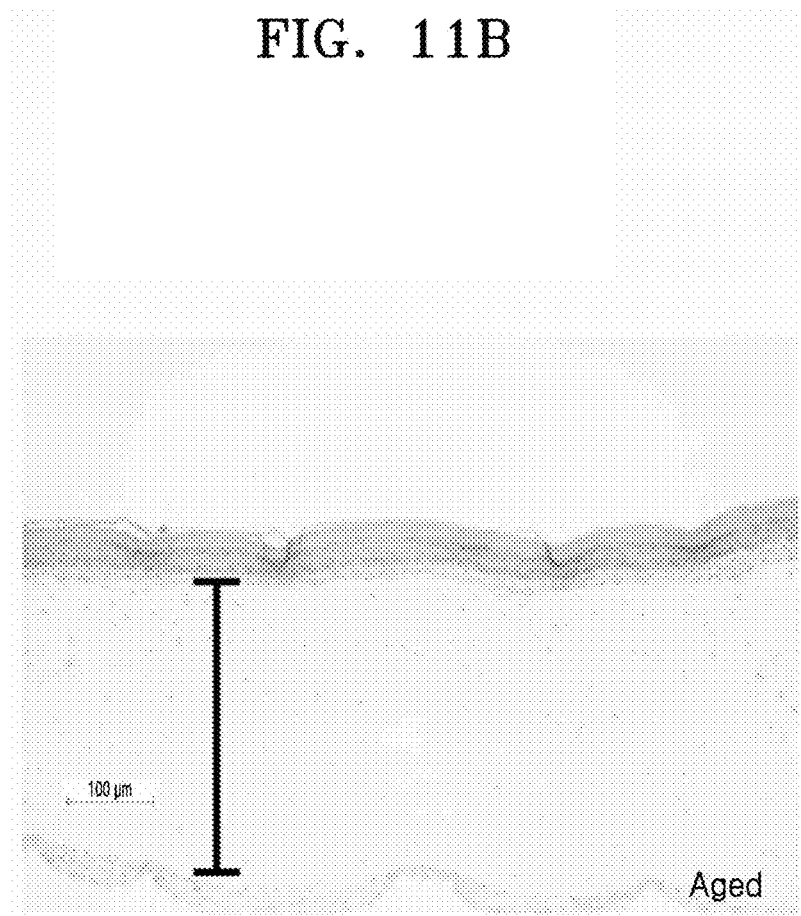
Figure 11C:
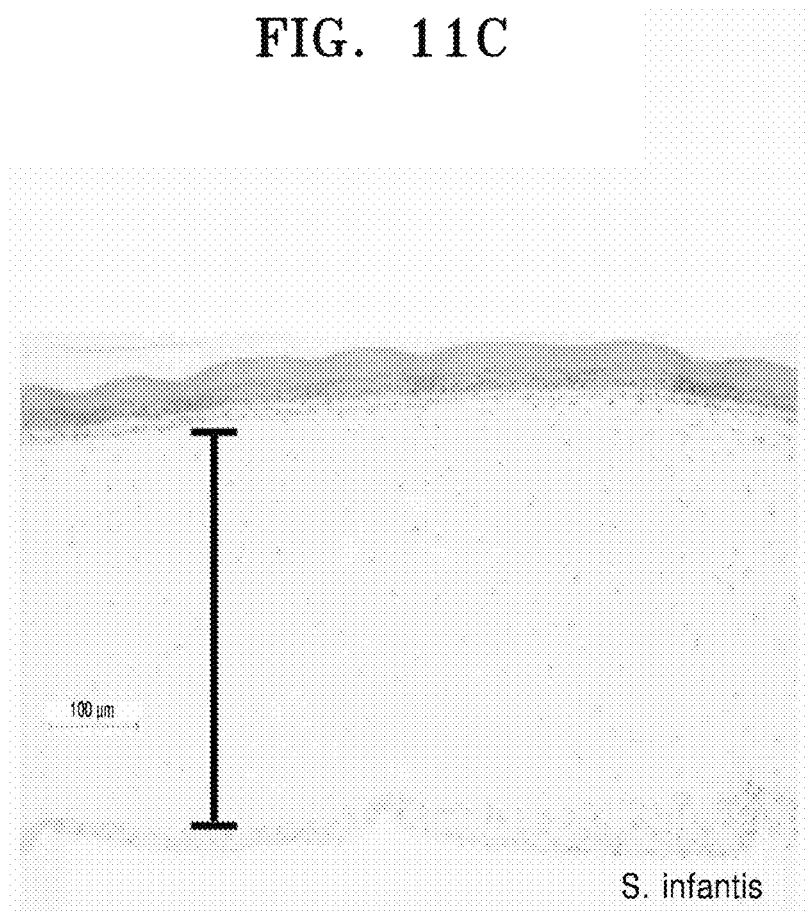
Figure 11D:
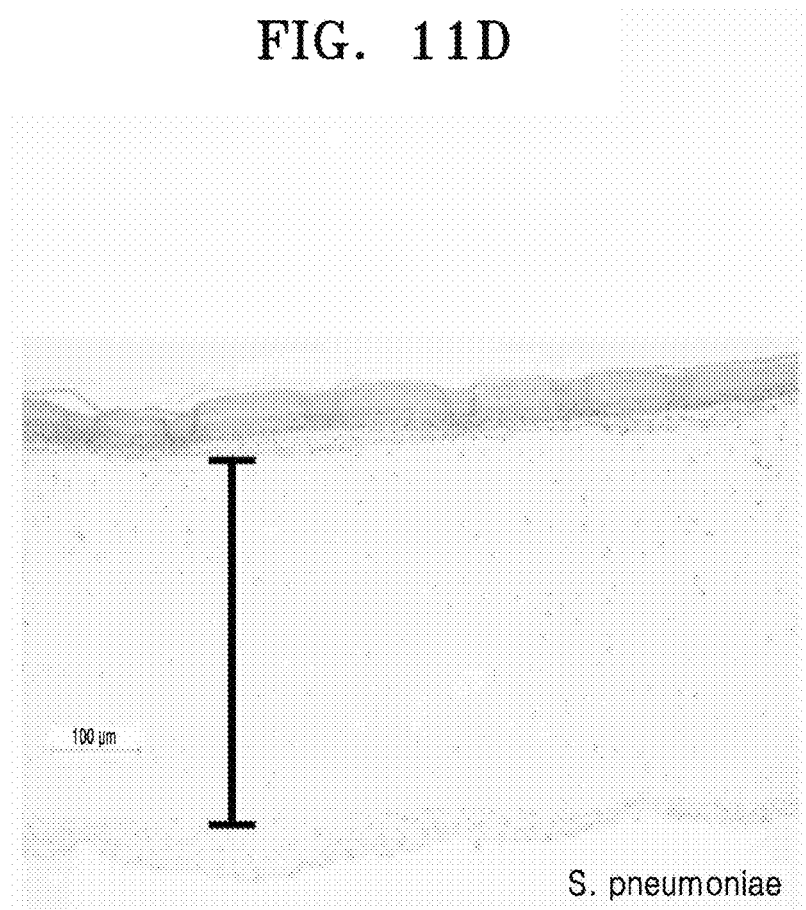
Figure 11E:
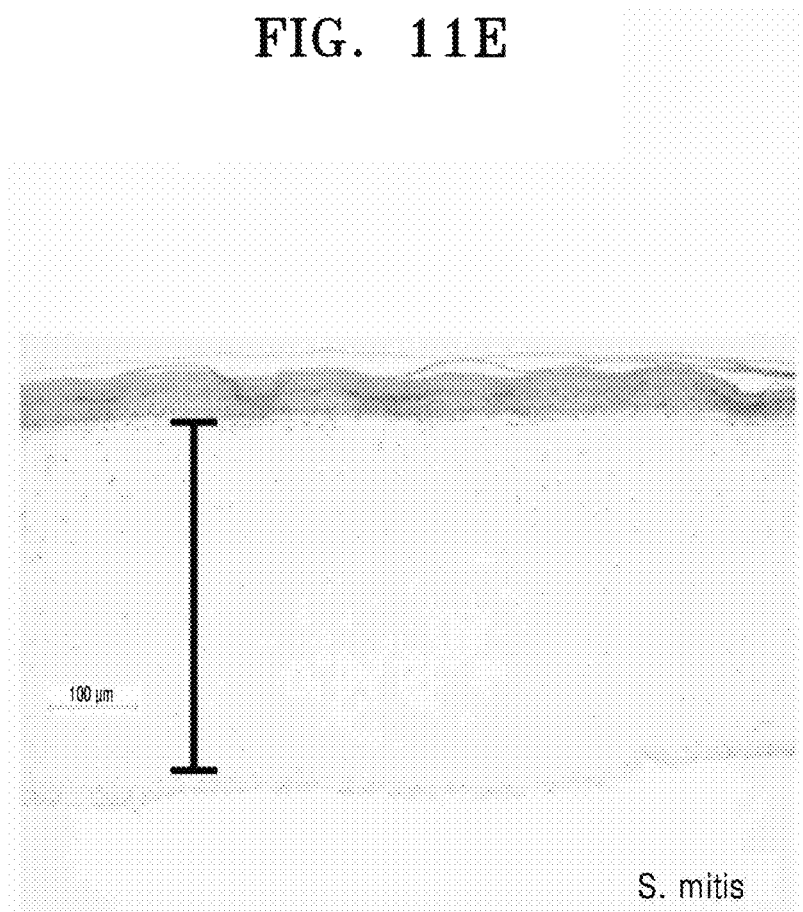

Moreover, the macroscopic effect of the St solution on the skin lipid synthesis and the resulting benefit of HEK capability in maintaining healthy barriers, were evaluated, confirming that the Streptococcus infantis solution, the Streptococcus pneumoniae solution, specifically the Streptococcus mitis solutions, increased lipid accumulation, by which gene expression profiles for lipid synthesis were identified (FIG. 2E). However, when the genes were treated with culture media only or treated with the culture supernatant containing the Streptococcus thermophilus, the same result was not obtained (FIGS. 10C and 10D).

4. Identification of Streptococcus Candidate Group and Biological Pathway

Figure 3A:
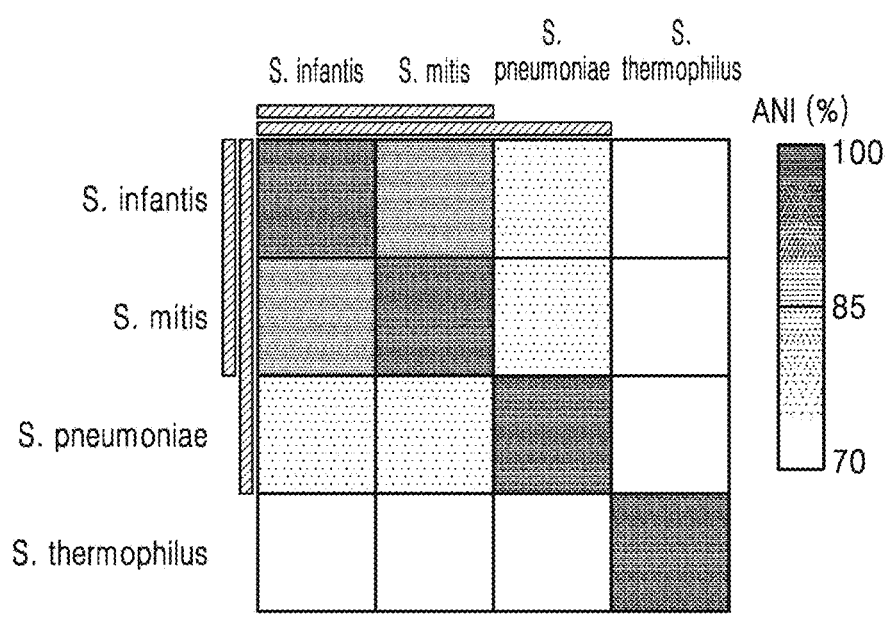

In order to investigate genomic and functional properties of Streptococcus candidates, the entire genomes were analyzed, and the Streptococcus infantis and Streptococcus mitis showed a closest genomic distance, followed by Streptococcus pneumoniae (FIG. 3A), which is a consistent result with the cellular analysis. Accordingly, the Streptococcus species were divided into two groups: group 1 (Streptococcus infantis, Streptococcus pneumoniae, and Streptococcus mitis); and group 2 (Streptococcus thermophilus).

Figure 3C:
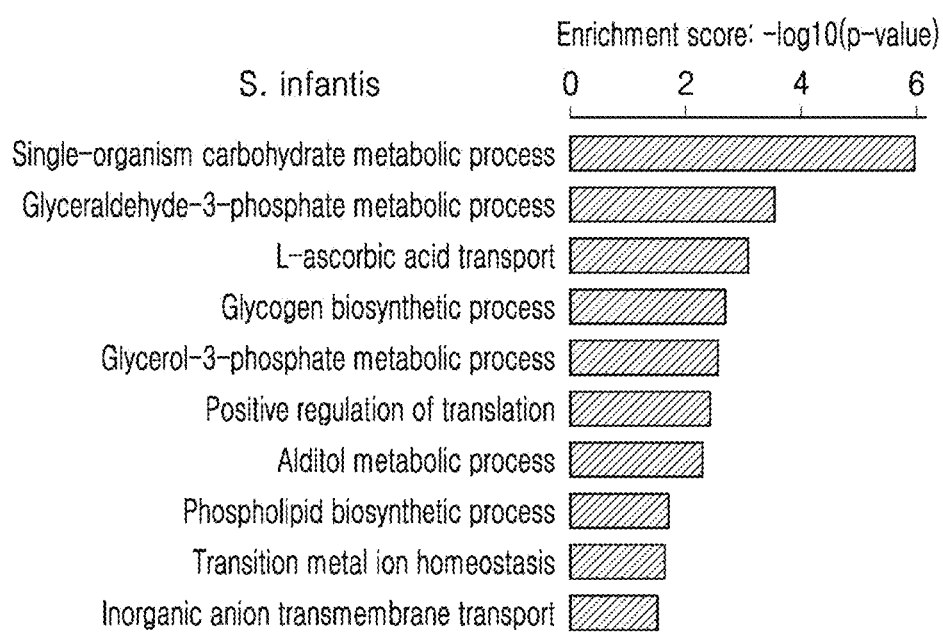
Figure 3D:
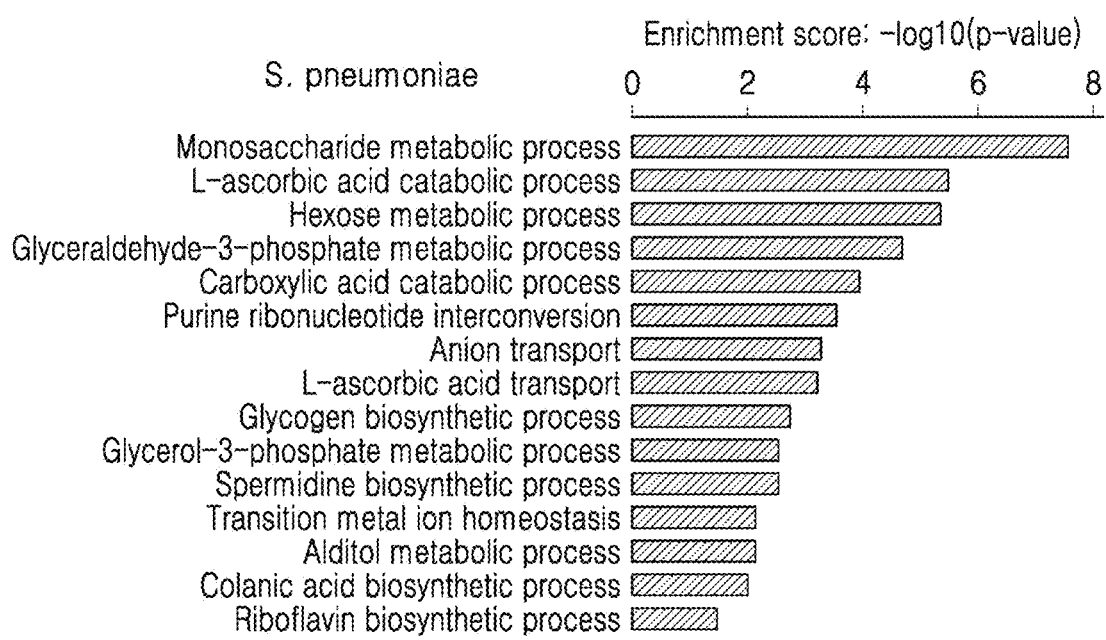
Figure 3E:
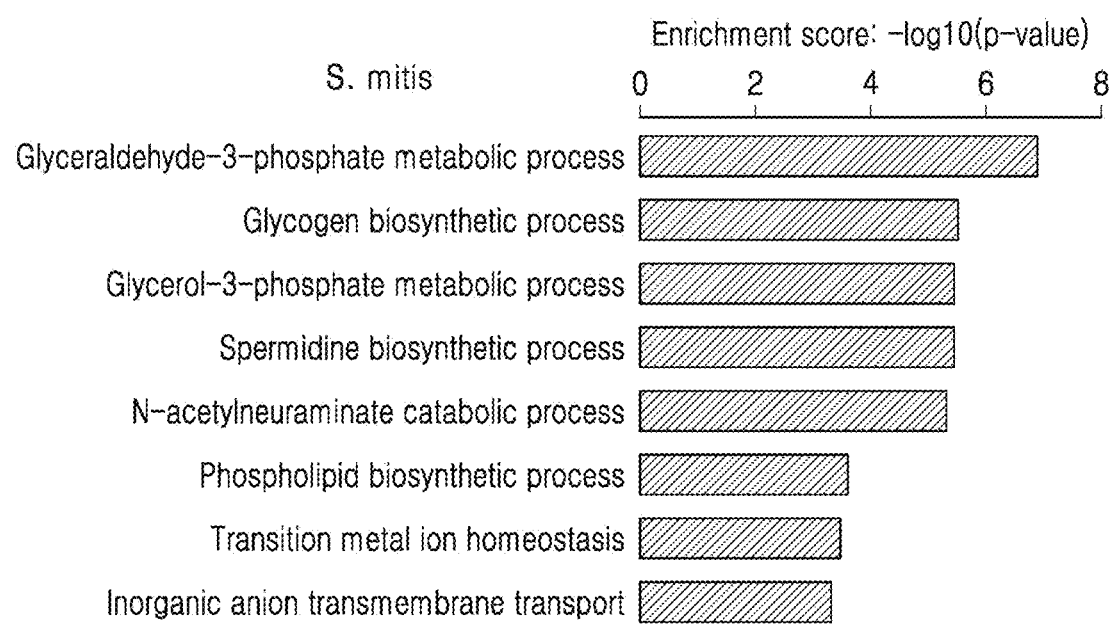
Figure 3F:
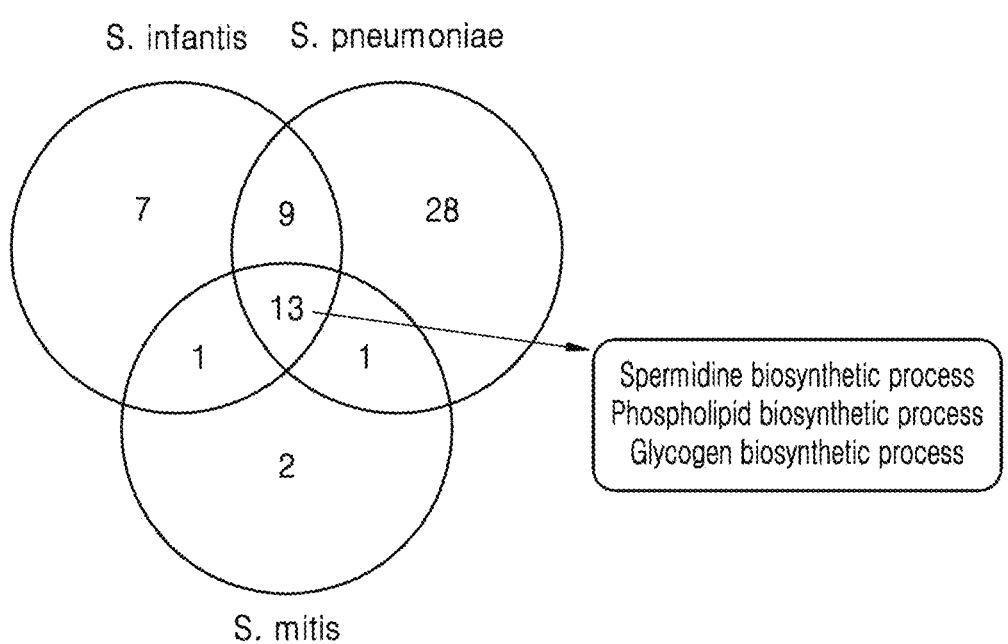
Figure 4A:
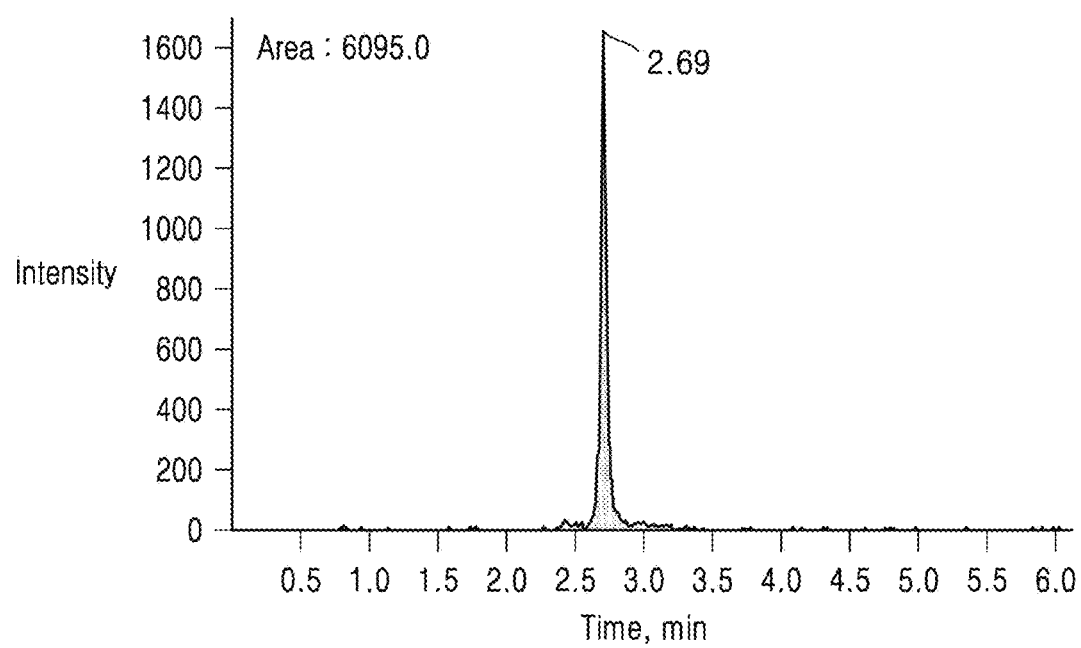
FIG. 4A, FIG. 4B, FIG. 4C, FIG. 4D, and FIG. 4E show that spermidine was detected in *Streptococcus* (St) using UPLC-QTOF-ESI-MS chromatograms (FIG. 4A: 10-fold diluted TSB control medium.
Figure 4B:
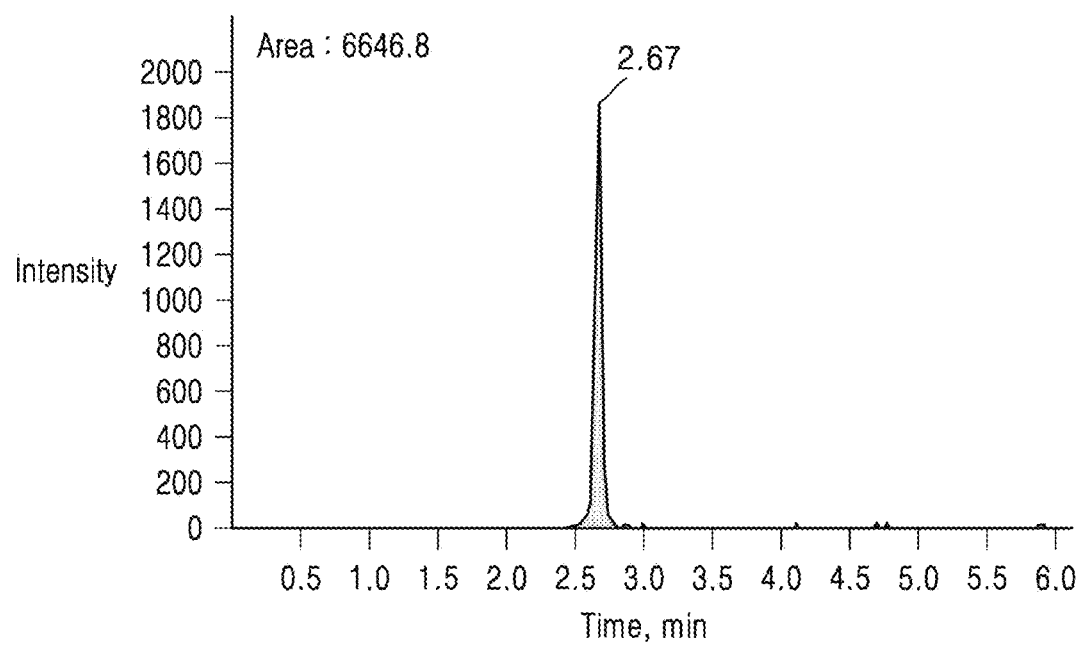
Figure 4C:
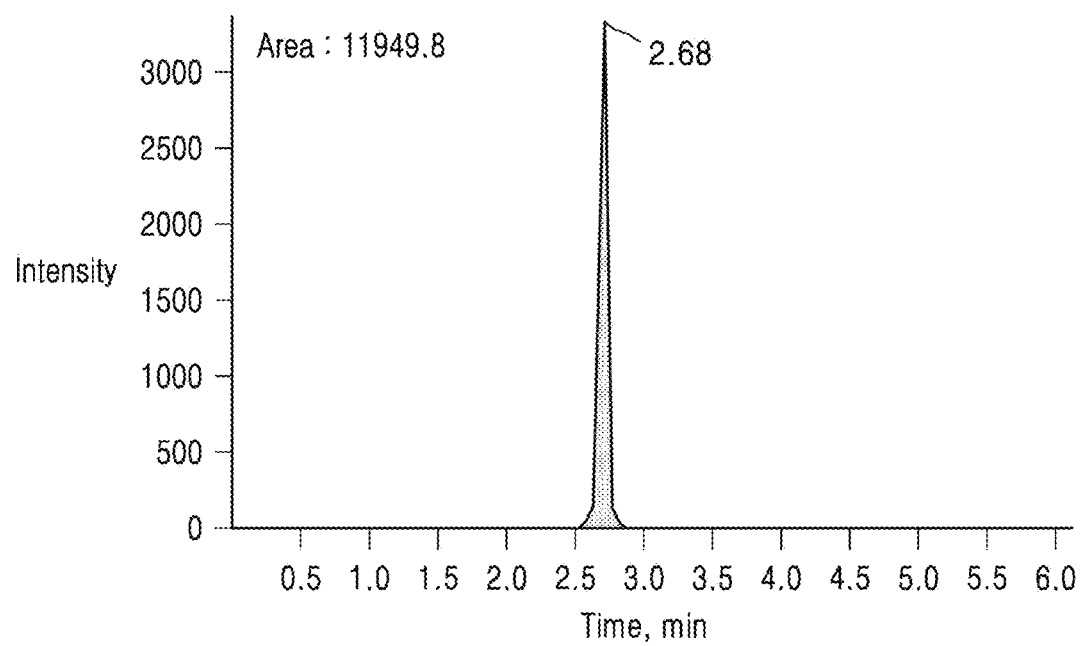
Figure 4D:
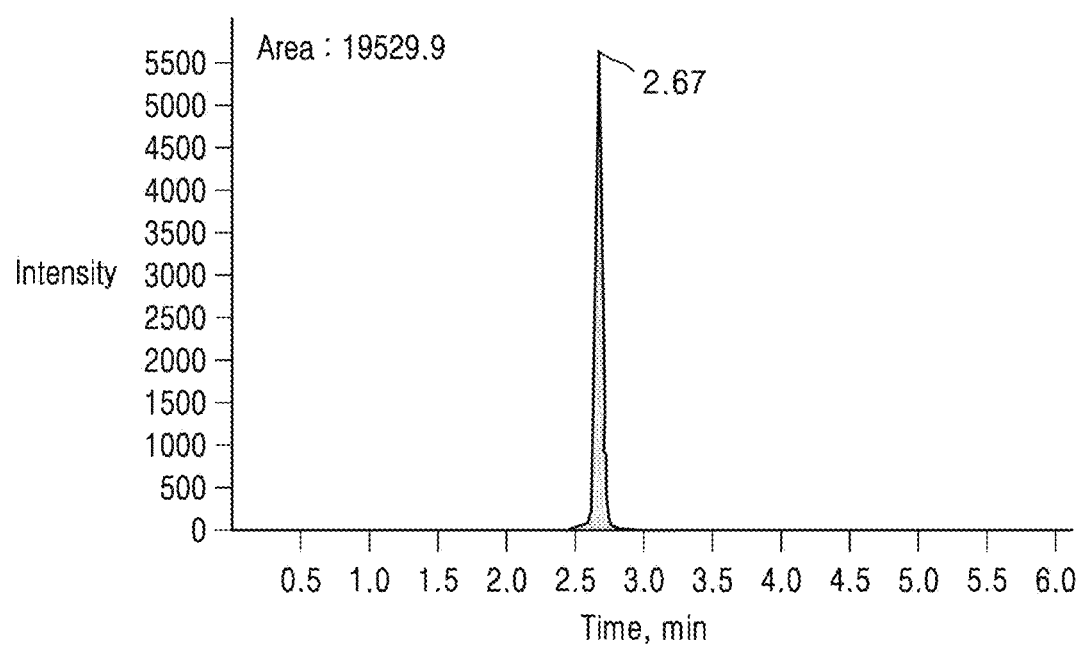
Figure 4E:
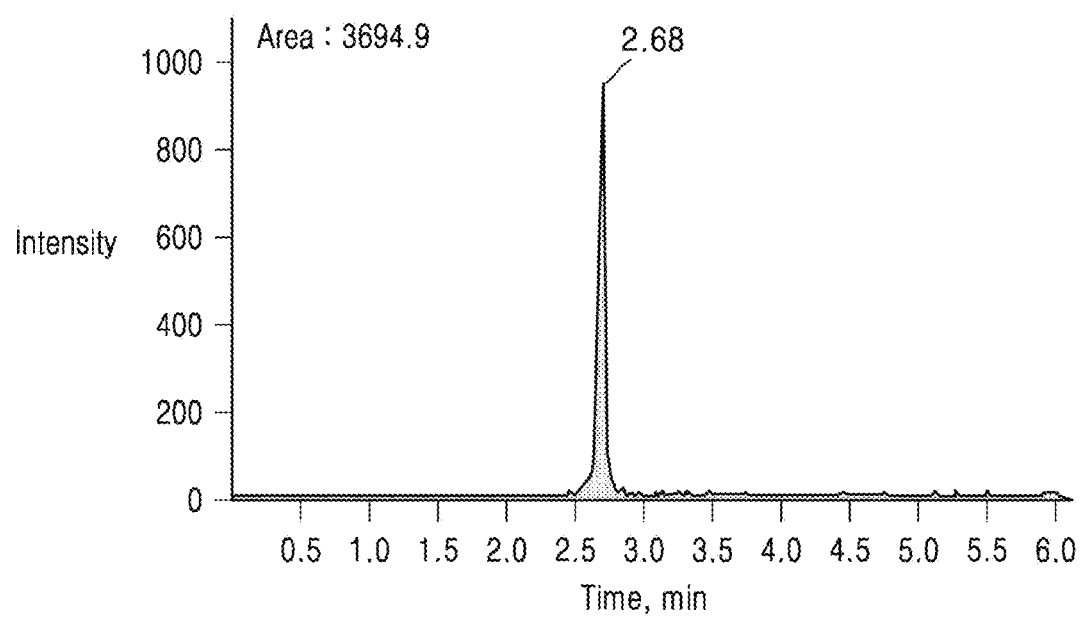
Figure 12A:
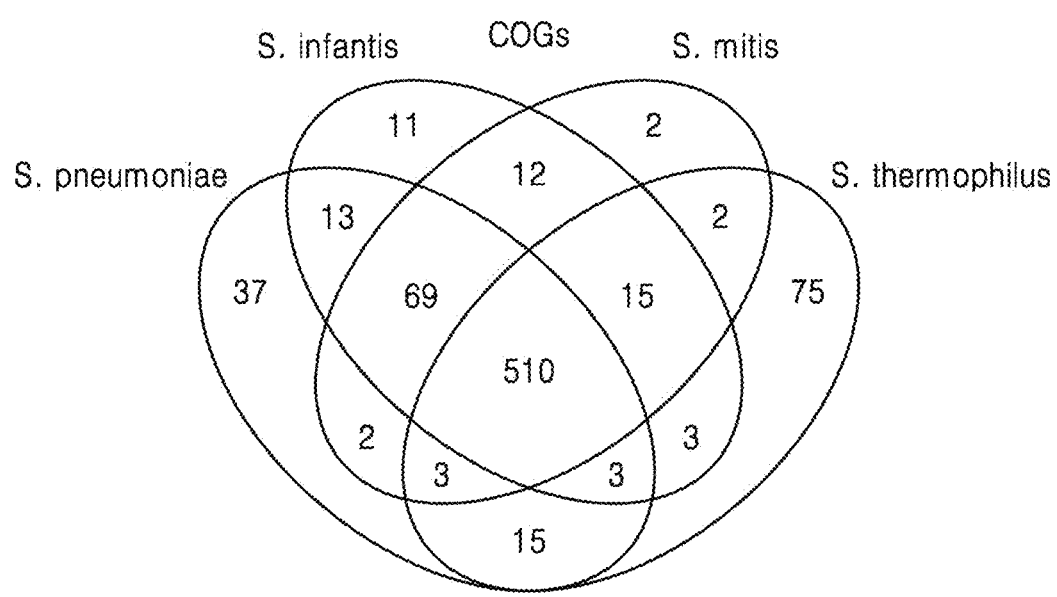
Figure 12B:
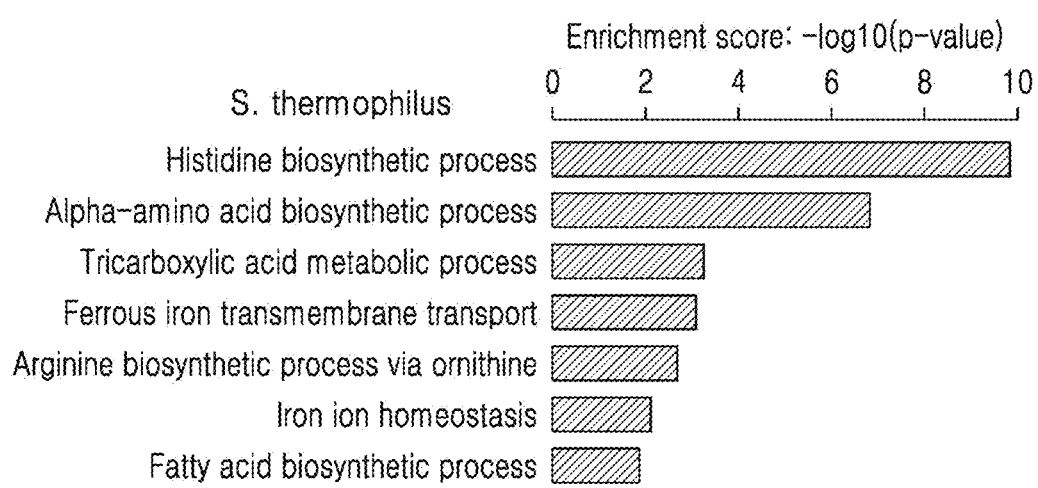

Annotation was made on genome fragments, and the entire genome analysis was performed to select common genes, orthologous population clusters thereof were compared, and functional roles thereof were identified (FIGS. 3B and 12A). Gene ontology terms, such as single organism carbohydrate metabolic process, glyceraldehyde-3-phosphate metabolic process, L-ascorbic acid transport, or glycogen biosynthetic process, are enriched in the Streptococcus infantis (FIG. 3C). Gene ontology terms, such as monosaccharide metabolic process, L-ascorbic acid catabolic process, or hexose metabolic process, are enriched in the Streptococcus pneumoniae (FIG. 3D). Gene ontology terms, such as glyceraldehyde-3-phosphate metabolic process, glycogen biosynthetic process, glycerol-3-phosphate metabolic process, or spermidine biosynthetic process, are enriched in the Streptococcus mitis (FIG. 3E).

Figure 13:
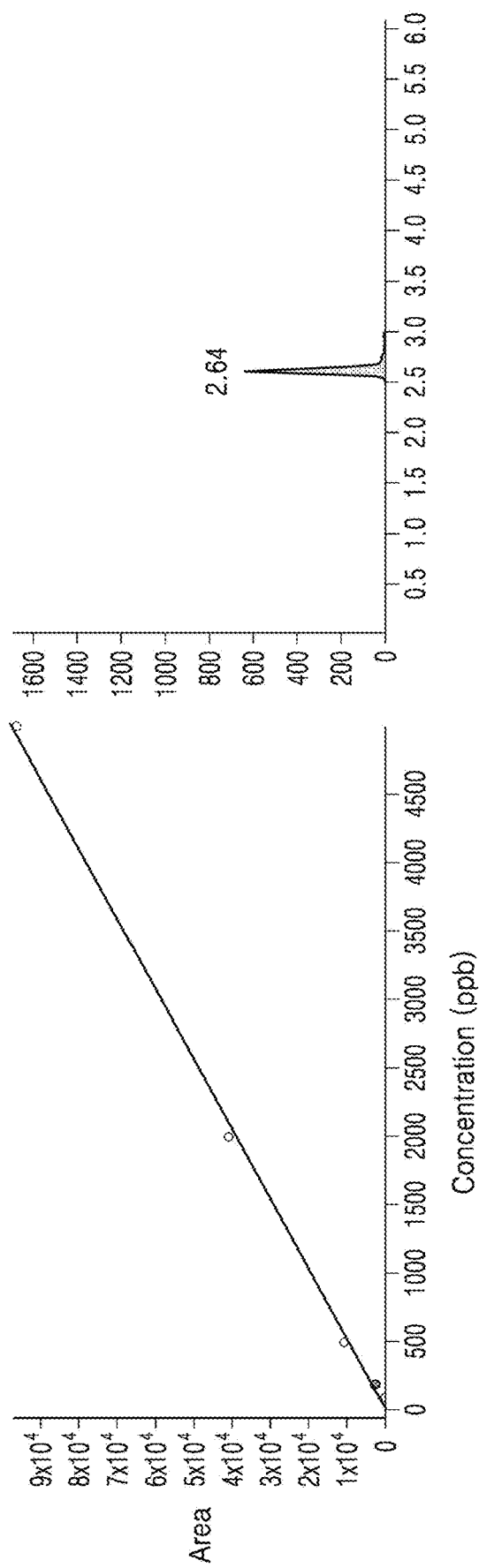
FIG. 13 shows the result of detecting spermidine in St solutions using UPLCQTOF-ESI-MS chromatograms, in which the left view is a representation of a calibration curve for spermidine (eluted at 2.68 min), and the right view shows UPLC-QTOF-ESI-MS chromatograms of 200 ppb spermidine used in plotting the calibration curve.

Spermidine biosynthetic process, phospholipid biosynthetic process, and glycogen biosynthetic process were included in the common terms. In addition, in order to confirm the genome analysis for discriminating the biosynthetic pathway of sperm idine, the spermidine in the St solution was quantified from peak intensity based on the calibration curve obtained by using the St solution (FIG. 13). The calibration curve for spermidine which was eluted at 2.68 min was made using 5 concentrations (1 to 5000 µg/L) (FIG. 13). The measured amounts of spermidine contained in the St solution were 332.8 µg/mL (TSB), 361.3 µg/mL (Streptococcus infantis), 635.3 µg/mL (Streptococcus pneumoniae), 1026.9 µg/mL (Streptococcus mitis), and 208.8 µg/mL (Streptococcus thermophilus) (FIGS. 4A to 4E).

5. Confirmation of Capability of Streptococcus Products in Improving Complex Dermatophysiology In order to link the above results with skin layer improvement, the cheeks of a healthy volunteer without a skin disease were treated with an emulsion including the St solution (St emulsion).

After 4 weeks, the St emulsion significantly improved a variety of skin parameters (FIG. 5).

Figure 5A:
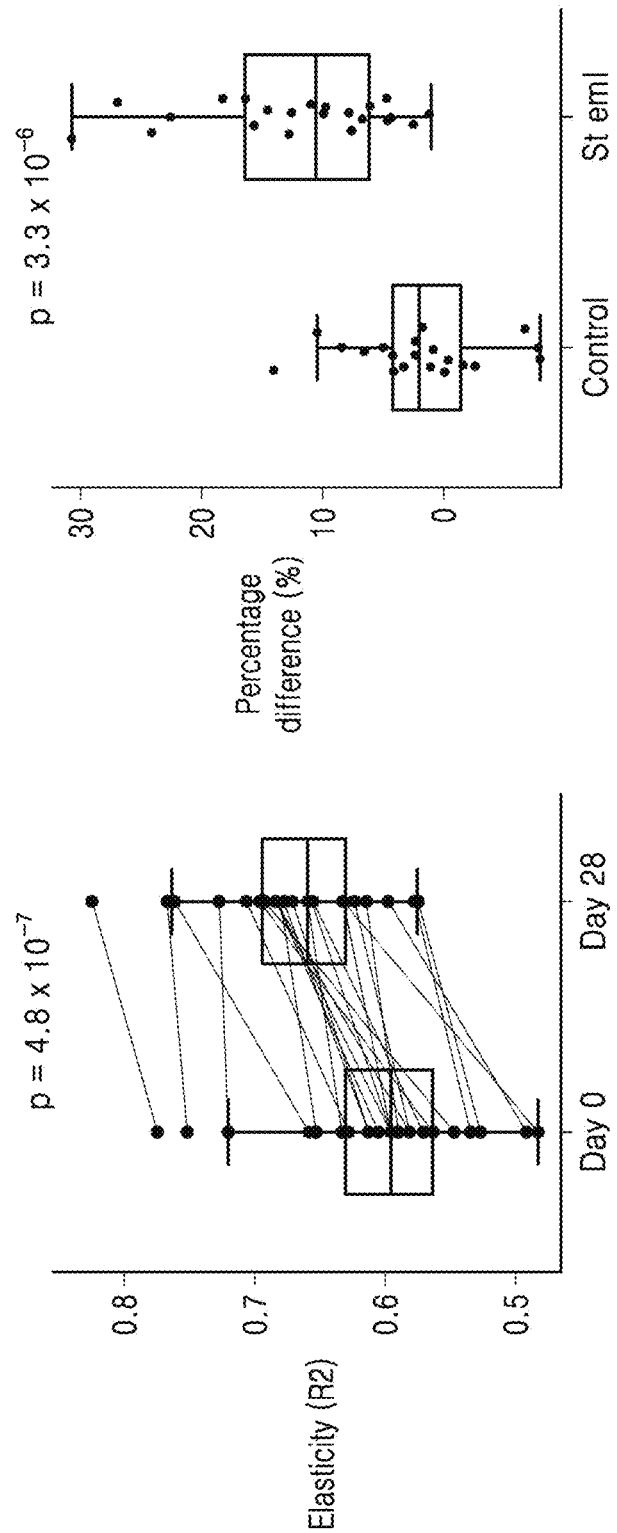
FIG. 5A, FIG. 5B, FIG. 5C, FIG. 5D, FIG. 5E, FIG. 5F, and FIG. 5G show clinical improvement degrees of facial parameters after applying *Streptococcus* emulsion.
Figure 14A:
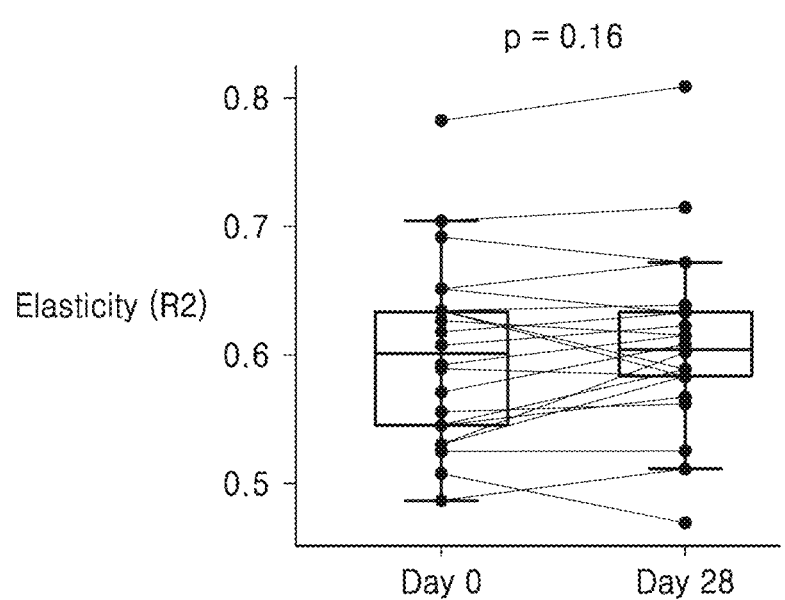
FIG. 14A, FIG. 14B, FIG. 14C, FIG. 14D, FIG. 14E, FIG. 14F, and FIG. 14G show changes in the face condition after applying St emulsions and control emulsions.

As predicted from increased expression levels of collagen and elastin genes, skin elasticity was increased (mean±standard deviation: 0.06±0.041; 12.1%) by applying the St emulsion, while the control group showed no significant difference and the skin elasticity of the control group was maintained at the standard level during the test period (mean±standard deviation: 0.008±0.030) (FIGS. 5A and 14A).

Figure 5B:
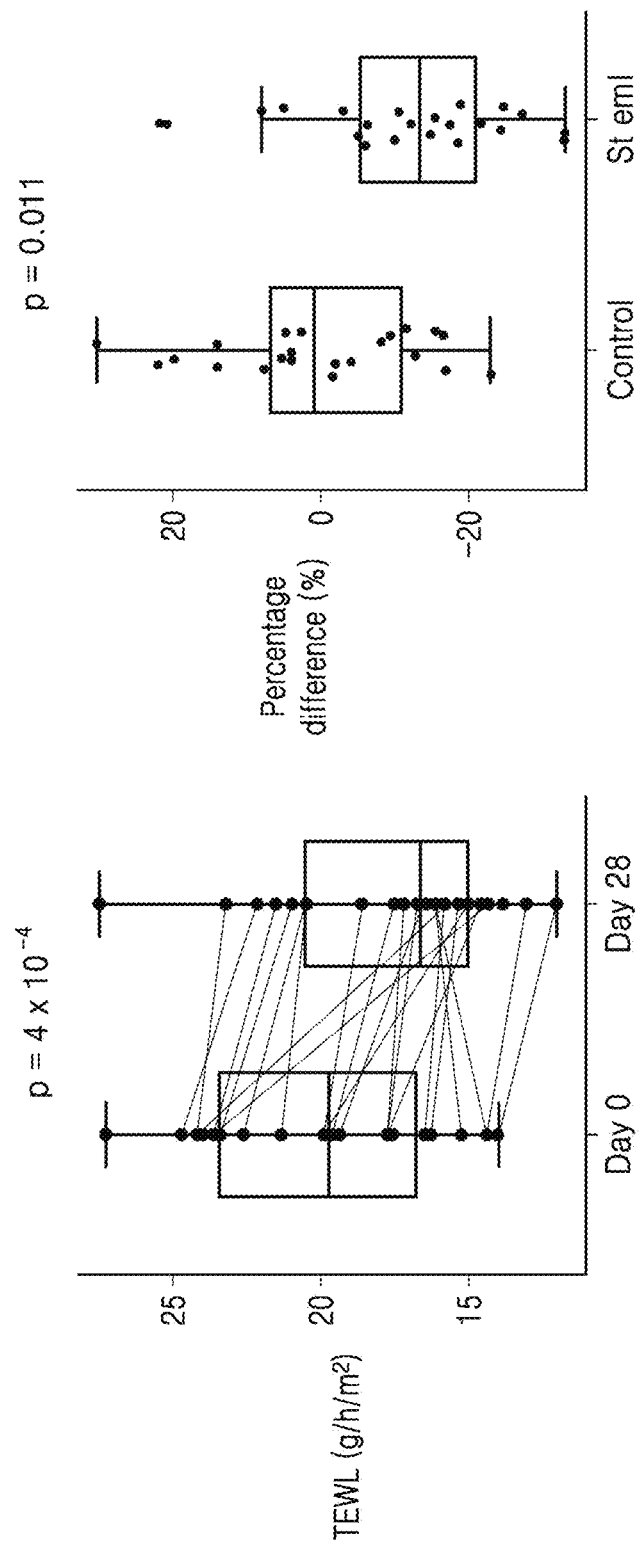
Figure 5C:
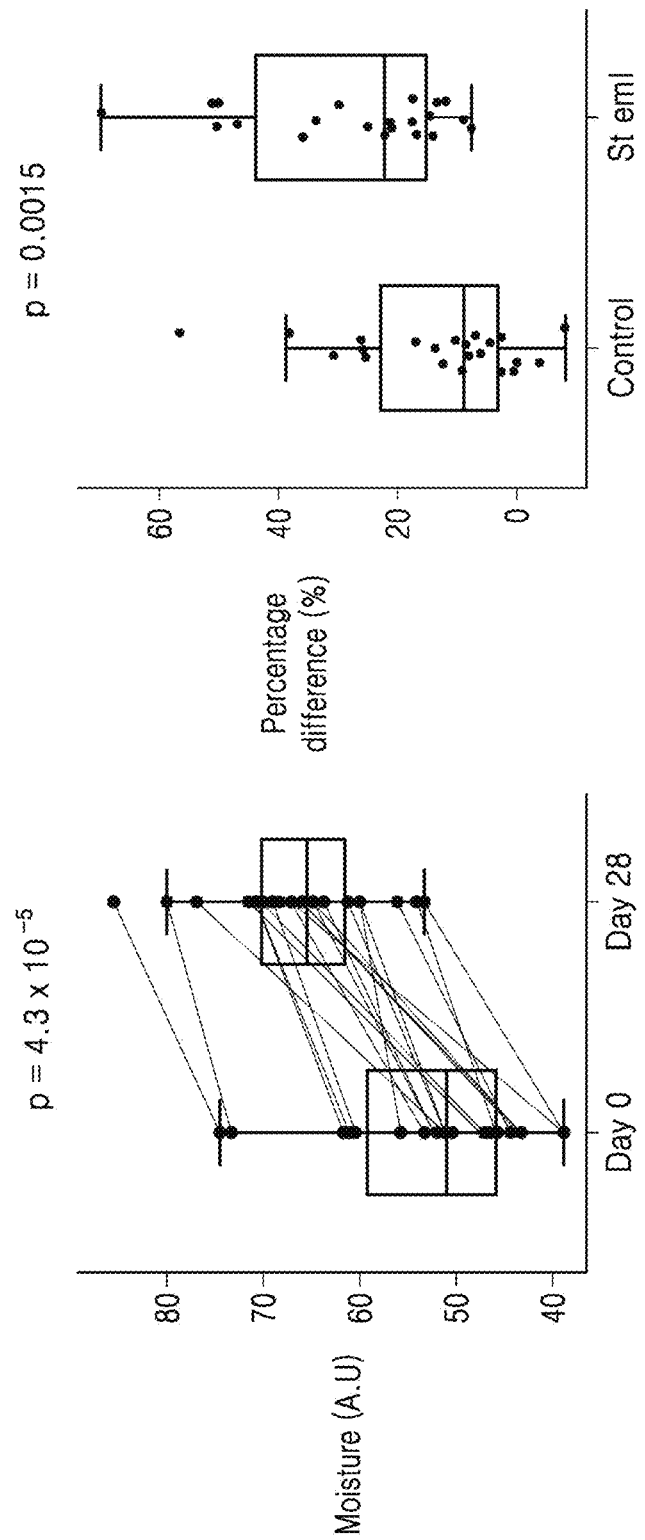
Figure 14B:
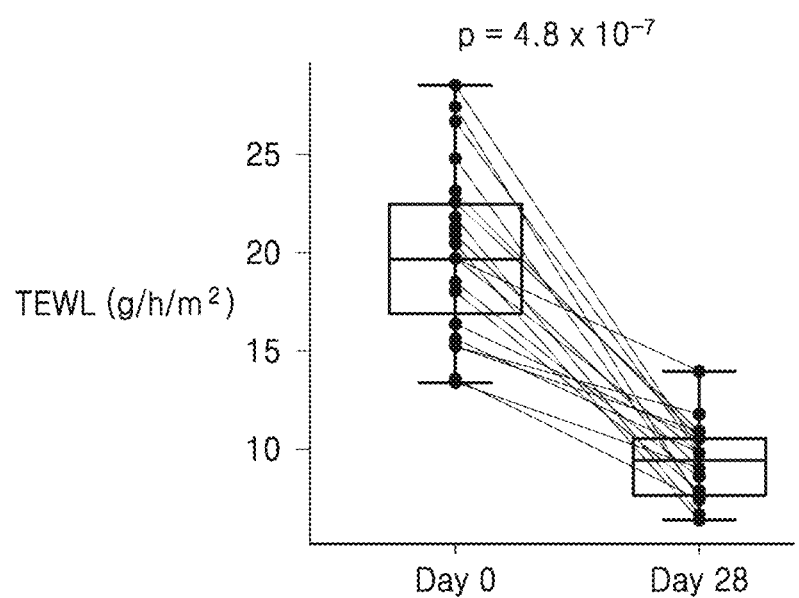
Figure 14C:
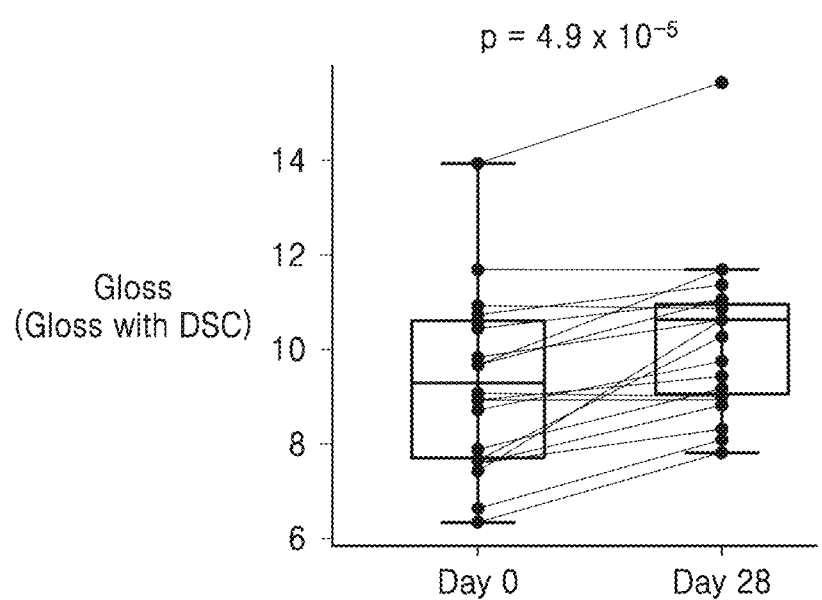

The effect of the St emulsion on skin moisturization was determined by analyzing the TEWL and water content of stratum corneum, and the result showed that the St emulsion treated group showed a reduction of 2.451±3.304 (mean±standard deviation; 11.3%) at 4 weeks after the St emulsion treatment, while the control group had no significant reduction in the TEWL score (FIGS. 5B and 14B). In addition, the St solution treated group showed a significantly higher skin hydration level at 4 weeks after St emulsion treatment than that before treatment (at 52.40±0.379 A.U, 66.386±7.729 A.U; 28.7% increase), as compared to control group (at 51.833±8.745 A.U, 57.965±7.675 A.U; 13.3% increase), and the increase rate was significantly higher than that of the control group (FIGS. 5C and 14C).

Figure 5D:
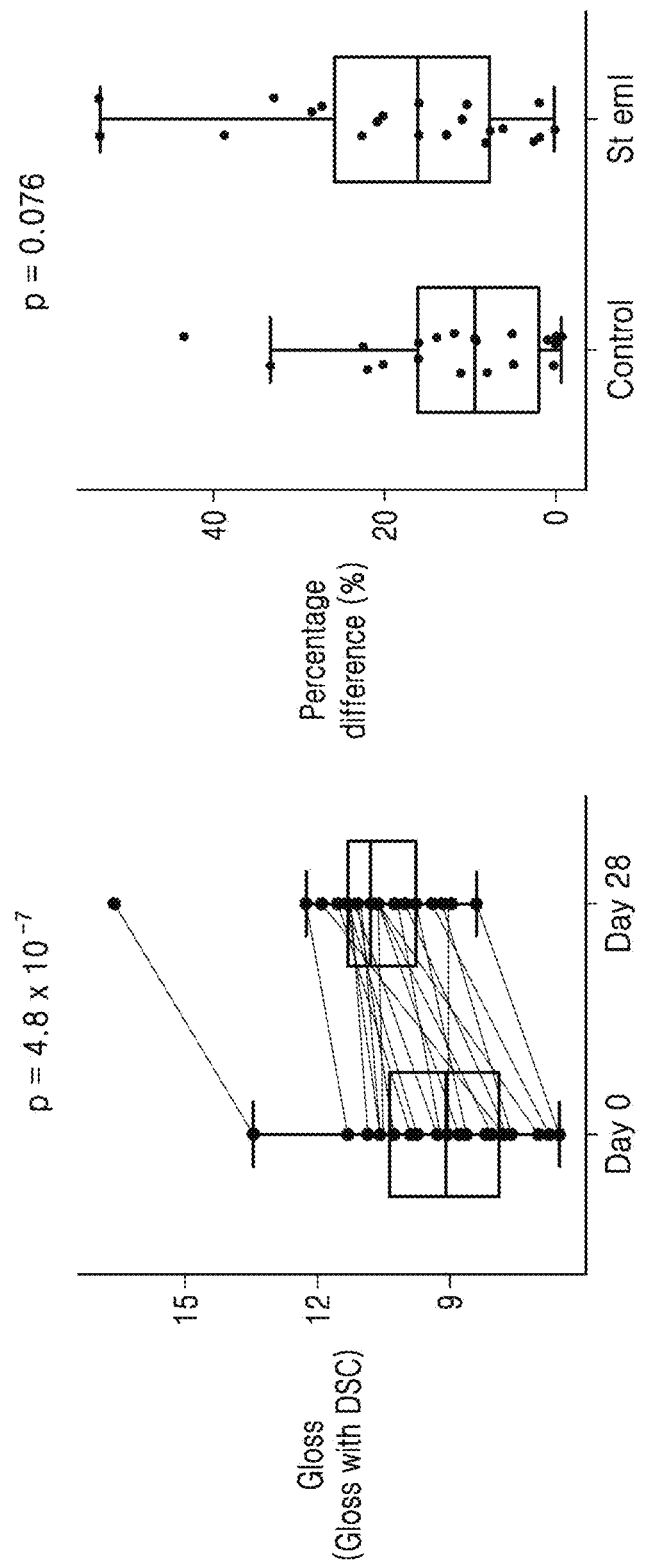
Figure 5E:
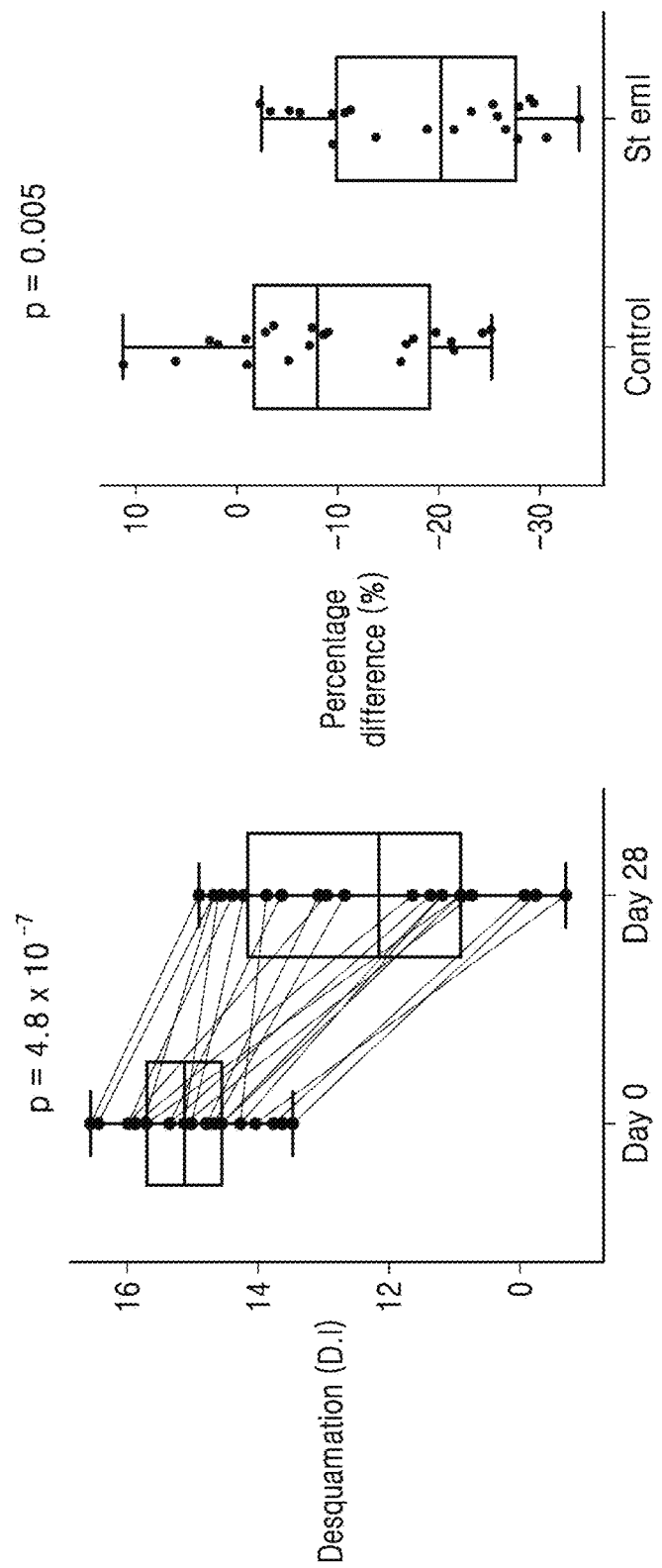
Figure 5F:
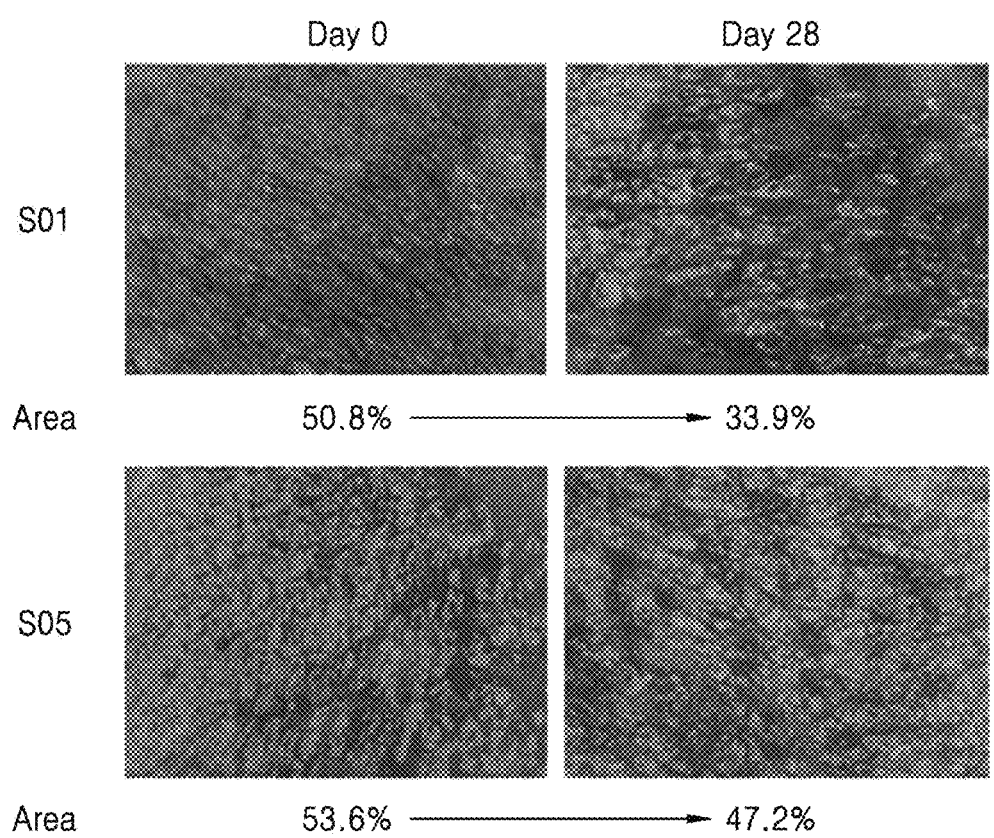
Figure 5G:
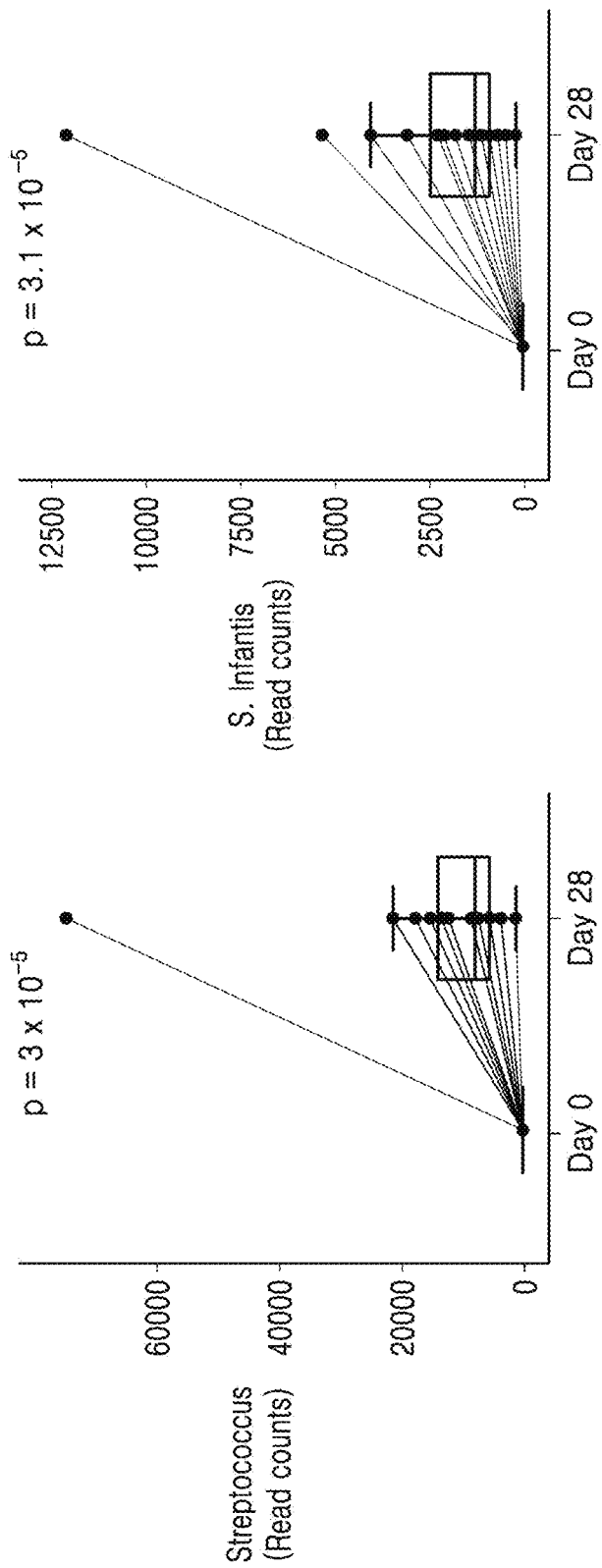
Figure 14D:
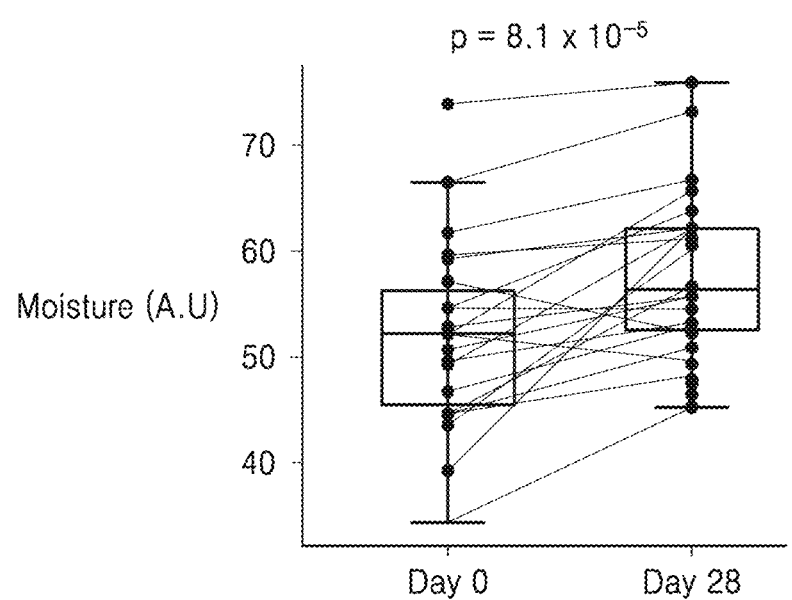
Figure 14E:
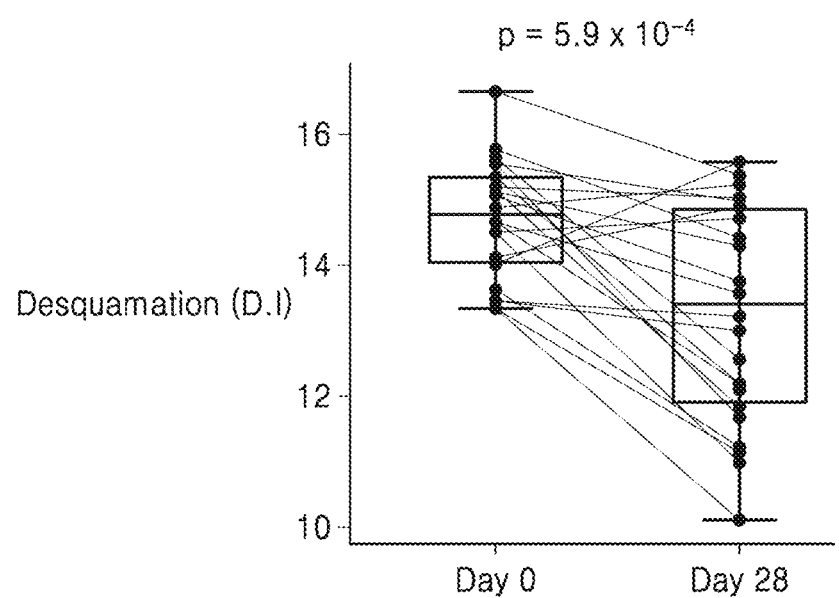

To confirm the effect exerted by the increased amount of skin lipids, facial gloss was evaluated. With regard to reference skin gloss value, the St emulsion treated group was 9.160±1.682, and the emulsion treated control group was 9.259±1.782. At 4 weeks after the treatment, it was confirmed that the St emulsion treated group showed increased skin gloss by 19.1% and the emulsion treated control group showed increased skin gloss by 11.8%, confirming that the St emulsion significantly improved skin gloss levels (FIGS. 5D and 14D).

In addition, the improved water content and lipid composition in the St emulsion treated group reduced skin desquamation, which is generally increased in old people. The desquamation index (DI) was determined by a reduction in the area of keratinocytes. In the St emulsion-treated group, DI was dramatically lower after 4 weeks compared to the baseline, corresponding to a 18.4% reduction. Meanwhile, the DI of the control group was reduced by only 9.7%.

Figure 14F:
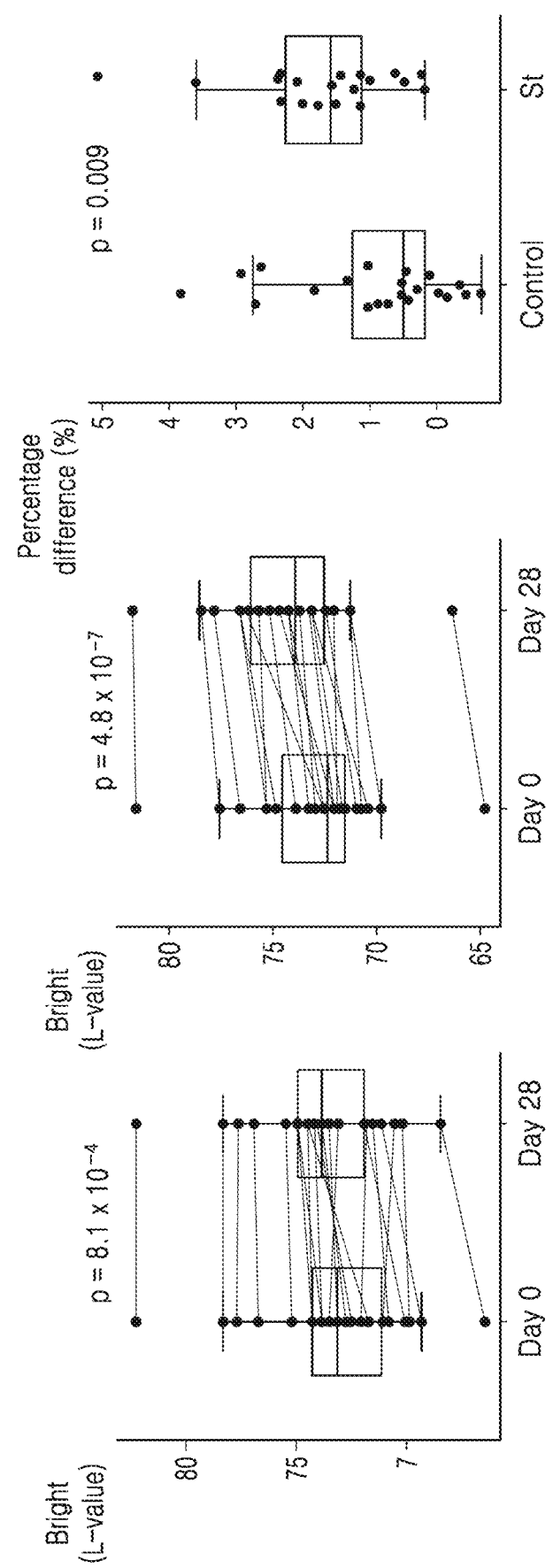
Figure 14G:
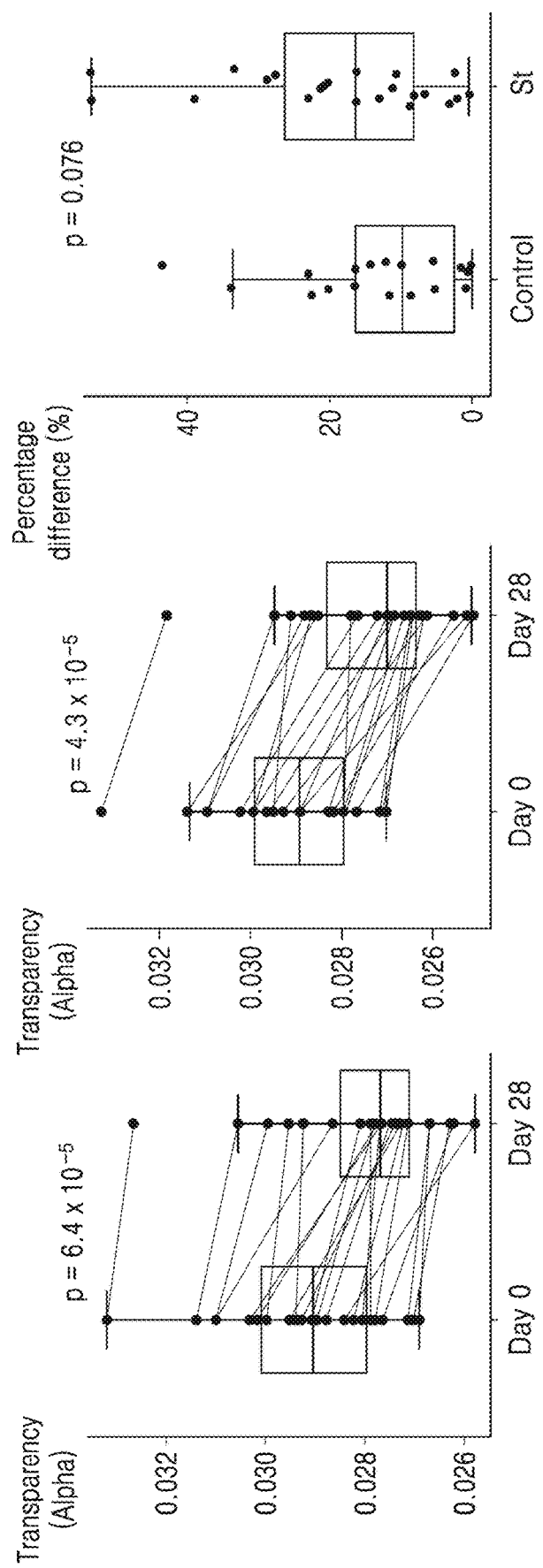

In addition, at 4 weeks after treatment, the skin brightness was significantly increased by 1.784 in the St emulsion treated group (increased by 0.909 in the control group; FIG. 14F), and the skin transparency was reduced by 6.280% (FIG. 14G).

These results suggest that the St emulsion is capable of improving skin conditions of multidimensional skin layers while efficiently improving physiological parameters associated with aging and barrier function of skin.

6. Analysis of Substance Utilization by Isolated Strains

To analyze substance utilization by the isolated strains (*Streptococcus pneumoniae, Streptococcus infantis*, and *Streptococcus mitis*), tests were conducted in the following manner. BioLOG GP2 and API 50 were used in determining the substance utilization, and testing was performed using testing methods provided by Omnilog and Biomeriuse. The culturing temperature and media suitable to corresponding strains were selected, and 5 among cluster colonies incubated for 48 hours were taken and suspended in reagents before use. The inoculation amount was 150 μl. As the suspension, components of kits provided by various manufacturers were used. When the strains are yet to be inoculated, the suspension is in a transparent liquid phase. Inoculated plates and strips were incubated at 37° C. for 48 hours, and then the incubation of up to 72 hours was examined. Wells were in a transparent liquid phase at the time of inoculating, but the colors of the wells changed to purple or red, and the color-changed wells were determined to be positive. The results of the experiments conducted as described above are listed in Table 5.

TABLE 5

| | S. pneumoniae (CX-2) | S. infantis (CX-4) | S. mitis (CX-8) |
|---|---|---|---|
| Negative Control | | | |
| D-Raffinose | + | | |
| α-D-Glucose | + | + | + |
| D-Sorbitol | | | |
| Gelatin | | | |
| Pectin | + | + | + |
| p-Hydroxy-Phenylacetic Acid | | | |
| Tween 40 | + | + | |
| Dextrin | + | + | + |
| α-D-Lactose | + | + | + |
| D-Mannose | + | + | + |
| D-Mannitol | | | |
| Glycyl-L-Proline | | | |
| D-Galacturonic Acid | | | + |
| Methyl Pyruvate | | | |
| γ-Amino-Butyric Acid | | | |
| D-maltose | + | + | + |
| D-Melibiose | + | | |
| D-Fructose | + | + | + |
| D-Arabitol | | | |
| L-Alanine | | | |
| L-Galactonic Acid Lactone | | | + |
| D-Lactic Acid Methyl Ester | | | |
| α-Hydroxy-Butyric Acid | + | | |
| D-Trehalose | | | |
| β-Methyl-D-Glucoside | | | |
| D-Galactose | | + | + |
| myo-Inositol | | | |
| L-Arginine | | | |
| D-Gluconic Acid | | | |
| L-Lactic Acid | | | |
| β-Hydroxy-D,L-Butyric Acid | | | |
| D-Cellobiose | + | + | + |
| D-Salicin | | | + |
| 3-Methyl Glucose | | | |
| Glycerol | | + | |
| L-Aspartic Acid | | | |
| D-Glucuronic Acid | | | |
| Citric Acid | | | |
| α-Keto-Butyric Acid | | | |
| Gentiobiose | | + | + |
| N-Acetyl-D-Glucosamine | | + | + |
| D-Fucose | | | |
| D-Glucose-6-PO4 | | | |
| L-Glutamic Acid | | | |

TABLE 5-continued

| | S. pneumoniae (CX-2) | S. infantis (CX-4) | S. mitis (CX-8) |
|---|---|---|---|
| Glucuronamide | + | | + |
| α-keto-Glutaric Acid | | | |
| Acetoacetic Acid | + | + | + |
| Sucrose | + | + | + |
| N-Acetyl-β-D-Mannosamine | + | + | + |
| L-Fucose | | | |
| D-Fructose-6-Po4 | | | + |
| L-Histidine | | | |
| Mucic Acid | | | |
| D-Malic Acid | | | |
| Propionic Acid | | + | |
| D-Turanose | + | | |
| N-Acetyl-D-Galactosamine | | + | |
| L-Rhamnose | | | |
| D-Aspartic Acid | | | |
| L-Pyroglutamic Acid | | | |
| Quinic Acid | | | |
| L-Malic Acid | | | |
| Acetic Acid | + | + | |
| Stachyose | + | + | + |
| N-Acetyl Neuraminic Acid | | + | + |
| Inosine | | + | |
| D-Serine | | | |
| L-Serine | | | |
| D-Saccharic Acid | | | |
| Bromo-Succinic Acid | | | |
| Formic Acid | | + | |
| Positive control | + | + | + |
| pH 6 | + | + | + |
| pH 5 | | | |
| 1% NaCl | + | + | + |
| 4% NaCl | | | + |
| 8% NaCl | | | + |
| 1% Sodium Lactate | + | + | + |
| Fusidic acid | | + | + |
| D-Serine | | + | + |
| Troleandomycin | | + | + |
| Rifamycin SV | | + | + |
| Minocycline | | + | + |
| Lincomycin | | + | + |
| Guanidine HCl | | | + |
| Niaproof 4 | | | |
| Vancomycin | | + | + |
| Tetrazolium Violet | | + | + |
| Tetrazolium Blue | | + | + |
| Nalidixic Acid | + | + | + |
| Lithium Chloride | | | + |
| Potassium Tellurite | + | + | + |
| Aztreonam | + | + | + |
| Sodium Butyrate | | | + |
| Sodium Bromate | | | |

[Accession Number]

Depositary Institution: Korean Culture Center of Microorganisms (overseas)

Accession number: KCCM12656P

Commissioned date: Jan. 15, 2020

The composition provided in an aspect comprises a novel strain, a lysate thereof or a culture product thereof, and can demonstrate excellent effects in strengthening skin barrier, moisturizing skin, enhancing skin elasticity or anti-aging, and thus can be used for a cosmetic composition or health functional food.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A composition comprising a culture supernatant of a *Streptococcus mitis* strain under accession No. KCCM12656P cultured in MRS (de Man, Rogosa and Sharpe) broth, wherein the culture supernatant is a culture liquid from which the *S. mitis* cells have been removed, and wherein the culture supernatant comprises spermidine.

2. The composition of claim 1, wherein the *S. mitis* strain has a 16S rRNA sequence having at least 98% sequence identity to SEQ ID NO. 1.

3. The composition of claim 1, wherein the composition is for improving skin conditions.

4. The composition of claim 3, wherein the improving of skin conditions includes skin barrier strengthening, skin moisturization, skin elasticity enhancement, or anti-aging, or combinations of two of more thereof.

5. The composition of claim 1, wherein the composition is a cosmetic composition, a pharmaceutical composition, or a composition for skin external use.

6. The composition of claim 1, further comprising a cosmetically or pharmaceutically acceptable carrier.

7. The composition of claim 1, wherein the composition is a health functional food composition.

8. A method for improving skin conditions of a subject, the method comprising:
 administering a composition comprising a therapeutically effective amount of a culture supernatant of a *Streptococcus mitis* strain under accession No. KCCM12656P cultured in MRS (de Man, Rogosa and Sharpe) broth to a subject in need thereof, wherein the culture supernatant is a culture liquid from which the *S. mitis* cells have been removed, and wherein the culture supernatant comprises spermidine.

9. The method of claim 8, wherein the improving of skin conditions includes skin barrier strengthening, skin moisturization, skin elasticity enhancement, or anti-aging, or combinations of two of more thereof.

10. The method of claim 8, wherein the composition is a cosmetic composition, a pharmaceutical composition, or a composition for skin external use.

11. The method of claim 8, wherein the composition is a health function food composition.

\* \* \* \* \*